(12) United States Patent
Sasaki et al.

(10) Patent No.: US 9,073,864 B2
(45) Date of Patent: Jul. 7, 2015

(54) AROMATIC RING COMPOUND

(71) Applicant: TAKEDA PHARMACEUTICAL COMPANY LIMITED, Osaka (JP)

(72) Inventors: Minoru Sasaki, Kanagawa (JP); Hideki Furukawa, Kanagawa (JP); Kousuke Hidaka, Kanagawa (JP); Kyoko Toyofuku, Kanagawa (JP); Takatoshi Yogo, Kanagawa (JP); Toshiki Murata, Kanagawa (JP)

(73) Assignee: Takeda Pharmaceutical Company Limted, Osaka (JP)

(*) Notice: Subject to any disclaimer, the term of this patent is extended or adjusted under 35 U.S.C. 154(b) by 0 days.

(21) Appl. No.: 14/389,004

(22) PCT Filed: Mar. 28, 2013

(86) PCT No.: PCT/JP2013/059265
§ 371 (c)(1),
(2) Date: Sep. 29, 2014

(87) PCT Pub. No.: WO2013/147026
PCT Pub. Date: Oct. 3, 2013

(65) Prior Publication Data
US 2015/0152052 A1 Jun. 4, 2015

(30) Foreign Application Priority Data
Mar. 29, 2012 (JP) ................. 2012-078133

(51) Int. Cl.
| | | |
|---|---|---|
| *C07D 211/06* | (2006.01) | |
| *A61K 31/445* | (2006.01) | |
| *C07D 211/60* | (2006.01) | |
| *C07D 401/12* | (2006.01) | |
| *C07D 401/06* | (2006.01) | |
| *C07D 413/12* | (2006.01) | |
| *C07D 498/04* | (2006.01) | |
| *C07D 405/14* | (2006.01) | |

(52) U.S. Cl.
CPC ............ *C07D 211/60* (2013.01); *C07D 401/12* (2013.01); *C07D 401/06* (2013.01); *C07D 413/12* (2013.01); *C07D 498/04* (2013.01); *C07D 405/14* (2013.01)

(58) Field of Classification Search
CPC ........................... C07D 211/32; A61K 31/445
USPC .......................................... 546/226; 514/330
See application file for complete search history.

(56) References Cited

U.S. PATENT DOCUMENTS

| | | |
|---|---|---|
| 2008/0300308 A1 | 12/2008 | Li et al. |
| 2010/0041891 A1 | 2/2010 | Setoh et al. |
| 2010/0256156 A1 | 10/2010 | Banno et al. |
| 2012/0053173 A1 | 3/2012 | Banno et al. |

FOREIGN PATENT DOCUMENTS

| | | |
|---|---|---|
| JP | 2009-519226 | 5/2009 |
| WO | 02/00647 | 1/2002 |
| WO | 2004/065351 | 8/2004 |
| WO | 2005/019167 | 3/2005 |
| WO | 2009/057784 | 5/2009 |
| WO | WO 2009/080367 | * 7/2009 |
| WO | 2009/110520 | 9/2009 |
| WO | 2011/027849 | 3/2011 |
| WO | 2012/085745 | 6/2012 |
| WO | 2012/107850 | 8/2012 |
| WO | 2013/014569 | 1/2013 |

OTHER PUBLICATIONS

International Search Report dated Apr. 23, 2013 issued in International (PCT) Application No. PCT/JP2013/059265.

* cited by examiner

*Primary Examiner* — John Mabry
(74) *Attorney, Agent, or Firm* — Wenderoth, Lind & Ponack, L.L.P.

(57) ABSTRACT

Provided is an aromatic ring compound having a glucagon antagonistic action, which is useful for the prophylaxis or treatment of diabetes and the like. A compound represented by the formula (I):

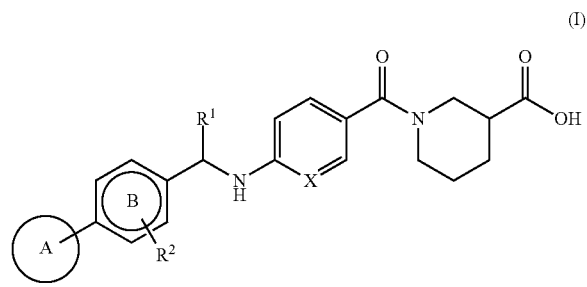

wherein each symbol is as defined in the DESCRIPTION, or a salt thereof has a superior glucagon antagonistic action, and is useful as a glucagon antagonist, a glucose production inhibitor or an agent for the prophylaxis or treatment of diabetes and the like.

16 Claims, No Drawings

AROMATIC RING COMPOUND

TECHNICAL FIELD

The present invention relates to an aromatic ring compound having a glucagon receptor antagonistic action and useful for the prophylaxis or treatment of diabetes and the like.

BACKGROUND OF THE INVENTION

Glucagon is a straight chain peptide hormone consisting of 29 amino acids, which is secreted from a cell of pancreas, and promotes glycogenolysis and gluconeogenesis in the liver. In diabetes patients, secretion and reactivity of glucagon is generally promoted, which is one of the factors causing hyperglycemia. Therefore, a glucagon receptor antagonist can suppress excess glucose production by the liver by blocking the action of glucagon, and is useful as a therapeutic drug for diabetes.

Patent document 1 describes the following compound.
A compound represented by the following formula:

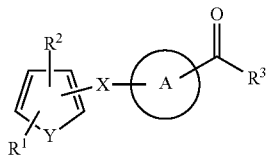

(I)

wherein ring A is a benzene ring or a 5- or 6-membered heterocycle, each of which is optionally further substituted;
Y is an oxygen atom, a sulfur atom or a nitrogen atom;
X is —O—, —S—, —SO—, —SO$_2$—, —CR$^4$R$^5$—O—, —O—CR$^4$R$^5$—, —CO—CR$^4$R$^5$—, —CR$^4$R$^5$CO—, —CR$^4$R$^5$—NR$^6$— or —CO—NR$^6$—;
R$^4$ is a hydrogen atom or a C$_{1-6}$ alkyl group;
R$^5$ and R$^6$ are each independently a hydrogen atom, an optionally substituted C$_{1-6}$ alkyl group, an optionally substituted C$_{3-10}$ cycloalkyl group, an optionally substituted C$_{6-14}$ aryl group, or an optionally substituted 5- or 6-membered heterocyclic group;
R$^1$ is an optionally substituted hydrocarbon group, an optionally substituted heterocyclic group, an optionally substituted hydroxy group or an acyl group;
R$^2$ is a hydrogen atom, an optionally substituted hydrocarbon group, an optionally substituted heterocyclic group, an optionally substituted hydroxy group or an acyl group;
R$^3$ is —(CH$_2$)$_3$—COOH or —NR$^7$—CR$^8$R$^9$—CR$^{10}$R$^{11}$—COOH;
R$^7$, R$^8$, R$^9$ and R$^{10}$ are each independently a hydrogen atom or a C$_{1-6}$ alkyl group; and
R$^{11}$ is a hydrogen atom, a C$_{1-6}$ alkyl group or a hydroxy group, provided that when Y is a nitrogen atom, then ring A is not optionally substituted pyrrole, or a salt thereof.

Patent document 2 describes the following compounds.
A compound represented by the following formula:

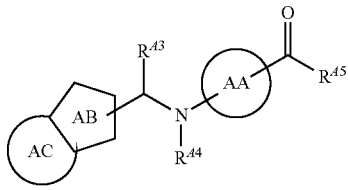

(IA)

wherein ring AA is an optionally substituted benzene ring, or an optionally substituted 5- or 6-membered aromatic heterocycle;
ring AB is an optionally substituted 5-membered aromatic heterocycle;
ring AC is an optionally substituted benzene ring, or an optionally substituted 5- or 6-membered aromatic heterocycle;
R$^{A3}$ is an optionally substituted a C$_{1-6}$ alkyl group, an optionally substituted C$_{3-10}$ cycloalkyl group, an optionally substituted C$_{6-14}$ aryl group or an optionally substituted heterocyclic group;
R$^{A4}$ is a hydrogen atom or a C$_{1-6}$ alkyl group;
R$^{A5}$ is —(CH$_2$)$_3$—COOR$^{411}$ or —NR$^{46}$—CR$^{47}$R$^{48}$—CR$^{49}$R$^{410}$—COOR$^{411}$;
R$^{46}$, R$^{47}$, R$^{48}$, R$^{49}$ and R$^{411}$ are each independently a hydrogen atom or a C$_{1-6}$ alkyl group;
R$^{410}$ is a hydrogen atom, a alkyl group or hydroxy group, or a salt thereof; and
a compound represented by the following formula:

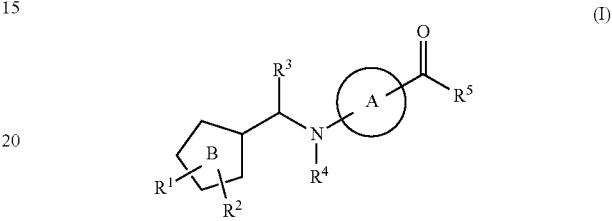

(I)

wherein ring A is an optionally substituted benzene ring, or an optionally substituted 5- or 6-membered aromatic heterocycle; ring B is pyrazole;
R$^1$ and R$^2$ are each independently an optionally substituted hydrocarbon group, an optionally substituted heterocyclic group, an optionally substituted hydroxy group or acyl;
R$^3$ is an optionally substituted a C$_{1-6}$ alkyl group, an optionally substituted C$_{3-10}$ cycloalkyl group, an optionally substituted C$_{6-14}$ aryl group or an optionally substituted heterocyclic group;
R$^4$ is a hydrogen atom or a C$_{1-6}$ alkyl group;
R$^5$ is —(CH$_2$)$_3$—COOR$^{11}$ or —NR$^6$—CR$^7$R$^8$—CR$^9$R$^{10}$—COOR$^{11}$;
R$^6$, R$^7$, R$^8$, R$^9$ and R$^{11}$ are each independently a hydrogen atom or a C$_{1-6}$ alkyl group;
R$^{10}$ is a hydrogen atom, a C$_{1-6}$ alkyl group or a hydroxy group, excluding N-[4-[[(1-phenyl-5-propyl-1H-pyrazol-4-yl)methyl]amino]benzoyl]-β-alanine, or a salt thereof.

Patent document 3 describes the following compounds.
3-{[(6-{[(5-chloro-1-methyl-1H-indol-2-yl)(cyclohexyl)methyl]amino}pyridin-3-yl)carbonyl](methyl)amino}propanoic acid or a salt thereof;
3-{[(6-{[cyclohexyl(5-fluoro-1-methyl-1H-indol-2-yl)methyl]amino}pyridin-3-yl)carbonyl](methyl)amino}propanoic acid or a salt thereof;
3-{[(6-{[(5-chloro-1-methyl-1H-indol-2-yl)(cyclopentyl)methyl]amino}pyridin-3-yl)carbonyl](methyl)amino}propanoic acid or a salt thereof;
3-{[(4-{[(5-chloro-3-methylthieno[2,3-c]pyridin-2-yl)(cyclohexyl)methyl]amino}phenyl)carbonyl](methyl)amino}-propanoic acid or a salt thereof;
3-{[(6-{[(6-chloro-3-methylthieno[3,2-c]pyridin-2-yl)(cyclohexyl)methyl]amino}pyridin-3-yl)carbonyl](methyl)amino}propanoic acid or a salt thereof; and
3-{[(4-{[(6-chloro-3-methylthieno[3,2-c]pyridin-2-yl)(cyclohexyl)methyl]amino}phenyl)carbonyl](methyl)amino}-propanoic acid or a salt thereof.

Patent document 4 describes the following compound.
A compound represented by the following formula:

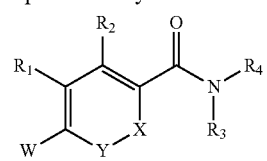

wherein $R_1$ and $R_2$ are each a hydrogen atom or the like;
X and Y are each CH;
$R_3$ and $R_4$ are bonded to form an optionally substituted 5- to 8-membered ring and the like; and
W is $NR_5R_8$ ($R_5$ is a hydrogen atom and the like, and $R_8$ is optionally substituted alkyl and the like), or a salt thereof.

Patent document 5 describes the following compound.
A compound represented by the following formula:

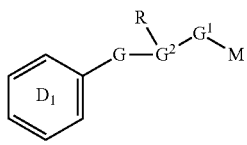

wherein Di is pyrimidine and the like;
G is void;
$G^2$ is phenyl and the like;
$G^1$ is $(CR^3R^{3a})uNR^3(CR^3R^{3a})w$ ($R^3$ is a hydrogen atom, $R^{3a}$ is $C_{1-4}$ alkyl and u+w=0-4); and
M is phenyl substituted by -Z-A-B (Z is $(CR^2R^{2a})qC(O)(CR^2R^{2a})q_1$, $q+q_1=0-2$, A is 5-12 heterocycle substituted by $R^4$ ($R^4$ is $C(O)R^{2c}$, $R^{2c}$ is OH and the like, and B is a hydrogen atom and the like, and the like,
or a salt thereof.

Patent document 6 describes the following compound.
A compound represented by the following formula:

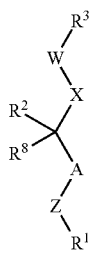

wherein $R^3$ is heterocyclocarbonyl optionally substituted by carboxyl and the like;
W is aryl and the like;
X is $-N(R^9)-$ ($R^9$ is a hydrogen atom);
$R^2$ and $R^8$ are each a hydrogen atom, alkyl and the like;
A is heteroaryl, $-C(O)-$ or $-C(O)NH-$;
Z is a bond and the like; and
$R^1$ is heteroaryl and the like,
or a salt thereof.

DOCUMENT LIST

Patent Documents patent document 1: WO 2009/057784
patent document 2: WO 2009/110520
patent document 3: WO 2011/027849
patent document 4: WO 2004/065351
patent document 5: WO 2002/000647
patent document 6: WO 2005/019167

SUMMARY OF THE INVENTION

Problems to be Solved by the Invention

The development of a compound useful for the prophylaxis or treatment of diabetes and the like and having superior efficacy has been desired.

Means of Solving the Problems

The present inventors found that a compound represented by the following formula (I) or a salt thereof (sometimes to be abbreviated as "compound (I)" in the present specification) has a superior glucagon receptor antagonistic action, and superior efficacy as a prophylactic or therapeutic agent for diabetes and the like. Based on this finding, the present inventors have conducted intensive studies and completed the present invention.

Accordingly, the present invention relates to
[1] a compound represented by the formula (I):

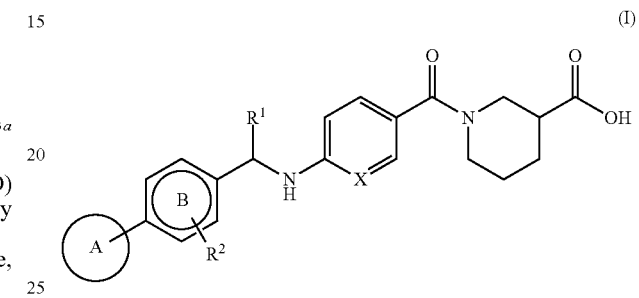

wherein ring A is an optionally further substituted 5- or 6-membered aromatic ring, and the 5- or 6-membered aromatic ring is optionally fused with an optionally substituted 5- to 7-membered ring;
ring B is an optionally further substituted 6-membered aromatic ring;
$R^1$ is $C_{1-6}$ alkyl optionally substituted by a halogen atom, or $C_{3-10}$ cycloalkyl optionally substituted by a halogen atom;
$R^2$ is a hydrogen atom, a halogen atom, or $C_{1-6}$ alkyl optionally substituted by a halogen atom; and
X is CH or N,
or a salt thereof;
[2] the compound of [1], wherein ring A is a benzene ring, a pyrrole ring, a pyrazole ring, an oxazole ring, an isoxazole ring, a triazole ring, a pyridine ring, a pyridazine ring, a pyrimidine ring or a pyrazine ring, each of which is optionally further substituted, or a salt thereof;
[3] the compound of [1] or [2], wherein ring B is a benzene ring or a pyridine ring, each of which is optionally further substituted by 1 to 3 $C_{1-6}$ alkyls, or a salt thereof;
[4] the compound of [1]-[3], wherein $R^1$ is $C_{1-6}$ alkyl or $C_{3-10}$ cycloalkyl, each of which is optionally substituted by 1 to 5 halogen atoms, or a salt thereof;
[5] the compound of [1]-[4], wherein $R^2$ is a hydrogen atom or $C_{1-6}$ alkyl optionally substituted by a halogen atom, or a salt thereof;
[6] the compound of [1]-[5], wherein X is CH, or a salt thereof;
[7] (3R)-1-(4-((1-(4-(5-chloropyrimidin-2-yl)-2-methylphenyl)-4,4,4-trifluorobutyl)amino)benzoyl)piperidine-3-carboxylic acid or a salt thereof;
[8] (3R)-1-(4-((4,4,4-trifluoro-1-(2-methyl-4-(5-(trifluoromethyl)pyrimidin-2-yl)phenyl)butyl)amino)benzoyl)piperidine-3-carboxylic acid or a salt thereof;
[9] (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylic acid or a salt thereof;
[10] a medicament comprising the compound of [1]-[9] or a salt thereof;
[11] the medicament of [10], which is a glucagon receptor antagonist;

[12] the medicament of [10], which is a glucose production inhibitor;
[13] the medicament of [10], which is a prophylactic or therapeutic agent for diabetes;
[14] a method for the prophylaxis or treatment of diabetes in a mammal, comprising administering an effective amount of the compound of [1]-[9] or a salt thereof to the mammal;
[15] a method of antagonizing a glucagon receptor in a mammal, comprising administering an effective amount of the compound of [1]-[9] or a salt thereof to the mammal;
[16] a method of suppressing glucose production in a mammal, comprising administering an effective amount of the compound of [1]-[9] or a salt thereof to the mammal;
[17] use of the compound of [1]-[9] or a salt thereof in the production of an agent for the prophylaxis or treatment of diabetes;
[18] use of the compound of [1]-[9] or a salt thereof for the production of a glucose production inhibitor;
[19] the compound of [1]-[9] or a salt thereof for use in the prophylaxis or treatment of diabetes;
[20] the compound of [1]-[9] or a salt thereof for use for the suppression of glucose production; and the like.

Effect of the Invention

Since compound (I) has a glucagon receptor antagonistic action and superior efficacy (suppression of blood glucose increase, hypoglycemic action and the like), it is useful for the prophylaxis or treatment of diabetes and the like.

DETAILED DESCRIPTION OF THE INVENTION

Unless otherwise specified, examples of the "halogen atom" in the present specification include a fluorine atom, a chlorine atom, a bromine atom, and an iodine atom.

Examples of the "$C_{1-6}$ alkyl" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

Examples of the "$C_{2-6}$ alkenyl" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

Examples of the "$C_{1-6}$ alkoxy" in the present specification include methoxy, ethoxy, propoxy, isopropoxy, butoxy, isobutoxy, sec-butoxy, tert-butoxy and the like.

Examples of the "$C_{2-6}$ alkenyloxy" in the present specification include ethenyloxy and the like.

Examples of the "$C_{3-10}$ cycloalkyl" in the present specification include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Examples of the "$C_{3-6}$ cycloalkyl" in the present specification include cyclopropyl, cyclobutyl, cyclopentyl, cyclohexyl and the like.

$C_{3-6}$ cycloalkyl or $C_{3-10}$ cycloalkyl may foam a fused ring group with a benzene ring, and examples of the fused ring group include indanyl and the like.

Examples of the "$C_{3-10}$ cycloalkenyl" in the present specification include cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl), cycloheptenyl (e.g., 2-cyclohepten-1-yl), cyclooctenyl (e.g., 2-cycloocten-1-yl) and the like.

$C_{3-10}$ cycloalkenyl may form a fused ring group with a benzene ring, and examples of the fused ring group include dihydronaphthyl and the like.

Examples of the "$C_{4-10}$ cycloalkadienyl" in the present specification include 2,4-cyclopentadien-1-yl, 2,4-cyclohexadien-1-yl, 2,5-cyclohexadien-1-yl and the like.

$C_{4-10}$ cycloalkadienyl may form a fused ring group with a benzene ring, and examples of the fused ring group include fluorenyl and the like.

Examples of the "$C_{6-14}$ aryl" in the present specification include phenyl, naphthyl, anthryl, phenanthryl, acenaphtylenyl, biphenylyl and the like.

Examples of the "$C_{6-14}$ aryloxy" in the present specification include phenyloxy and naphthyloxy.

Examples of the "$C_{7-13}$ aralkyl" in the present specification include benzyl, phenethyl, naphthylmethyl, biphenylylmethyl and the like.

Examples of the "$C_{7-13}$ aralkyloxy" in the present specification include benzyloxy and the like.

Examples of the "$C_{1-6}$ alkyl optionally substituted by a halogen atom" in the present specification include the above-mentioned "$C_{1-6}$ alkyl" optionally substituted by 1 to 5 of the above-mentioned "halogen atoms". When substituted by plural halogen atoms, respective halogen atoms may be the same or different.

Examples of the "$C_{3-10}$ cycloalkyl optionally substituted by a halogen atom" in the present specification include the above-mentioned "$C_{3-10}$ cycloalkyl" optionally substituted by 1 to 5 of the above-mentioned "halogen atoms". When substituted by plural halogen atoms, respective halogen atoms may be the same or different.

Examples of the "4- to 12-membered aromatic heterocyclic group" in the present specification include a 4- to 7-membered (preferably 5- or 6-membered) monocyclic aromatic heterocyclic group and a 8- to 12-membered fused aromatic heterocyclic group, each containing, as a ring-constituting atom besides carbon atom, 1 to 4 hetero atoms selected from an oxygen atom, a sulfur atom (the sulfur atom is optionally oxidized) and a nitrogen atom.

Examples of the fused aromatic heterocyclic group include a group induced from a ring wherein 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring, and a ring corresponding to the 4- to 7-membered monocyclic aromatic heterocyclic group are fused, and the like.

Preferable examples of the 4- to 12-membered aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3- triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

Examples of the "4- to 12-membered non-aromatic heterocyclic group" in the present specification include a O-5 to 7-membered (preferably 5- or 6-membered) monocyclic non-aromatic heterocyclic group and a 8- to 12-membered fused non-aromatic heterocyclic group, each containing, as a ring-constituting atom besides carbon atom, 1 to 4 hetero atoms selected from an oxygen atom, a sulfur atom (the sulfur atom is optionally oxidized) and a nitrogen atom.

Examples of the fused non-aromatic heterocyclic group include a group (which is optionally further saturated partially) induced from a ring wherein 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring, and a ring corresponding to the 4- to 7-membered monocyclic non-aromatic heterocyclic group are fused, and the like.

Preferable examples of the 4- to 12-membered non-aromatic heterocyclic group include
monocyclic non-aromatic heterocyclic groups such as oxetanyl (e.g., 3-oxetanyl), pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like;
fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like;
and the like.

Examples of the "5- or 6-membered aromatic ring" in the present specification include a benzene ring, a pyrrole ring, a pyrazole ring, an imidazole ring, a triazole ring (1,2,3-triazole ring, 1,2,4-triazole ring, 1,3,4-triazole ring), a tetrazole ring, an oxazole ring, an isoxazole ring, a thiazole ring, an isothiazole ring, an oxadiazole ring, a thiadiazole ring, a furan ring, a thiophene ring, a pyridine ring, a pyridazine ring, a pyrimidine ring, a pyrazine ring, a triazine ring and the like.

Examples of the "6-membered aromatic ring" in the present specification include a benzene ring, a pyridine ring, a pyridazine ring, a pyrimidine ring, a pyrazine ring, a triazine ring and the like.

Examples of the "5- to 7-membered ring" in the present specification include a cycloalkane ring corresponding to the 5- to 7-membered cycloalkyl of the above-mentioned "$C_{3-10}$ cycloalkyl", a cycloalkene ring corresponding to the 5- to 7-membered cycloalkenyl of the above-mentioned "$C_{3-10}$ cycloalkenyl", a cycloalkadiene ring corresponding to the 5- to 7-membered cycloalkadienyl of the above-mentioned "$C_{4-10}$ cycloalkadienyl", a benzene ring, an aromatic heterocycle corresponding to the 5- to 7-membered aromatic heterocyclic group of the above-mentioned "4- to 12-membered aromatic heterocyclic group", a non-aromatic heterocycle corresponding to the 5- to 7-membered non-aromatic heterocyclic group of the above-mentioned "4- to 12-membered non-aromatic heterocyclic group" and the like.

Examples of the "4- to 12-membered aromatic heterocyclyl-oxy" in the present specification include a group wherein oxy is bonded to the above-mentioned 4- to 12-membered aromatic heterocyclic group, such as pyridyloxy and the like.

Examples of the "4- to 12-membered non-aromatic heterocyclyl-oxy" in the present specification include a group wherein oxy is bonded to the above-mentioned 4- to 12-membered non-aromatic heterocyclic group, such as tetrahydropyranyloxy, tetrahydrothiopyranyloxy, 1,1-dioxidotetrahydrothiopyranyloxy and the like.

Examples of the "4- to 12-membered aromatic heterocyclyl-carbonyl" in the present specification include a group wherein carbonyl is bonded to the above-mentioned 4- to 12-membered aromatic heterocyclic group, such as furylcarbonyl, thienylcarbonyl, pyrazolylcarbonyl, pyrazinylcarbonyl, isooxazolylcarbonyl, pyridylcarbonyl, thiazolylcarbonyl and the like.

Examples of the "4- to 12-membered non-aromatic heterocyclyl-carbonyl" in the present specification include a group wherein carbonyl is bonded to the above-mentioned 4- to 12-membered non-aromatic heterocyclic group, such as tetrahydrofurylcarbonyl, pyrrolidinylcarbonyl, morpholinylcarbonyl and the like.

Examples of the "$C_{1-6}$ alkyl-carbonyl" in the present specification include acetyl, propanoyl, butanoyl, isobutanoyl, tert-butanoyl, pentanoyl, isopentanoyl, hexanoyl and the like.

Examples of the "$C_{1-6}$ alkyl-carbonyloxy" in the present specification include acetyloxy, propanoyloxy, butanoyloxy, isobutanoyloxy, tert-butanoyloxy, pentanoyloxy, isopentanoyloxy, hexanoyloxy and the like.

Examples of the "$C_{1-6}$ alkylcarbonylamino" in the present specification include methylcarbonylamino, ethylcarbonylamino and the like.

Examples of the "$C_{1-6}$ alkylsulfonylamino" in the present specification include methylsulfonylamino, ethylsulfonylamino and the like.

Examples of the "$C_{1-6}$ alkylaminosulfonyl" in the present specification include tert-butylaminosulfonyl and the like.

Examples of the "$C_{1-6}$ alkoxy-carbonyl" in the present specification include methoxycarbonyl, ethoxycarbonyl, propoxycarbonyl, tert-butoxycarbonyl and the like.

Examples of the "$C_{6-14}$ aryl-carbonyl" in the present specification include benzoyl and the like.

Examples of the "$C_{1-6}$ alkylthio" in the present specification include methylthio, ethylthio, isopropylthio and the like.

Examples of the "$C_{6-14}$ arylthio" in the present specification include phenylthio, naphthylthio and the like.

Examples of the "$C_{7-13}$ aralkylthio" in the present specification include benzylthio and the like.

Examples of the "$C_{1-6}$ alkylsulfonyl" in the present specification include methylsulfonyl, ethylsulfonyl, isopropylsulfonyl and the like.

Examples of the "$C_{6-14}$ arylsulfonyl" in the present specification include benzenesulfonyl and the like.

Examples of the "$C_{1-3}$ alkylenedioxy" in the present specification include methylenedioxy, ethylenedioxy and the like.

The 5- or 6-membered aromatic ring, 6-membered aromatic ring and 5- to 7-membered ring of the "optionally further substituted 5- or 6-membered aromatic ring", "optionally further substituted 6-membered aromatic ring" and "optionally substituted 5- to 7-membered ring" in the present specification optionally have 1 to 5 (preferably 1 to 3) substituents at substitutable position(s). Examples of such substituent include the following substituent group A. When the number of the substituents is two or more, the respective substituents may be the same or different.

(Substituent Group a)
(1) $C_{3-10}$ cycloalkyl;
(2) $C_{6-14}$ aryl optionally substituted by 1 to 3 substituents selected from
    (a) $C_{1-6}$ alkyl optionally substituted by 1 to 3 halogen atoms,
    (b) hydroxy,
    (c) $C_{1-6}$ alkoxy optionally substituted by 1 to 3 halogen atoms, and
    (d) a halogen atom;
(3) a 4- to 12-membered aromatic heterocyclic group optionally substituted by 1 to 3 substituents selected from
    (a) $C_{1-6}$ alkyl optionally substituted by 1 to 3 halogen atoms,
    (b) hydroxy,
    (c) $C_{1-6}$ alkoxy optionally substituted by 1 to 3 halogen atoms, and
    (d) a halogen atom;
(4) a 4- to 12-membered non-aromatic heterocyclic group optionally substituted by 1 to 3 substituents selected from
    (a) $C_{1-6}$ alkyl optionally substituted by 1 to 3 halogen atoms,
    (b) hydroxy,
    (c) $C_{1-6}$ alkoxy optionally substituted by 1 to 3 halogen atoms,
    (d) a halogen atom, and
    (e) oxo;
(5) amino optionally mono- or di-substituted by substituent(s) selected from
    (a) $C_{1-6}$ alkyl optionally substituted by 1 to 3 substituents selected from
        (i) a halogen atom, and
        (ii) $C_{1-6}$ alkoxy,
    (b) $C_{1-6}$ alkyl-carbonyl optionally substituted by 1 to 3 halogen atoms,
    (c) $C_{1-6}$ alkoxy-carbonyl optionally substituted by 1 to 3 halogen atoms,
    (d) $C_{1-6}$ alkylsulfonyl optionally substituted by 1 to 3 halogen atoms,
    (e) carbamoyl optionally mono- or di-substituted by $C_{1-6}$ alkyl optionally substituted by 1 to 3 halogen atoms,
    (f) 4- to 12-membered aromatic heterocyclic group,
    (g) $C_{6-14}$ aryl-carbonyl (e.g., benzoyl),
    (h) $C_{6-14}$ arylsulfonyl (e.g., benzenesulfonyl), and
    (i) $C_{7-13}$ aralkyl (e.g., benzyl);
(6) $C_{1-6}$ alkyl-carbonyl optionally substituted by 1 to 3 halogen atoms;
(7) $C_{1-6}$ alkoxy-carbonyl optionally substituted by 1 to 3 substituents selected from
    (a) a halogen atom,
    (b) $C_{1-6}$ alkoxy, and
    (c) $C_{6-14}$ aryl;
(8) $C_{1-6}$ alkylsulfonyl optionally substituted by 1 to 3 halogen atoms;
(9) carbamoyl optionally mono- or di-substituted by $O_{1-6}$ alkyl optionally substituted by 1 to 3 substituents selected from
    (a) a halogen atom, and
    (b) cyano;
(10) thiocarbamoyl optionally mono- or di-substituted by $C_{1-6}$ alkyl optionally substituted by 1 to 3 halogen atoms;
(11) sulfamoyl optionally mono- or di-substituted by $C_{1-6}$ alkyl optionally substituted by 1 to 3 halogen atoms;
(12) carboxy;
(13) hydroxy;
(14) $C_{1-6}$ alkoxy optionally substituted by 1 to 3 substituents selected from
    (a) a halogen atom,
    (b) carboxy,
    (c) $C_{1-6}$ alkoxy,
    (d) $C_{3-6}$ cycloalkyl,
    (e) $C_{1-6}$ alkoxy-carbonyl optionally substituted by 1 to 3 $C_{6-14}$ aryls,
    (f) amino optionally mono- or di-substituted by substituent(s) selected from $C_{1-6}$ alkyl and $C_{1-6}$ alkoxy-carbonyl,
    (g) a 4- to 12-membered aromatic heterocyclic group optionally substituted by 1 to 3 substituents selected from
        (i) a halogen atom, and
        (ii) $C_{1-6}$ alkyl,
    (h) a 4- to 12-membered non-aromatic heterocyclic group optionally substituted by 1 to 3 $C_{1-6}$ alkyls,
    (i) $C_{1-6}$ alkylsulfonyl,
    (j) $C_{1-6}$ alkylthio, and
    (k) hydroxy;

(15) $C_{2-6}$ alkenyloxy optionally substituted by 1 to 3 halogen atoms;
(16) $C_{7-13}$ aralkyloxy;
(17) $C_{6-14}$ aryloxy;
(18) $C_{1-6}$ alkyl-carbonyloxy;
(19) 4- to 12-membered aromatic heterocyclyl-oxy optionally substituted by 1 to 3 substituents selected from
  (i) $C_{1-6}$ alkyl optionally substituted by 1 to 3 halogen atoms, and
  (ii) cyano;
(20) 4- to 12-membered non-aromatic heterocyclyl-oxy;
(21) $C_{6-14}$ aryl-carbonyl optionally substituted by 1 to 3 substituents selected from
  (a) a halogen atom, and
  (b) $C_{1-6}$ alkyl optionally substituted by 1 to 3 halogen atoms;
(22) 4- to 12-membered aromatic heterocyclyl-carbonyl optionally substituted by 1 to 3 substituents selected from $C_{1-6}$ alkyl optionally substituted by 1 to 3 halogen atoms;
(23) 4- to 12-membered non-aromatic heterocyclyl-carbonyl optionally substituted by 1 to 3 substituents selected from $C_{1-6}$ alkyl optionally substituted by 1 to 3 halogen atoms;
(24) mercapto;
(25) $C_{1-6}$ alkylthio optionally substituted by 1 to 3 substituents selected from
  (a) a halogen atom, and
  (b) $C_{1-6}$ alkoxy-carbonyl;
(26) $C_{7-13}$ aralkylthio;
(27) $C_{6-14}$ arylthio;
(28) cyano;
(29) nitro;
(30) a halogen atom;
(31) $C_{1-3}$ alkylenedioxy;
(32) $C_{1-6}$ alkyl optionally substituted by 1 to 3 substituents selected from
  (a) a halogen atom,
  (b) carboxy,
  (c) hydroxy,
  (d) $C_{1-6}$ alkoxy-carbonyl,
  (e) $C_{1-6}$ alkoxy optionally substituted by 1 to 3 $C_{1-6}$ alkoxys,
  (f) amino optionally mono- or di-substituted by $C_{1-6}$ alkyl,
  (g) cyano, and
  (h) $C_{1-6}$ alkylsulfonylamino;
(33) $C_{2-6}$ alkenyl optionally substituted by 1 to 3 substituents selected from
  (a) a halogen atom,
  (b) carboxy,
  (c) hydroxy,
  (d) $C_{1-6}$ alkoxy-carbonyl,
  (e) $C_{1-6}$ alkoxy, and
  (f) amino optionally mono- or di-substituted by $C_{1-6}$ alkyl; and
(34) $C_{7-13}$ aralkyl optionally substituted by 1 to 3 substituents selected from
  (a) $C_{1-6}$ alkyl optionally substituted by 1 to 3 halogen atoms,
  (b) hydroxy,
  (c) $C_{1-6}$ alkoxy, and
  (d) a halogen atom.

When the number of the substituents is two or more, the respective substituents may be the same or different.

Compound (I) is explained below.

Ring A is an optionally further substituted 5- or 6-membered aromatic ring, and the 5- or 6-membered aromatic ring is optionally fused with an optionally substituted 5- to 7-membered ring.

As the "5- or 6-membered aromatic ring" of the "optionally further substituted 5- or 6-membered aromatic ring" for ring A, a benzene ring, a pyrrole ring, a pyrazole ring, an oxazole ring, an isoxazole ring, a triazole ring, a pyridine ring, a pyridazine ring, a pyrimidine ring, a pyrazine ring and the like are preferable, and a pyridine ring and a pyrimidine ring are more preferable.

The "5- or 6-membered aromatic ring" is optionally further substituted by 1-4 (preferably 1-3, more preferably 1 or 2) substituents other than ring B at substitutable position(s).

As such substituent,
(1) a halogen atom (e.g., fluorine atom, chlorine atom),
(2) $C_{1-6}$ alkyl (e.g., methyl, ethyl, isopropyl, tert-butyl) optionally substituted by 1 to 3 substituents selected from
  (i) a halogen atom (e.g., fluorine atom),
  (ii) cyano, and
  (iii) $C_{1-6}$ alkylsulfonylamino (e.g., methylsulfonylamino),
(3) $C_{1-6}$ alkoxy (e.g., methoxy, ethoxy, isopropoxy, isobutoxy) optionally substituted by 1 to 3 substituents selected from
  (i) a halogen atom (e.g., fluorine atom), and
  (ii) $C_{3-10}$ cycloalkyl (e.g., cyclopropyl),
(4) cyano,
(5) carbamoyl optionally substituted by $C_{1-6}$ alkyl (e.g., ethyl) optionally substituted by cyano,
(6) $C_{1-6}$ alkylcarbonylamino (e.g., methylcarbonylamino),
(7) $C_{1-6}$ alkylsulfonyl (e.g., methylsulfonyl),
(8) $C_{1-6}$ alkylaminosulfonyl (e.g., tert-butylaminosulfonyl),
(9) $C_{1-6}$ alkylsulfonylamino (e.g., methylsulfonylamino),
(10) $C_{3-10}$ cycloalkyl (e.g., cyclopropyl),
(11) 4- to 12-membered non-aromatic heterocyclyl-oxy (e.g., tetrahydropyranyloxy),
(12) 4- to 12-membered non-aromatic heterocyclic group (e.g., pyrrolidinyl, morpholino),
(13) $C_{6-14}$ aryl (e.g., phenyl) optionally substituted by 1 to 3 halogen atoms (e.g., fluorine atom)
and the like are preferable.

As the "5- to 7-membered ring" of the "optionally substituted 5- to 7-membered ring" that may be fused with the "5- or 6-membered aromatic ring", a cyclohexane ring, a cyclohexene ring, a cyclohexadiene ring, a morpholine ring and the like are preferable.

The "5- to 7-membered ring" is optionally substituted by 1-4 (preferably 1-3, more preferably 1 or 2) substituents at substitutable position(s). As such substituent, a halogen atom (e.g., fluorine atom), $C_{1-6}$ alkyl (e.g., methyl) and the like are preferable.

Ring A is preferably a benzene ring, a pyrrole ring, a pyrazole ring, an oxazole ring, an isoxazole ring, a triazole ring, a pyridine ring, a pyridazine ring, a pyrimidine ring or a pyrazine ring, each of which is optionally further substituted; more preferably a benzene ring, a pyrrole ring, a pyrazole ring, an oxazole ring, an isoxazole ring, a triazole ring, a pyridine ring, a pyridazine ring, a pyrimidine ring or a pyrazine ring, each optionally further substituted by 1-4 (preferably 1-3, more preferably 1 or 2) substituents selected from
(1) a halogen atom (e.g., fluorine atom, chlorine atom),
(2) $C_{1-6}$ alkyl (e.g., methyl, ethyl, isopropyl, tert-butyl) optionally substituted by 1 to 3 substituents selected from
  (i) a halogen atom (e.g., fluorine atom),
  (ii) cyano, and
  (iii) $C_{1-6}$ alkylsulfonylamino (e.g., methylsulfonylamino),
(3) $C_{1-6}$ alkoxy (e.g., methoxy, ethoxy, isopropoxy, isobutoxy) optionally substituted by 1 to 3 substituents selected from
  (i) a halogen atom (e.g., fluorine atom), and
  (ii) $C_{3-10}$ cycloalkyl (e.g., cyclopropyl), (4) cyano,
(5) carbamoyl optionally substituted by $C_{1-6}$ alkyl (e.g., ethyl) optionally substituted by cyano,
(6) $C_{1-6}$ alkylcarbonylamino (e.g., methylcarbonylamino),
(7) $C_{1-6}$ alkylsulfonyl (e.g., methylsulfonyl),
(8) $C_{1-6}$ alkylaminosulfonyl (e.g., tert-butylaminosulfonyl),
(9) $C_{1-6}$ alkylsulfonylamino (e.g., methylsulfonylamino),
(10) $C_{3-10}$ cycloalkyl (e.g., cyclopropyl),
(11) 4- to 12-membered non-aromatic heterocyclyl-oxy (e.g., tetrahydropyranyloxy),
(12) 4- to 12-membered non-aromatic heterocyclic group (e.g., pyrrolidinyl, morpholino), and
(13) $C_{6-14}$ aryl (e.g., phenyl) optionally substituted by 1 to 3 halogen atoms (e.g., fluorine atom).

Ring A is more preferably
(A) a benzene ring optionally further substituted by 1-4 (preferably 1-3, more preferably 1 or 2) substituents selected from
   (1) a halogen atom (e.g., fluorine atom, chlorine atom),
   (2) $C_{1-6}$ alkyl (e.g., methyl, tert-butyl) optionally substituted by 1 to 3 substituents selected from
      (i) a halogen atom (e.g., fluorine atom),
      (ii) cyano, and
      (iii) $C_{1-6}$ alkylsulfonylamino (e.g., methylsulfonylamino),
   (3) $C_{1-6}$ alkoxy (e.g., methoxy, isopropoxy, isobutoxy) optionally substituted by 1 to 3 halogen atoms (e.g., fluorine atom),
   (4) cyano,
   (5) carbamoyl optionally substituted by $C_{1-6}$ alkyl (e.g., ethyl) optionally substituted by cyano,
   (6) $C_{1-6}$ alkylcarbonylamino (e.g., methylcarbonylamino),
   (7) $C_{1-6}$ alkylsulfonyl (e.g., methylsulfonyl),
   (8) $C_{1-6}$ alkylaminosulfonyl (e.g., tert-butylaminosulfonyl), and
   (9) $C_{1-6}$ alkylsulfonylamino (e.g., methylsulfonylamino),
(B) a pyrrole ring optionally further substituted by 1 to 3 $C_{1-6}$ alkyls (e.g., methyl),
(C) a pyrazole ring optionally further substituted by 1-4 (preferably 1-3, more preferably 1 or 2) substituents selected from
   (1) $C_{1-6}$ alkyl (e.g., methyl, ethyl, isopropyl, tert-butyl) optionally substituted by 1 to 3 halogen atoms (e.g., fluorine atom),
   (2) $C_{3-10}$ cycloalkyl (e.g., cyclopropyl), and
   (3) $C_{6-14}$ aryl (e.g., phenyl) optionally substituted by 1 to 3 halogen atoms (e.g., fluorine atom),
(D) an oxazole ring optionally further substituted by 1 to 3 $C_{1-6}$ alkyls (e.g., isopropyl, tert-butyl),
(E) an isoxazole ring optionally further substituted by 1 to 3 $C_{1-6}$ alkyls (e.g., methyl),
(F) a triazole ring optionally further substituted by 1 to 3 $C_{1-6}$ alkyls (e.g., tert-butyl),
(G) a pyridine ring optionally further substituted by 1-4 (preferably 1-3, more preferably 1 or 2) substituents selected from
   (1) a halogen atom (e.g., fluorine atom, chlorine atom),
   (2) $C_{1-6}$ alkyl (e.g., methyl, ethyl) optionally substituted by 1 to 3 halogen atoms (e.g., fluorine atom),
   (3) $C_{1-6}$ alkoxy (e.g., methoxy, ethoxy, isopropoxy) optionally substituted by 1 to 3 substituents selected from
      (i) a halogen atom (e.g., fluorine atom), and
      (ii) $C_{3-10}$ cycloalkyl (e.g., cyclopropyl),
   (4) $C_{3-10}$ cycloalkyl (e.g., cyclopropyl),
   (5) 4- to 12-membered non-aromatic heterocyclyl-oxy (e.g., tetrahydropyranyloxy), and
   (6) 4- to 12-membered non-aromatic heterocyclic group (e.g., pyrrolidinyl, morpholino),
(H) a pyridazine ring optionally further substituted by $C_{1-6}$ alkyl (e.g., methyl) optionally substituted by 1 to 3 halogen atoms (e.g., fluorine atom),
(I) a pyrimidine ring optionally further substituted by 1-4 (preferably 1-3, more preferably 1 or 2) substituents selected from
   (1) a halogen atom (e.g., chlorine atom),
   (2) $C_{1-6}$ alkyl (e.g., methyl, ethyl) optionally substituted by 1 to 3 halogen atoms (e.g., fluorine atom), and
   (3) $C_{1-6}$ alkoxy (e.g., ethoxy), or
(J) a pyrazine ring optionally further substituted by $C_{1-6}$ alkyl (e.g., methyl) optionally substituted by 1 to 3 halogen atoms (e.g., fluorine atom).

Ring A is particularly preferably
(A) a pyridine ring optionally further substituted by 1-4 (preferably 1-3, more preferably 1 or 2) substituents selected from
   (1) a halogen atom (e.g., fluorine atom, chlorine atom),
   (2) $C_{1-6}$ alkyl (e.g., methyl, ethyl) optionally substituted by 1 to 3 halogen atoms (e.g., fluorine atom),
   (3) $C_{1-6}$ alkoxy (e.g., methoxy, ethoxy, isopropoxy) optionally substituted by 1 to 3 substituents selected from (i) a halogen atom (e.g., fluorine atom), and
      (ii) $C_{3-10}$ cycloalkyl (e.g., cyclopropyl),
   (4) $C_{3-10}$ cycloalkyl (e.g., cyclopropyl),
   (5) 4- to 12-membered non-aromatic heterocyclyl-oxy (e.g., tetrahydropyranyloxy), and
   (6) 4- to 12-membered non-aromatic heterocyclic group (e.g., pyrrolidinyl, morpholino), or
(B) a pyrimidine ring optionally further substituted by 1-4 (preferably 1-3, more preferably 1 or 2) substituents selected from
   (1) a halogen atom (e.g., chlorine atom),
   (2) $C_{1-6}$ alkyl (e.g., methyl, ethyl) optionally substituted by 1 to 3 halogen atoms (e.g., fluorine atom), and
   (3) $C_{1-6}$ alkoxy (e.g., ethoxy).

In another embodiment, ring A is preferably a pyrazole ring, an oxazole ring or a pyridine ring, each of which is fused with an optionally substituted 5- to 7-membered ring; more preferably a pyrazole ring, an oxazole ring or a pyridine ring, each of which is fused with an optionally substituted cyclohexane ring, an optionally substituted cyclohexene ring, an optionally substituted cyclohexadiene ring or an optionally substituted morpholine ring; further preferably
(A)(1) a pyrazole ring fused with a cyclohexane ring optionally substituted by 1 to 3 halogen atoms (e.g., fluorine atom), or
(2) a pyrazole ring fused with a cyclohexadiene ring optionally substituted by 1 to 3 halogen atoms (e.g., fluorine atom),
(B) an oxazole ring fused with a cyclohexene ring, or
(C) a pyridine ring fused with a morpholine ring optionally substituted by 1 to 3 $C_{1-6}$ alkyls (e.g., methyl).

In another embodiment, ring A is particularly preferably a pyrazole ring fused with a cyclohexane ring optionally substituted by 1 to 3 halogen atoms (e.g., fluorine atom).

Ring B is an optionally further substituted 6-membered aromatic ring.

As the "6-membered aromatic ring" of the "optionally further substituted 6-membered aromatic ring" for ring B, a benzene ring, a pyridine ring and the like are preferable and a benzene ring is further preferable.

The "6-membered aromatic ring" is optionally further substituted by 1-3 (preferably 1-2, more preferably 1) substituents other than ring A, —$CHR^1$—NH— and $R^2$, at substitutable position(s).

As such substituent, $C_{1-6}$ alkyl (e.g., methyl) and the like are preferable.

Ring B is preferably a benzene ring or a pyridine ring, each of which is optionally further substituted by 1-3 (preferably 1-2, more preferably 1) $C_{1-6}$ alkyl (e.g., methyl); more preferably (A) a benzene ring optionally further substituted by 1-3 (preferably 1-2, more preferably 1) $C_{1-6}$ alkyl (e.g., methyl) or (B) a pyridine ring; further preferably a benzene ring or a pyridine ring.

Ring B is particularly preferably a benzene ring.

$R^1$ is $C_{1-6}$ alkyl optionally substituted by a halogen atom, or $C_{3-10}$ cycloalkyl optionally substituted by a halogen atom.

The "$C_{1-6}$ alkyl" of the "$C_{1-6}$ alkyl optionally substituted by a halogen atom" for $R^1$ is preferably propyl or isopropyl.

The "$C_{3-10}$ cycloalkyl" of the "$C_{3-10}$ cycloalkyl optionally substituted by a halogen atom" for $R^1$ is preferably cyclohexyl.

$R^1$ is preferably $C_{1-6}$ alkyl (e.g., propyl, isopropyl) or $C_{3-10}$ cycloalkyl (e.g., cyclohexyl), each of which is optionally substituted by 1 to 5 (e.g., 1 to 3) halogen atoms (e.g., fluorine atom); more preferably (A) $C_{1-6}$ alkyl (e.g., propyl, isopropyl) optionally substituted by 1 to 3 halogen atoms (e.g., fluorine atom), or (B) $C_{3-10}$ cycloalkyl (e.g., cyclohexyl); further preferably $C_{1-6}$ alkyl (e.g., propyl, isopropyl) optionally substituted by 1 to 3 halogen atoms (e.g., fluorine atom).

$R^2$ is a hydrogen atom, a halogen atom, or $C_{1-6}$ alkyl optionally substituted by a halogen atom.

The "$C_{1-6}$ alkyl" of the "$C_{1-6}$ alkyl optionally substituted by a halogen atom" for $R^2$ is preferably methyl.

$R^2$ is preferably a hydrogen atom or $C_{1-6}$ alkyl (e.g., methyl) optionally substituted by a halogen atom, more preferably a hydrogen atom or $C_{1-6}$ alkyl (e.g., methyl), further preferably $C_{1-6}$ alkyl (e.g., methyl).

X is CH or N.

X is preferably CH.

Preferable examples of compound (I) include the following compounds.

[Compound I-1]
Compound (I) wherein
ring A is a benzene ring, a pyrrole ring, a pyrazole ring, an oxazole ring, an isoxazole ring, a triazole ring, a pyridine ring, a pyridazine ring, a pyrimidine ring or a pyrazine ring, each of which is optionally further substituted;
ring B is a benzene ring or a pyridine ring, each of which is optionally further substituted by 1-3 (preferably 1-2, more preferably 1) $C_{1-6}$ alkyl (e.g., methyl);
$R^1$ is $C_{1-6}$ alkyl (e.g., propyl, isopropyl) or $C_{3-10}$ cycloalkyl (e.g., cyclohexyl), each of which is optionally substituted by 1 to 5 (e.g., 1 to 3) halogen atoms (e.g., fluorine atom);
$R^2$ is a hydrogen atom or $C_{1-6}$ alkyl (e.g., methyl) optionally substituted by a halogen atom; and
X is CH or N.

[Compound 1-2]
Compound (I) wherein
ring A is a benzene ring, a pyrrole ring, a pyrazole ring, an oxazole ring, an isoxazole ring, a triazole ring, a pyridine ring, a pyridazine ring, a pyrimidine ring or a pyrazine ring, each optionally further substituted by 1-4 (preferably 1-3, more preferably 1 or 2) substituents selected from
(1) a halogen atom (e.g., fluorine atom, chlorine atom),
(2) $C_{1-6}$ alkyl (e.g., methyl, ethyl, isopropyl, tert-butyl) optionally substituted by 1 to 3 substituents selected from
   (i) a halogen atom (e.g., fluorine atom),
   (ii) cyano, and
   (iii) $C_{1-6}$ alkylsulfonylamino (e.g., methylsulfonylamino),
(3) $C_{1-6}$ alkoxy (e.g., methoxy, ethoxy, isopropoxy, isobutoxy) optionally substituted by 1 to 3 substituents selected from
   (i) a halogen atom (e.g., fluorine atom), and
   (ii) $C_{3-10}$ cycloalkyl (e.g., cyclopropyl),
(4) cyano,
(5) carbamoyl optionally substituted by $C_{1-6}$ alkyl (e.g., ethyl) optionally substituted by cyano,
(6) $C_{1-6}$ alkylcarbonylamino (e.g., methylcarbonylamino),
(7) $C_{1-6}$ alkylsulfonyl (e.g., methylsulfonyl),
(8) $C_{1-6}$ alkylaminosulfonyl (e.g., tert-butylaminosulfonyl),
(9) $C_{1-6}$ alkylsulfonylamino (e.g., methylsulfonylamino),
(10) $C_{3-10}$ cycloalkyl (e.g., cyclopropyl),
(11) 4- to 12-membered non-aromatic heterocyclyl-oxy (e.g., tetrahydropyranyloxy),
(12) 4- to 12-membered non-aromatic heterocyclic group (e.g., pyrrolidinyl, morpholino), and
(13) $C_{6-14}$ aryl (e.g., phenyl) optionally substituted by 1 to 3 halogen atoms (e.g., fluorine atom);
ring B is (A) a benzene ring optionally further substituted by 1-3 (preferably 1-2, more preferably 1) $C_{1-6}$ alkyl (e.g., methyl) or (B) a pyridine ring;
$R^1$ is (A) $C_{1-6}$ alkyl (e.g., propyl, isopropyl) optionally substituted by 1 to 3 halogen atoms (e.g., fluorine atom) or (B) $C_{1-10}$ cycloalkyl (e.g., cyclohexyl);
$R^2$ is a hydrogen atom or $C_{1-6}$ alkyl (e.g., methyl); and
X is CH or N.

[Compound 1-3]
Compound (I) wherein
ring A is
(A) a benzene ring optionally further substituted by 1-4 (preferably 1-3, more preferably 1 or 2) substituents selected from
(1) a halogen atom (e.g., fluorine atom, chlorine atom),
(2) $C_{1-6}$ alkyl (e.g., methyl, tert-butyl) optionally substituted by 1 to 3 substituents selected from
   (i) a halogen atom (e.g., fluorine atom),
   (ii) cyano, and
   (iii) $C_{1-6}$ alkylsulfonylamino (e.g., methylsulfonylamino),
(3) $C_{1-6}$ alkoxy (e.g., methoxy, isopropoxy, isobutoxy) optionally substituted by 1 to 3 halogen atoms (e.g., fluorine atom),
(4) cyano,
(5) carbamoyl optionally substituted by $C_{1-6}$ alkyl (e.g., ethyl) optionally substituted by cyano,
(6) $C_{1-6}$ alkylcarbonylamino (e.g., methylcarbonylamino),
(7) $C_{1-6}$ alkylsulfonyl (e.g., methylsulfonyl),
(8) $C_{1-6}$ alkylaminosulfonyl (e.g., tert-butylaminosulfonyl), and
(9) $C_{1-6}$ alkylsulfonylamino (e.g., methylsulfonylamino),
(B) a pyrrole ring optionally further substituted by 1 to 3 $C_{1-6}$ alkyls (e.g., methyl),
(C) a pyrazole ring optionally further substituted by 1-4 (preferably 1-3, more preferably 1 or 2) substituents selected from
(1) $C_{1-6}$ alkyl (e.g., methyl, ethyl, isopropyl, tert-butyl) optionally substituted by 1 to 3 halogen atoms (e.g., fluorine atom),
(2) $C_{3-10}$ cycloalkyl (e.g., cyclopropyl), and
(3) $C_{6-14}$ aryl (e.g., phenyl) optionally substituted by 1 to 3 halogen atoms (e.g., fluorine atom),
(D) an oxazole ring optionally further substituted by 1 to 3 $C_{1-6}$ alkyls (e.g., isopropyl, tert-butyl),
(E) an isoxazole ring optionally further substituted by 1 to 3 $C_{1-6}$ alkyls (e.g., methyl),
(F) a triazole ring optionally further substituted by 1 to 3 $C_{1-6}$ alkyls (e.g., tert-butyl), (G) a pyridine ring optionally further substituted by 1-4 (preferably 1-3, more preferably 1 or 2) substituents selected from
  (1) a halogen atom (e.g., fluorine atom, chlorine atom),
  (2) $C_{1-6}$ alkyl (e.g., methyl, ethyl) optionally substituted by 1 to 3 halogen atoms (e.g., fluorine atom),
  (3) $C_{1-6}$ alkoxy (e.g., methoxy, ethoxy, isopropoxy) optionally substituted by 1 to 3 substituents selected from (i) a halogen atom (e.g., fluorine atom), and
  (ii) $C_{3-10}$ cycloalkyl (e.g., cyclopropyl),
  (4) $C_{3-10}$ cycloalkyl (e.g., cyclopropyl),
  (5) 4- to 12-membered non-aromatic heterocyclyl-oxy (e.g., tetrahydropyranyloxy), and
  (6) 4- to 12-membered non-aromatic heterocyclic group (e.g., pyrrolidinyl, morpholino),
(H) a pyridazine ring optionally further substituted by $C_{1-6}$ alkyl (e.g., methyl) optionally substituted by 1 to 3 halogen atoms (e.g., fluorine atom),
(I) a pyrimidine ring optionally further substituted by 1-4 (preferably 1-3, more preferably 1 or 2) substituents selected from
  (1) a halogen atom (e.g., chlorine atom),
  (2) $C_{1-6}$ alkyl (e.g., methyl, ethyl) optionally substituted by 1 to 3 halogen atoms (e.g., fluorine atom), and
  (3) $C_{1-6}$ alkoxy (e.g., ethoxy), or
(J) a pyrazine ring optionally further substituted by $C_{1-6}$ alkyl (e.g., methyl) optionally substituted by 1 to 3 halogen atoms (e.g., fluorine atom);
ring B is a benzene ring or a pyridine ring (preferably a benzene ring);
$R^1$ is $C_{1-6}$ alkyl (e.g., propyl, isopropyl) optionally substituted by 1 to 3 halogen atoms (e.g., fluorine atom);
$R^2$ is $C_{1-6}$ alkyl (e.g., methyl); and
X is CH or N (preferably CH).

[Compound 1-4]
Compound (I) wherein
ring A is
(A) a pyridine ring optionally further substituted by 1-4 (preferably 1-3, more preferably 1 or 2) substituents selected from
  (1) a halogen atom (e.g., fluorine atom, chlorine atom),
  (2) $C_{1-6}$ alkyl (e.g., methyl, ethyl) optionally substituted by 1 to 3 halogen atoms (e.g., fluorine atom),
  (3) $C_{1-6}$ alkoxy (e.g., methoxy, ethoxy, isopropoxy) optionally substituted by 1 to 3 substituents selected from
  (i) a halogen atom (e.g., fluorine atom), and
  (ii) $C_{3-10}$ cycloalkyl (e.g., cyclopropyl),
  (4) $C_{3-10}$ cycloalkyl (e.g., cyclopropyl),
  (5) 4- to 12-membered non-aromatic heterocyclyl-oxy (e.g., tetrahydropyranyloxy), and
  (6) 4- to 12-membered non-aromatic heterocyclic group (e.g., pyrrolidinyl, morpholino), or
(B) a pyrimidine ring optionally further substituted by 1-4 (preferably 1-3, more preferably 1 or 2) substituents selected from
  (1) a halogen atom (e.g., chlorine atom),
  (2) $C_{1-6}$ alkyl (e.g., methyl, ethyl) optionally substituted by 1 to 3 halogen atoms (e.g., fluorine atom), and
  (3) $C_{1-6}$ alkoxy (e.g., ethoxy);
ring B is a benzene ring;
$R^1$ is $C_{1-6}$ alkyl (e.g., propyl, isopropyl) optionally substituted by 1 to 3 halogen atoms (e.g., fluorine atom);
$R^2$ is $C_{1-6}$ alkyl (e.g., methyl); and
X is CH.

In another embodiment, preferable examples of compound (I) include the following compounds.

[Compound I-A]
Compound (I) wherein
ring A is a pyrazole ring, an oxazole ring or a pyridine ring, each of which is fused with an optionally substituted cyclohexane ring, an optionally substituted cyclohexene ring, an optionally substituted cyclohexadiene ring or an optionally substituted morpholine ring;
ring B is a benzene ring optionally further substituted by 1-3 (preferably 1-2, more preferably 1) $C_{1-6}$ alkyl (e.g., methyl);
$R^1$ is $C_{1-6}$ alkyl (e.g., propyl) optionally substituted by 1 to 3 halogen atoms (e.g., fluorine atom);
$R^2$ is $C_{1-6}$ alkyl (e.g., methyl) optionally substituted by a halogen atom; and
X is CH or N.

[Compound I-B]
Compound (I) wherein
ring A is
(A) a pyrazole ring fused with a cyclohexane ring optionally substituted by 1 to 3 halogen atoms (e.g., fluorine atom), or a pyrazole ring fused with a cyclohexadiene ring optionally substituted by 1 to 3 halogen atoms (e.g., fluorine atom),
(B) an oxazole ring fused with a cyclohexene ring, or
(C) a pyridine ring fused with a morpholine ring optionally substituted by 1 to 3 $C_{1-6}$ alkyls (e.g., methyl);
ring B is a benzene ring;
$R^1$ is $C_{1-6}$ alkyl (e.g., propyl) substituted by 1 to 3 halogen atoms (e.g., fluorine atom);
$R^2$ is $C_{1-6}$ alkyl (e.g., methyl); and
X is CH.

[Compound I-C]
Compound (I) wherein
ring A is a pyrazole ring fused with a cyclohexane ring optionally substituted by 1 to 3 halogen atoms (e.g., fluorine atom);
ring B is a benzene ring;
$R^1$ is $C_{1-6}$ alkyl (e.g., propyl) substituted by 1 to 3 halogen atoms (e.g., fluorine atom);
$R^2$ is $C_{1-6}$ alkyl (e.g., methyl); and
X is CH.

[Compound II]
(3R)-1-(4-((1-(4-(5-chloropyrimidin-2-yl)-2-methylphenyl)-4,4,4-trifluorobutyl)amino)benzoyl)piperidine-3-carboxylic acid or a salt thereof (Example 2)
(3R)-1-(4-((4,4,4-trifluoro-1-(2-methyl-4-(5-(trifluoromethyl)pyrimidin-2-yl)phenyl)butyl)amino)benzoyl)piperidine-3-carboxylic acid or a salt thereof (Example 3)
(3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylic acid or a salt thereof (Example 21).

Specific examples of compound (I) include the compounds of the below-mentioned Examples 1-117.

As a salt of compound (I), a pharmacologically acceptable salt is preferable. Examples of such salt include salts with inorganic bases, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N'-dibenzylethylenediamine and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Compound (I) may be a prodrug, and a prodrug of compound (I) means a compound convertible to compound (I), which is the active ingredient, by a reaction due to an enzyme, a gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, and the like.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);
a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);
a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like.

Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

Compound (I) and a prodrug thereof (sometimes to be abbreviated as "the compound of the present invention" in the present specification) also encompass stereoisomers such as cis, trans isomers and the like, racemate, and optically active forms such as R form, S form and the like.

The compound of the present invention may be labeled with an isotope (e.g., $^3$H, $^{13}$C, $^{14}$C, $F^{18}$, $^{35}$S, $^{125}$I) and the like. The compound of the present invention also encompasses a deuterium conversion form wherein $^1$H is converted to $^2$H(D).

Furthermore, the compound of the present invention may be any of hydrate, non-hydrate, solvate and non-solvate.

Compound (I) labeled or substituted with an isotope can be used, for example, as a tracer (PET tracer) used for positron emission tomography (PET), and is useful in the field of medical diagnosis and the like.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

The compound of the present invention has low toxicity (e.g., acute toxicity, chronic toxicity, genetic toxicity, reproductive toxicity, cardiotoxicity, carcinogenicity), shows less side effects and can be used as an agent for the prophylaxis or treatment of various diseases mentioned below in a mammal (e.g., human, mouse, rat, hamster, rabbit, dog, cat, bovine, horse, swine, monkey, sheep) directly or in the form of a pharmaceutical composition (sometimes to be abbreviated as "the medicament of the present invention" in the present specification) by admixing with a pharmacologically acceptable carrier and the like.

Here, examples of the pharmacologically acceptable carrier include various organic or inorganic carrier substances conventionally used as preparation materials, which are added as excipient, lubricant, binder and disintegrant for solid preparations; solvent, solubilizing agent, suspending agent, isotonic agent, buffer and soothing agent for liquid preparations and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonic agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), and natural dye (e.g., β-carotene, chlorophyll, ferric oxide red).

Preferable examples of the sweetener include saccharin sodium, dipotassium glycyrrhizinate, aspartame and stevia.

Examples of the dosage form of the medicament of the present invention include tablet (including sugar-coated tablet, film-coated tablet, sublingual tablet, orally disintegrating tablet, buccal tablet etc.), pill, powder, granule, capsule (including soft capsule, microcapsule), troche, syrup, liquid, emulsion, suspension, aerosol, film (e.g., orally disintegrable film, oral mucosal patch film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, and these can be administered safely by oral or parenteral administration (e.g., intravenous, intramuscular, subcutaneous, intraorgan, intranasal, intradermal, ocular instillation, intracerebral, rectal, vaginal, intraperitoneal and intratumor administrations, administration to the vicinity of tumor etc. and direct administration to the lesion) to mammal.

These preparations may be an immediate-release preparation or a release control preparation such as a sustained-release preparation and the like (e.g., sustained-release microcapsule).

The medicament of the present invention can be produced by a method conventionally used in the technical field of pharmaceutical preparation, for example, the method described in the Japanese Pharmacopoeia and the like.

While the content of the compound of the present invention in the medicament of the present invention varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention has a superior glucagon receptor antagonistic action.

The compound of the present invention can improve, for example, the state in which functional promotion of glucagon is involved (e.g., excess glucose production from the liver, excess secretion of growth hormone, excess suppression of gastric motility and the like) by blocking the action of glucagon. Therefore, the compound of the present invention is useful as a glucagon receptor antagonist, a glucose production inhibitor, a prophylactic or therapeutic agent for diseases in which a promoted action of glucagon is involved, and the like.

Specifically, the compound of the present invention can be used as an agent for the prophylaxis or treatment of obesity, diabetes (e.g., type 1 diabetes, type 2 diabetes, gestational diabetes, obese diabetes), hyperlipidemia/dyslipidemia (e.g., hypertriglyceridemia, hypercholesterolemia, hypoHDL-emia, postprandial hyperlipemia), hypertension, cardiovascular disease (e.g., cardiac failure, arrhythmia, ischemic cardiac diseases, heart valvular disease, arteriosclerosis), diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia, emotional disorder, sexual dysfunction, depression, neurosis, arteriosclerosis, gonitis and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported new diagnostic criteria of diabetes in 1997 and 1998, respectively.

According to these reports, diabetes is a condition showing a fasting blood glucose level (glucose concentration of intravenous plasma) of not less than 126 mg/dl, and a 75 g oral glucose tolerance test 2 h level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the to report of ADA, a condition showing a fasting blood glucose level (glucose concentration of intravenous plasma) of not less than 110 mg/dl and less than 126 mg/d$^1$ is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

Since the compound of the present invention has an activity of inhibiting body weight gain, it can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia and the like. The body weight gain may be caused by excessive feeding or diet without nutrient balance, or may be derived from concomitant drug (e.g., agents for enhancing insulin sensitivity having PPARγ-agonistic activity such as rosiglitazone, pioglitazone and the like). In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

The compound of the present invention is also useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia, cardiac disease-related cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), ischemia, coronary heart disease, non-Q wave MI, congestive cardiac failure, ventricular hypertrophy, new arrhythmia, intermittent claudication, peripheral obstructive artery disease (e.g., peripheral arterial disorder), Alzheimer's disease, Parkinson's disease, anxiety, dementia, insulin resistance syndrome, syndrome X, hyperinsulinemia, sensory abnormality in hyperinsulinemia, tumor (e.g., leukemia, breast cancer, prostate cancer, skin cancer, epithelial cancer, glandular cancer), irritable bowel syndrome, acute or chronic diarrhea, inflammatory disease (e.g., rheumatoid arthritis, spondylitis deformans, osteoarthritis, lumbago, gout, gouty arthritis, postoperative or posttraumatic inflammation, swelling, neuralgia, pharyngolaryngitis, cystitis, hepatitis (including nonalcoholic steatohepatitis), pneumonia, pancreatitis, enteritis, inflammatory bowel disease (including inflammatory colitis), ulcerative colitis, stomach mucosainjury (including stomach mucosa injury caused by aspirin), Lyme disease, rubella arthritis, psoriatic arthritis, conjunctivitis, gastritis, chronic thyroiditis, chronic active hepatitis, Crohn's disease, synovitis, ankylosing spondylitis), small intestine mucosa injury, malabsorption, testis dysfunction, visceral obesity syndrome, sarcopenia, macular degeneration, hypoplastic anemia, thrombocytopenia, multiple sclerosis, periodontal disease, keloid formation, pulmonary sarcoidosis, myasthenia gravis, Reiter's syndrome, influenza, cerebral malaria, silicosis, bone resorption disease, fever, muscular pain, bone disease relating to multiple myeloma, neurodegenerative disease due to trauma, traumatic brain injury, giantism, graft vs host reaction, transplant rejection, skin condition (e.g., scar tissue formation, eczema, atopic dermatitis, contact dermatitis, urticaria, scleroderma, psoriasis), allergy or respiratory diseases (e.g., asthma, respiratory distress syndrome, hay fever, allergic rhinitis, chronic lung inflammatory disease (e.g., chronic obstructive pulmonary diseases (COPD)), inflammation relating to autoimmune diseases (e.g., systemic lupus erythematosus, Addison's disease, polyglandular deficiency syndrome), Graves' disease), infectious disease (e.g., sepsis, septic shock, Shigellosis, *helicobacter pylori*), viral disease (e.g., simple herpes virus infection, cytomegalovirus infection, Epstein-Barr virus infection, human immunodeficiency virus infection, A-type, B-type or C-type hepatitis virus infection), angiogenesis disease (e.g., solid tumor, ocular neovasculization, Hemangioma), edema, analgesia, pain (e.g., neuromuscular pain, headache, cancer or surgical pain, toothache, arthralgia), irritable bowel syndrome, leukemia, central nervous system diseases (e.g., due to cerebral ischemia, cerebral infarction, brain edema and the like), renal fibrosis, hepatic fibrosis, prostate fibrosis, lung fibrosis and the like. Also, the compound of the present invention can also be used as a gastrointestinal motility function improving agent.

In addition, the compound of the present invention can also be used as an agent for the prophylaxis or treatment of various carcinomas (particularly breast cancer (e.g., invasive ductal carcinoma, ductal carcinoma in situ, inflammatory breast cancer and the like), prostate cancer (e.g., hormone-dependent prostate cancer, hormone independent prostate cancer and the like), pancreatic cancer (e.g., pancreatic duct cancer and the like), gastric cancer (e.g., papillary adenocarcinoma, mucinous adenocarcinoma, adenosquamous carcinoma and the like), lung cancer (e.g., non-small cell lung cancer, small cell lung cancer, malignant mesothelioma and the like), colorectal cancer (e.g., gastrointestinal stromal tumor and the like), rectal cancer (e.g., gastrointestinal stromal tumor and the like), colorectal cancer (e.g., familial colorectal cancer, hereditary nonpolyposis colorectal cancer, gastrointestinal stromal tumor and the like), small intestinal cancer (e.g., non-Hodgkin lymphoma, gastrointestinal stromal tumor and the like), esophagus cancer, duodenal cancer, cancer of the tongue, pharyngeal cancer (e.g., nasopharyngeal cancer, mesopharyngeal cancer, hypopharyngeal cancer and the like), salivary gland cancer, brain tumor (e.g., pineal astrocytoma, pilocytic astrocytoma, diffuse astrocytoma, anaplastic astrocytoma and the like), schwannoma, liver cancer (e.g., primary liver cancer, extrahepatic bile duct cancer and the like), kidney cancer (e.g., renal cell carcinoma, transitional carcinoma of kidney pelvis and urinary duct, and the like), biliary tract cancer, endometrial carcinoma, cervical cancer, ovarian cancer (e.g., ovarian epithelial carcinoma, extragonadal germ cell tumor, ovarian germ cell tumor, ovarian low malignant potential tumor and the like), urinary bladder cancer, urinary tract cancer, skin cancer (e.g., intraocular (ocular) melanoma, Merkel cell carcinoma and the like), Hemangioma, malignant lymphoma, malignant melanoma, thyroid cancer (e.g., medullary thyroid carcinoma and the like), parathyroid cancer, nasal cavity cancer, paranasal sinus cancer, bone tumor (e.g., osteosarcoma, Ewing's tumor, uterus sarcoma, soft tissue sarcoma and the like), vascular fibroma, retinoblastoma, penile cancer, testis tumor, solid cancer in childhood (e.g., Wilms' tumor, childhood kidney tumor and the like), Kaposi's sarcoma, Kaposi's sarcoma derived from AIDS, maxillary tumor, fibrous histiocytoma, leiomyosarcoma, rhabdomyosarcoma, leukemia (e.g., acute myeloid leukemia, acute lymphoblastic leukemia and the like) etc.).

The compound of the present invention can also be used for secondary prevention or suppression of progression of the above-mentioned various diseases (e.g., cardiovascular events such as myocardial infarction and the like).

While the dose of the compound of the present invention varies depending on the subject of administration, administration route, target disease, symptom and the like, for example, for oral administration to an adult patient with diabetes, it is generally about 0.01 to 100 mg/kg body weight, preferably 0.05 to 30 mg/kg body weight, further preferably 0.5 to 10 mg/kg body weight for one dose, which is desirably administered once to 3 times a day.

With the aim of enhancing the action of the compound of the present invention or decreasing the dose of the compound and the like, the compound can be used in combination with medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and they may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921, Balaglitazone, MBX-2044, Rivoglitazone, Aleglitazar, Chiglitazar, Lobeglitazone, PLX-204, PN-2034, GFT-505, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), 33 agonists (e.g., AJ-9677), GPR40 agonists (e.g., compound described in WO2004/041266, WO2004/106276, WO2005/063729, WO2005/063725, WO2005/087710, WO2005/095338, WO2007/013689 or WO2008/001931), [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof (preferably [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate)), GLP-1 receptor agonists [e.g., GLP-1, GLP-1MR preparation, Liraglutide, Exenatide, AVE-0010, BIM-51077, Aib(8,35)hGLP-1(7,37)NH$_2$, CJC-1131, Albiglutide], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon receptor antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP- 355, compound described in WO 2006/112549, WO 2007/028135, WO 2008/047821, WO 2008/050821, WO 2008/136428 or WO2008/156757), GIP (Glucose-dependent insulinotropic peptide) and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxy)propyl]oxazole), the compound described in WO2004/039365), nerve regeneration promoter (e.g., Y-128), PKC inhibitors (e.g., ruboxistaurin mesylate), AGE inhibitors (e.g., ALT946, pyratoxanthine, N-phenacylthiazolium bromide (ALT766), ALT-711, EXO-226, Pyridorin, pyridoxamine), GABA receptor agonists (e.g., gabapentin, pregabalin), serotonin-noradrenaline reuptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitor and the like.

Examples of the therapeutic agent for hyperlipidemia include statin compounds (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, gamma oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril and the like), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine and the like), β blockers (e.g., metoprolol, atenolol, propranolol, carvedilol, pindolol), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), MCH receptor antagonists (e.g., SB-568849; SNAP-7941; compound described in WO01/82925 or WO01/87834), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), 133 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), a combination agent of naltrexone hydrochloride sustained-release preparation and bupropion hydrochloride sustained-release preparation, anorexigenic agents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the antithrombotic agents include heparin (e.g., heparin sodium, heparin calcium, enoxaparin sodium, dalteparin sodium), warfarin (e.g., warfarin potassium), antithrombin drugs (e.g., argatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride), prasugrel, E5555, SHC530348), FXa inhibitors (e.g., rivaroxaban, apixaban, edoxaban, YM150, the compound described in WO02/06234, WO2004/048363, WO2005/030740, WO2005/058823 or WO2005/113504) and the like.

The combination drug is preferably biguanide (preferably metformin or hydrochloride thereof), dipeptidyl peptidase IV inhibitor (preferably alogliptin or benzoate thereof, 2-[[6-[(3R)-3-amino-1-piperidinyl]-3,4-dihydro-3-methyl-2,4-dioxo-1(2H)-pyrimidinyl]methyl]-4-fluorobenzonitrile or succinate thereof), GPR40 agonist (preferably [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate), PPAR function regulator (preferably pioglitazone or hydrochloride thereof), sulfonylurea (preferably glibenclamide, glimepiride), α-glucosidase inhibitor (preferably voglibose), insulin preparation, mitiglinide or calcium salt hydrate thereof, nateglinide or the like.

The administration mode of the concomitant drug is not particularly limited, and the compound of the present invention and the concomitant drug only need to be combined on administration. Examples of such administration mode include the following:

1) administration of a single preparation obtained by simultaneously processing the compound of the present invention and the concomitant drug,
2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

The production method of the compound of the present invention is explained in the following.

In the following Reaction Schemes, starting compounds may be each in the form of a salt as long as it does not inhibit the reaction. Examples of the salt include those exemplified as the above-mentioned salt of the compound represented by formula (I).

When a specific production method is not described, the starting compound may be easily commercially available, or can also be produced according to a method known per se, or a method analogous thereto.

In each reaction of the following Reaction Schemes, the product can be used for the next reaction as the reaction mixture or as a crude product, or can also be isolated according to a conventional method from the reaction mixture, and can also be easily purified according to a conventional separation means (e.g., recrystallization, distillation, chromatography). For example, they can be performed by the method described in the Examples, or a method analogous thereto and the like.

When the reagents and reaction agents to be used in each reaction are commercially available, the commercially available products can be directly used, or they can also be produced according to a method known per se or a method analogous thereto, or the method described in the Examples. For example, the reagents and reaction agents described in the Examples can be used.

Unless particularly indicated, the solvent of each reaction is not particularly limited as long as the reaction proceeds and the reaction can be performed in a solvent inert to the reaction, or without solvent, or in two or more kinds thereof mixed at an appropriate ratio. For example, the solvents described in the Examples can be used.

Unless particularly indicated, the equivalents of the reagents and reaction agents used in each reaction is 0.001 equivalents—100 equivalents relative to the substrate of each reaction. For example, equivalents of the reagents and reaction agents described in the Examples can be used.

Unless particularly indicated, the reaction time of each reaction is generally 5 min-72 hr. For example, the reaction time described in the Examples can be employed.

Unless particularly indicated, the reaction temperature of each reaction is ice-cooling to heating under reflux. For example, the reaction temperature described in the Examples can be employed.

When alkylation reaction, hydrolysis reaction, amination reaction, esterification reaction, amidation reaction, esterification reaction, etherification reaction, oxidation reaction, reduction reaction and the like are to be performed in the following Reaction Schemes, these reactions are performed according to a method known per se. Examples of such method include the methods described in ORGANIC FUNCTIONAL GROUP PREPARATIONS, 2nd ed., ACADEMIC PRESS, INC., 1989; Comprehensive Organic Transformations, VCH Publishers Inc., 1989 and the like, and the like.

The following are explanations of the solvents in generic terms, which are used for the following reactions.

Examples of the "nitrile solvents" include acetonitrile, propionitrile and the like.

Examples of the "amide solvents" include N,N-dimethylformamide (DMF), N,N-dimethylacetamide, N-methylpyrrolidone and the like.

Examples of the "halogenated hydrocarbon solvents" include dichloromethane, chloroform, 1,2-dichloroethane, carbon tetrachloride and the like.

Examples of the "ether solvents" include diethyl ether, diisopropyl ether, tert-butyl methyl ether, tetrahydrofuran (THF), 1,4-dioxane, 1,2-dimethoxyethane and the like.

Examples of the "aromatic solvents" include benzene, toluene, xylene, chlorobenzene, (trifluoromethyl)benzene, pyridine and the like.

Examples of the "aliphatic hydrocarbon solvents" include hexane, pentane, cyclohexane and the like.

Examples of the "sulfoxide solvents" include dimethyl sulfoxide (DMSO) and the like.

Examples of the "alcohol solvents" include methanol, ethanol, propanol, 2-propanol, butanol, isobutanol, tert-butanol and the like.

Examples of the "ester solvents" include methyl acetate, ethyl acetate, n-butyl acetate, tert-butyl acetate and the like.

Examples of the "ketone solvents" include acetone, methyl ethyl ketone and the like.

Examples of the "organic acid solvents" include formic acid, acetic acid, propionic acid, trifluoroacetic acid, methanesulfonic acid and the like.

The following are explanations of the bases in generic terms, which are used for the following reactions.

Examples of the "inorganic bases" include sodium hydroxide, potassium hydroxide, lithium hydroxide, barium hydroxide and the like.

Examples of the "basic salt" include sodium carbonate, potassium carbonate, cesium carbonate, sodium hydrogen carbonate, potassium hydrogen carbonate and the like.

Examples of the "aromatic amines" include pyridine, imidazole, 2,6-lutidine and the like.

Examples of the "tertiary amines" include triethylamine, diisopropylethylamine, N-methylmorpholine, DBU (1,8-diazabicyclo[5.4.0]undec-7-ene), DBN (1,5-diazabicyclo[4.3.0]non-5-ene) and the like.

Examples of the "hydrides of an alkali metal or alkaline earth metal" include lithium hydride, sodium hydride, potassium hydride, calcium hydride and the like.

Examples of the "metal amides" include lithium amide, sodium amide, lithium diisopropylamide, lithium dicyclohexylamide, lithium hexamethyldisilazide, sodium hexamethyldisilazide, potassium hexamethyldisilazide and the like.

Examples of the "alkyl metals" include n-butyllithium, sec-butyllithium, tert-butyllithium, methylmagnesium bromide and the like.

Examples of the "aryl metals" include phenyllithium, phenylmagnesium bromide and the like.

Examples of the "metal alkoxides" include sodium methoxide, sodium ethoxide, potassium tert-butoxide and the like.

In the following production methods, when the starting compound has an amino group, a carboxyl group, a hydroxy group, a carbonyl group or a sulfanyl group, a protecting group generally used in peptide chemistry and the like may be introduced into these groups. By removing the protecting group as necessary after the reaction, the object compound can be obtained.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a substituted $C_{7-10}$ aralkyl group (e.g., 2,4-dimethoxybenzyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl, triiso-propylsilyl, tert-butyldiphenylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group or a nitro group.

Examples of the carbonyl-protecting group include a cyclic acetal (e.g., 1,3-dioxane, 1,3-dioxolane), a non-cyclic acetal (e.g., di-$C_{1-6}$ alkylacetal) and the like.

Examples of the sulfanyl-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The removal method of the protecting group can be carried out according to a method known per se, for example, the method described in "Protective Groups in Organic Synthesis, Third Edition, Wiley-Interscience (1999)" or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

Compound (I) can be produced, for example, according to the method shown in the following reaction scheme 1.

<Reaction Scheme 1>

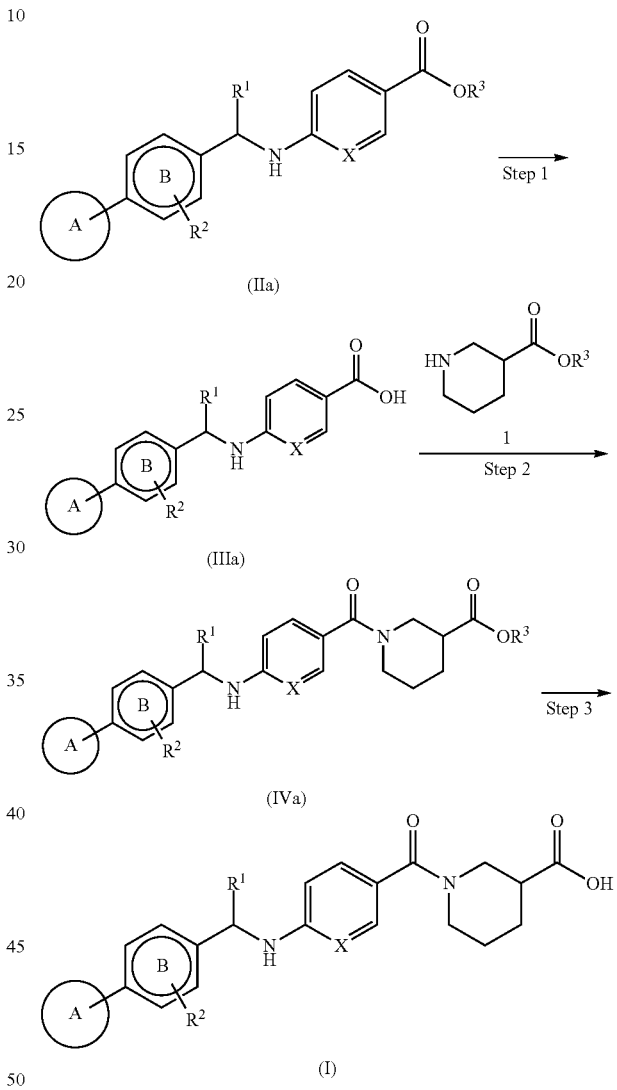

wherein $R^3$ is $C_{1-6}$ alkyl, and other symbols are as defined above.

Step 1

Compound (IIIa) can be produced by hydrolyzing the ester group of compound (IIa) according to a method known per se, for example, the method described in "Protective Groups in Organic Synthesis, Third Edition, Wiley-Interscience (1999)" or a method analogous thereto.

Step 2

Compound (IVa) can be produced by, for example, condensing compound (IIIa) and compound 1.

The condensation reaction can be performed by a general peptide coupling method according to a conventional method. Examples of such method include a method including direct condensation of compound (IIIa) and compound 1 by using a condensing agent.

Examples of the condensing agent include carbodiimide condensation reagents such as dicyclohexylcarbodiimide (DCC), diisopropylcarbodiimide (DIPC), 1-ethyl-3-(3-dimethylaminopropyl)carbodiimide (EDC, WSC and the like), or a hydrochloride thereof and the like; phosphoric acid condensation reagents such as diethyl cyanophosphate, diphenylphosphoryl azide and the like; carbonyldiimidazole, 2-chloro-1,3-dimethylimidazolium tetrafluoroborate, 2-(7-aza-1H-benzotriazol-1-yl)-1,1,3,3-tetramethyluronium hexafluorophosphate (HATU) and the like.

Examples of the solvent to be used for the condensation reaction include amide solvents, sulfoxide solvents, halogenated hydrocarbon solvents, aromatic solvents, ether solvents, ester solvent, nitrile solvents, water and the like. These solvents may be used by mixing at an appropriate ratio.

When the carbodiimide condensation reagent is used as a condensing agent, the reaction efficiency can be improved by using, as necessary, a suitable condensation accelerator (e.g., 1-hydroxy-7-azabenzotriazole, 1-hydroxybenzotriazole, N-hydroxysuccinimide, N-hydroxyphthalimide).

The reaction efficiency can be improved by using an organic amine base such as triethylamine, N,N-diisopropylethylamine and the like.

Compound 1 may be a commercially available product, or can be produced by using a commercially available compound according to a method known per se or a method analogous thereto.

Step 3

Compound (I) can be produced by hydrolyzing the ester group of compound (IVa) according to a method known per se, for example, the method described in "Protective Groups in Organic Synthesis, Third Edition, Wiley-Interscience (1999)" or a method analogous thereto.

Compound (I) can also be produced, for example, by the method shown by the following reaction scheme 2.

<Reaction Scheme 2>

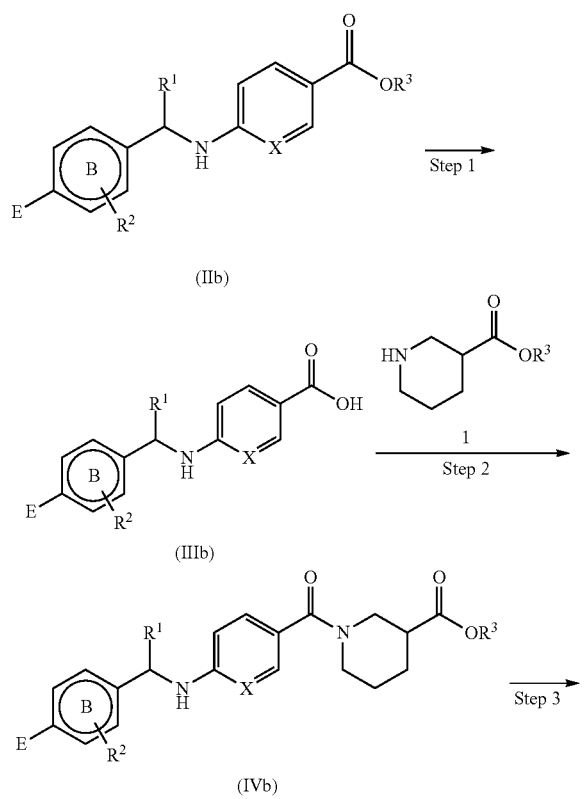

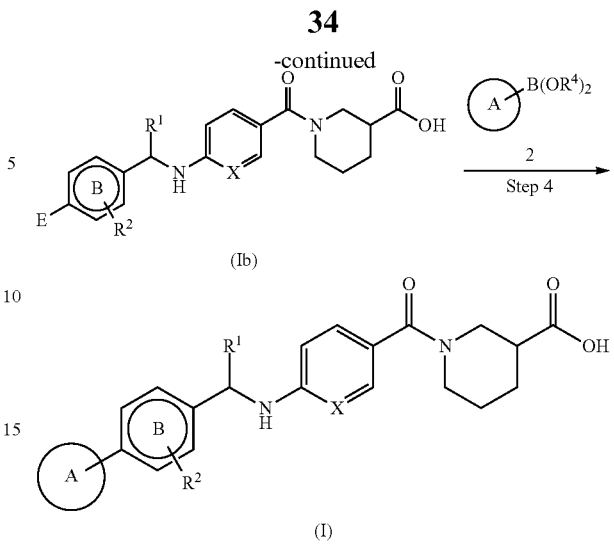

wherein E is a leaving group (e.g., a halogen atom (e.g., bromine, chlorine, iodine), a trifluoromethanesulfonyloxy group, a methanesulfonyloxy group, a p-toluenesulfonyloxy group), $R^4$ is hydrogen or $C_{1-6}$ alkyl, and other symbols are as defined above.

Step 1

Compound (IIIb) can be produced by hydrolyzing the ester group of compound (IIb) according to a method known per se, for example, the method described in "Protective Groups in Organic Synthesis, Third Edition, Wiley-Interscience (1999)" or a method analogous thereto.

Step 2

Compound (IVb) can be produced by condensing compound (IIIb) and compound 1 according to, for example, the method described in reaction scheme 1, step 2 or a method analogous thereto.

Step 3

Compound (Ib) can be produced by hydrolyzing the ester group of compound (IVb) according to a method known per se, for example, the method described in "Protective Groups in Organic Synthesis, Third Edition, Wiley-Interscience (1999)" or a method analogous thereto.

Step 4

Compound (I) can be produced by the Suzuki-Miyaura coupling reaction known per se, by a reaction of compound (Ib) with boronic acid or boronic acid ester 2 by using a palladium catalyst according to, for example, the method described in "Handbook of Functionalized Organometallics, Vol. 1, Functionalized Organoborane Derivatives in Organic Synthesis, pp. 45-108, Wiley-VCH: Weinheim (2005)" or a method analogous thereto.

Compound 2 may be a commercially available product, or can be produced by using a commercially available compound according to a method known per se or a method analogous thereto.

Compound IIa (IIa1, IIa2, IIa3) used in reaction scheme 1 can be produced by, for example, the methods shown by the following reaction scheme 3, reaction scheme 4, reaction scheme 5 and reaction scheme 6.

<Reaction Scheme 3>

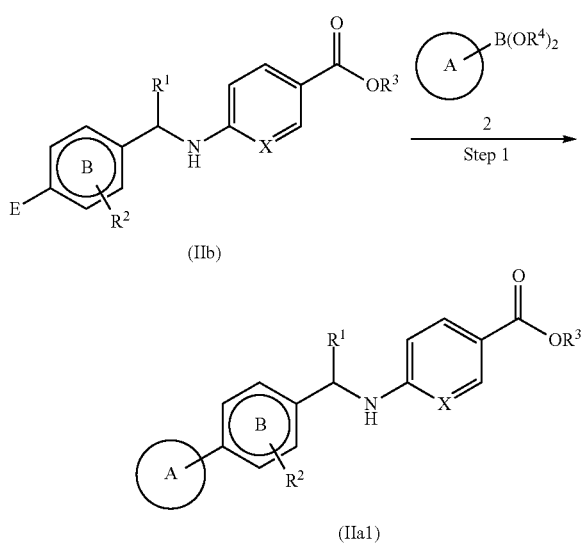

(IIa1)

wherein the symbols are as defined above.

Step 1

Compound (IIa1) can be produced by a reaction known per se, for example, the Suzuki-Miyaura coupling reaction of compound (IIb) with boronic acid or boronic acid ester 2 by using a palladium catalyst according to the method described in "Handbook of Functionalized Organometallics, Vol. 1, Functionalized Organoborane Derivatives in Organic Synthesis, pp. 45-108, Wiley-VCH: Weinheim (2005)" or a method analogous thereto.

<Reaction Scheme 4>

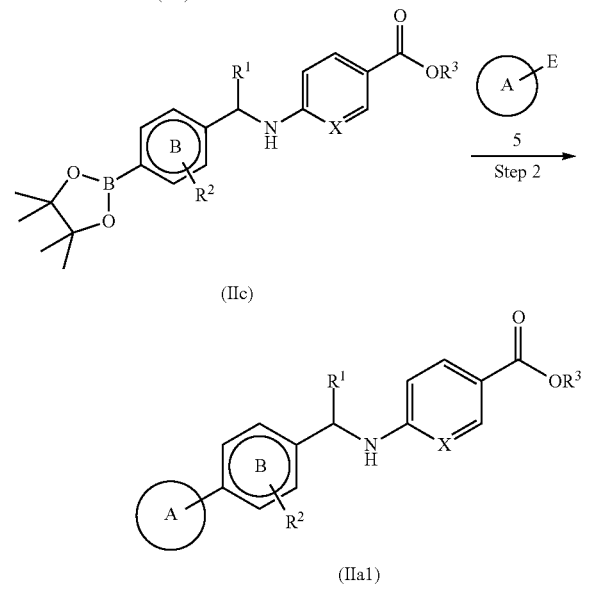

Step 1

Compound (IIc) can be produced by a reaction known per se, for example, the Miyaura-Ishiyama boration reaction of compound (IIb) and bis(pinacolato)borane 4, according to the method described in "J. Org. Chem., 1995, 60, 7508-7510." or a method analogous thereto.

Step 2

Compound (IIa1) can be produced by a reaction known per se, for example, by the Suzuki-Miyaura coupling reaction of compound (IIc) and compound 5 by using a palladium catalyst, according to the method described in "Handbook of Functionalized Organometallics, Vol. 1, Functionalized Organoborane Derivatives in Organic Synthesis, pp. 45-108, Wiley-VCH: Weinheim (2005)" or a method analogous thereto.

Compounds 4 and 5 may be commercially available products, or can be produced using commercially available compounds and according to a method known per se or a method analogous thereto.

<Reaction Scheme 5>

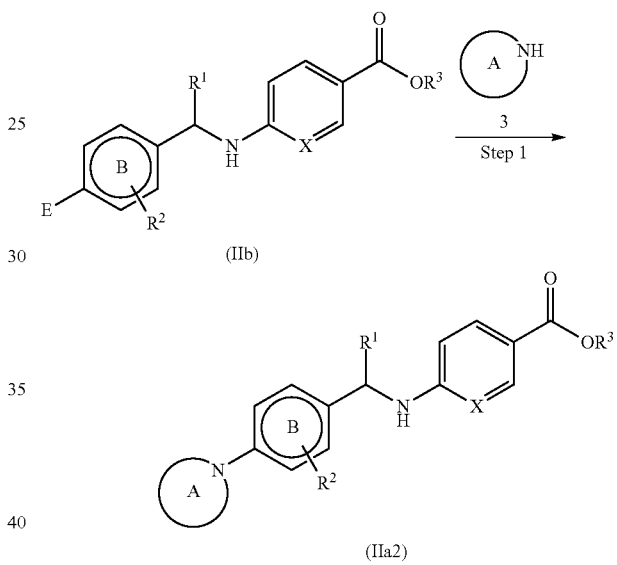

(IIa2)

wherein the symbols are as defined above.

Step 1

Compound (IIa2) can be produced by a reaction known per se, for example, by an amination reaction of compound (IIb) and nitrogen-containing aromatic compound 3 such as pyrazole, triazole and the like, according to the method described in "J. Org. Chem., 2004, 69, 5578-5587" or "Chemical Science. 2011, 2, 27-50" or a method analogous thereto.

Compound 3 may be a commercially available product, or can be produced using a commercially available compound and according to a method known per se or a method analogous thereto.

<Reaction Scheme 6>

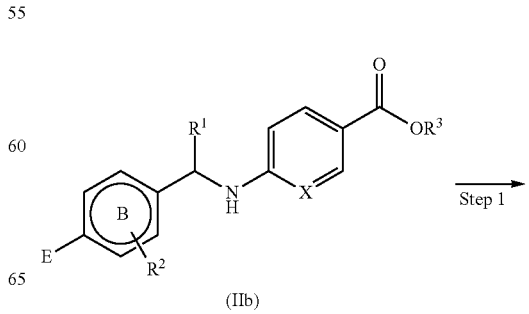

(IIb)

-continued

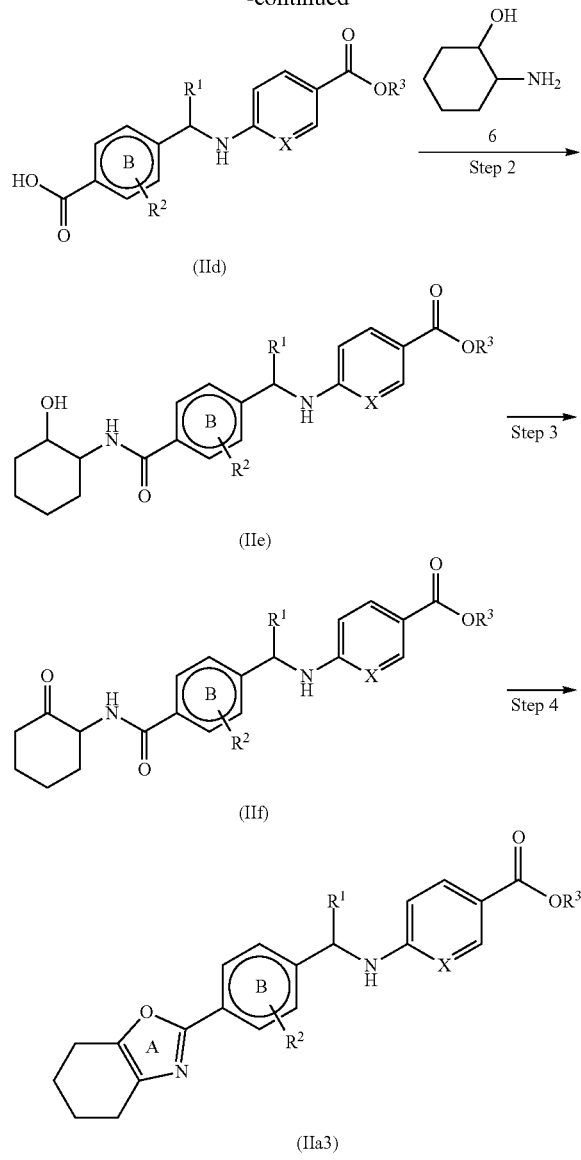

wherein the symbols are as defined above.

Step 1

Compound (IId) can be produced by a reaction known per se, for example, by a hydroxycarbonylation reaction of compound (IIb), according to the method described in "Organic Letters, 2003, 5, 4269-4272" or a method analogous thereto.

Step 2

Compound (IIe) can be produced by a condensation reaction of compound (IId) and compound 6, according to the method described in reaction scheme 1, step 2, or a method analogous thereto.

Step 3

Compound (IIf) can be produced by an oxidation reaction of the hydroxy group of compound (IIe), for example, by the Dess-Martin oxidation reaction according to the method described in "J. Am. Chem. Soc., 1991, 113, 7277" or a method analogous thereto.

Step 4

Compound (IIa3) can be produced by a cyclization reaction of compound (IIf) with an acid such as phosphorus oxychloride.

Compound 6 may be a commercially available product, or can be produced using a commercially available compound and according to a method known per se or a method analogous thereto.

Compound (IIb) used in reaction scheme 2, reaction scheme 3, reaction scheme 4, reaction scheme 5 and reaction scheme 6 can be produced by the method of reaction scheme 7 shown below.

<Reaction Scheme 7>

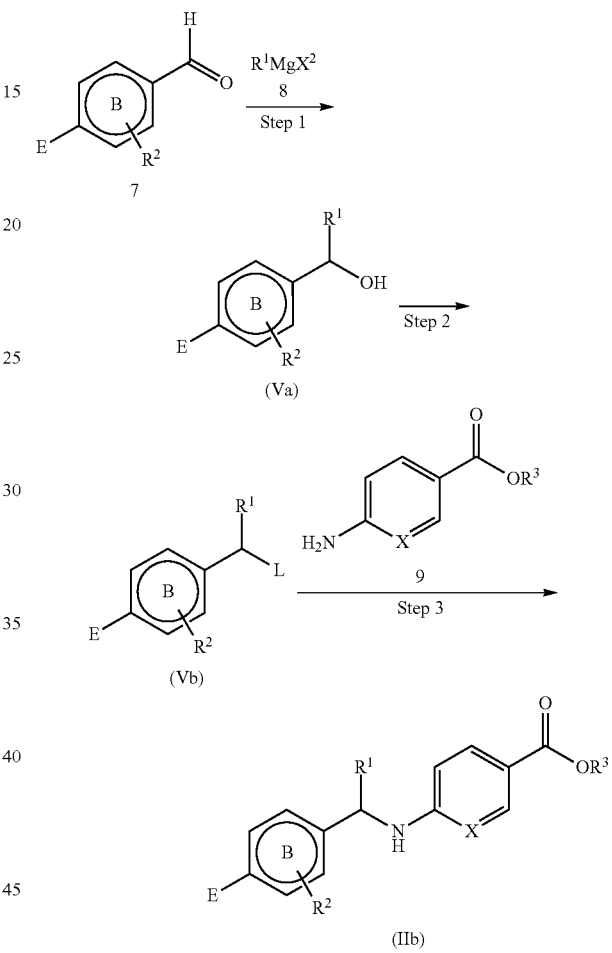

wherein $X^2$ is a halogen atom (e.g., bromine, chlorine, iodine), L is a leaving group (e.g., chlorine, a methanesulfonyloxy group), and other symbols are as defined above.

Step 1

Compound (Va) can be produced by a reaction known per se, for example, by the Grignard reaction of compound 7 and organic magnesium compound 8, according to the method described in "Angew. Chem. Int. Ed., 2003, 42, 4302-4320" and "J. Org. Chem., 2010, 75, 5008-5016" or a method analogous thereto.

Step 2

Compound (Vb) can be produced by, for example, converting the hydroxy group of compound (Va) to a leaving group. Such conversion to a leaving group can be performed by a reaction with methanesulfonyl chloride, phosphoryl chloride or thionyl chloride in the presence of an appropriate base according to a conventional method.

Step 3

Compound (IIb) can be produced by, for example, reacting compound (Vb) with compound 9 in the presence of a base. In this reaction, sodium iodide, potassium iodide and the like may be added as a reaction promoter.

Compound 7 and compound 8 may be commercially available products, or can be produced by using commercially available compounds and according to a method known per se or a method analogous thereto.

Compound (Va) used in reaction scheme 7 can be produced by the method of reaction scheme 8 shown below.
<Reaction Scheme 8>

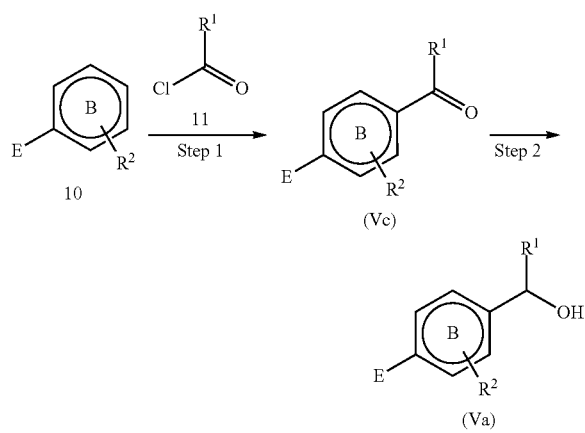

Step 1

Compound (Vc) can be produced by a reaction known per se, for example, by the Friedel-Crafts reaction of compound 10 and compound 11, according to the method described in "Angew. Chem. Int. Ed., 2004, 43, 550-556" or a method analogous thereto.
Step 2

Compound (Va) can be produced by a reaction known per se, for example, by a reduction reaction of compound (Vc), according to the method described in "Reductions by the Alumino- and Borohydrides in Organic Synthesis, 2nd ed., Wiley-VCH: New York (1997)" or a method analogous thereto.

In compound (I) thus obtained, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production methods can be isolated and purified according to a known means, for example, solvent extraction, liquid conversion, phase transfer, crystallization, recrystallization, chromatography and the like.

When compound (I) contains an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

Compound (I) may be a crystal.

Crystals of compound (I) (hereinafter sometimes to be abbreviated as the crystals of the present invention) can be produced according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Examples, the following abbreviations are used.
mp: melting point
THF: tetrahydrofuran
DMF: N,N-dimethylformamide
DMA: N,N-dimethylacetamide
DME: 1,2-dimethoxyethane
DMSO: dimethyl sulfoxide
WSC: 1-ethyl-3-(3-dimethylaminopropyl)carbodiimide hydrochloride
HOBt: 1-hydroxybenzotriazole monohydrate
$^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are not described.

Other abbreviations used in the specification mean the following.
s: singlet
d: doublet
t: triplet
q: quartet
m: multiplet
br: broad
J: coupling constant
Hz: hertz
CDCl$_3$: deuterated chloroform
DMSO-d$_6$: d$_6$-dimethyl sulfoxide
$^1$H-NMR: proton nuclear magnetic resonance
TFA: trifluoroacetic acid MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxyl group (—OH), a peak after elimination of $H_2O$ may be observed as a fragment ion. In the case of a salt, a molecular ion peak or fragment ion peak of free form is generally observed.

The unit of reagent concentration (c) in optical rotation ($[\alpha]D$) is g/100 mL.

As the elemental analysis values (Anal.), calculated values (Calcd) and measured values (Found) are described.

Example 1

(3R)-1-(4-((4,4,4-trifluoro-1-(2-methyl-4-(5-(trifluoromethyl)pyridin-2-yl)phenyl)butyl)amino)benzoyl) piperidine-3-carboxylic acid A) iodo(3,3,3-trifluoropropyl)magnesium diethyl ether solution To a reaction mixture of magnesium (127 g), iodine (52 g) and diethyl ether (2.4 L) was slowly added a solution of 1,1,1-trifluoro-3-iodopropane (910 g) in diethyl ether (300 mL) at 0° C. to 20° C. under a nitrogen atmosphere. The reaction mixture was stirred at room temperature for 16 hr, and stirred under reflux for 6 hr to give the title compound. This reaction was performed for 3 batches, and each obtained compound was used in step B without further purification.

B) 1-(4-bromo-2-methylphenyl)-4,4,4-trifluorobutan-1-ol

To a solution of 4-bromo-2-methylbenzaldehyde (760 g) in diethyl ether (3.8 L) was added the iodo(3,3,3-trifluoropropyl)magnesium diethyl ether solution obtained in step A at 0° C. to 15° C. under a nitrogen atmosphere, and the reaction mixture was stirred for 3 days. To the reaction mixture was added 2M hydrochloric acid. This reaction was performed for 3 batches, and the obtained respective reaction mixtures were combined, and the mixture was extracted with ethyl acetate. The extract was washed with saturated brine, dried over anhydrous sodium sulfate, and the solvent was evaporated under reduced pressure. The residue was purified by silica gel column chromatography (ethyl acetate/petroleum ether) to give the title compound (1365 g).

$^1$H NMR (400 MHz, CDCl$_3$) δ 1.83-1.93 (3H, m), 2.24-2.35 (5H, m), 4.93-4.96 (1H, m), 7.33 (1H, d, J=1 Hz), 7.35-7.38 (2H, m).

C) 4-bromo-1-(1-chloro-4,4,4-trifluorobutyl)-2-methylbenzene

To a solution of 1-(4-bromo-2-methylphenyl)-4,4,4-trifluorobutan-1-ol (545 g) in toluene (5.4 L) was added thionyl chloride (393 g) at room temperature. The reaction mixture was stirred at 50° C. overnight and concentrated under reduced pressure to give the title compound. This reaction was performed for 3 batches, and the obtained compounds were used in step D without further purification.

D) methyl 4-((1-(4-bromo-2-methylphenyl)-4,4,4-trifluorobutyl)amino)benzoate (racemate)

A reaction mixture of 4-bromo-1-(1-chloro-4,4,4-trifluorobutyl)-2-methylbenzene (369 g), sodium carbonate (245% g), methyl 4-aminobenzoate (194 g), sodium iodide (347 g) and DMA (1.2 L) was stirred at 50° C. for 3 hr. The reaction mixture was added to water. This reaction was performed for 3 batches, the obtained respective reaction mixtures were combined, and the mixture was extracted with ethyl acetate. The extract was dried over anhydrous sodium sulfate, and the solvent was evaporated under reduced pressure. The resulting solid was collected by filtration and washed with petroleum ether to give the title compound (1164 g).

$^1$H NMR (400 MHz, CDCl$_3$) δ 2.00-2.01 (2H, m), 2.12-2.31 (2H, m), 2.42 (3H, s), 3.84 (3H, s), 4.33 (1H, brs), 4.62-4.65 (1H, m), 6.42-6.44 (2H, d, J=8.82 Hz), 7.13-7.15 (1H, d, J=8.36 Hz), 7.25-7.30 (1H, dd, J=8.35, 2.03 Hz), 7.36 (1H, d, J=2.04 Hz), 7.79-7.81 (2H, d, J=8.81 Hz).

E) methyl 4-((1-(4-bromo-2-methylphenyl)-4,4,4-trifluorobutyl)amino)benzoate (optically active form, compound with longer retention time)

Racemate (1.4 kg) of methyl 4-((1-(4-bromo-2-methylphenyl)-4,4,4-trifluorobutyl)amino)benzoate was fractionated by SFC (column: CHIRALPAK AD-10µ (trade name), 50 mmID×300 mL, manufactured by DAICEL CHEMICAL INDUSTRIES, LTD., mobile phase: carbon dioxide/methanol=600/400) to give the title compound (646.9 g) with longer retention time.

MS (ESI+), found: 428.1.

$[\alpha]_D^{20}$ −64.43 (c 0.699, CHCl$_3$/DMF=4/1)

99.59% ee (tR2(AD-H))

compound with longer retention time by SFC (column: CHIRALPAK AD-H (trade name), 4.6 mmID×150 mL, manufactured by DAICEL CHEMICAL INDUSTRIES, LTD., mobile phase: carbon dioxide/methanol/diethylamine=600/400/5)

F) methyl 4-((4,4,4-trifluoro-1-(2-methyl-4-(4,4,5,5-tetramethyl-1,3,2-dioxaborolan-2-yl)phenyl)butyl) amino)benzoate A reaction mixture of methyl 4-((1-(4-bromo-2-methylphenyl)-4,4,4-trifluorobutyl)amino)benzoate (optically active form, compound with longer retention time) (30 g) and 4,4,4',4',5,5,5',5'-octamethyl-2,2'-bi-1,3,2-dioxaborolane (26.6 g), 1,1'-bis(diphenylphosphino)ferrocene-palladium (II)dichloromethane complex (2.85 g), potassium acetate (27.4 g) and DMSO (150 mL) was stirred at 90° C. overnight under a nitrogen atmosphere. The reaction mixture was added to water, and the precipitate was collected by filtration. The precipitate was dissolved in ethyl acetate, washed with water and saturated brine, and dried over anhydrous magnesium sulfate. The solvent was evaporated under reduced pressure and the residue was purified by silica gel column chromatography (ethyl acetate/hexane) to give the title compound (28.7 g).

MS (ESI−), found: 476.3.

G) methyl 4-(5,5,5-trifluoro-2-(2-methyl-4-(5-(trifluoromethyl)pyridin-2-yl)phenyl)pentyl)benzoate A reaction mixture of methyl 4-((4,4,4-trifluoro-1-(2-methyl-4-(4,4,5,5-tetramethyl-1,3,2-dioxaborolan-2-yl)phenyl) butyl)amino)benzoate (14.3 g) obtained in step F, 2-bromo-5-(trifluoromethyl)pyridine (7.45 g), tris(dibenzylideneacetone)dipalladium (1.37 g), 2,6-dimethoxy-2' (dicyclohexylphosphino)biphenyl (2.46 g), cesium carbonate (29.3 g), dimethylformamide (100 mL) and water (25 ml) was stirred at 80° C. overnight under a nitrogen atmosphere. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (13.6 g).

MS (ESI+): [M+H]$^+$ 497.4.

H) 4-((4,4,4-trifluoro-1-(2-methyl-4-(5-(trifluoromethyl)pyridin-2-yl)phenyl)butyl)amino)benzoic acid A reaction mixture of methyl 4-(5,5,5-trifluoro-2-(2-methyl-4-(5-(trifluoromethyl)pyridin-2-yl)phenyl)pentyl)benzoate (13.6 g), 1M aqueous sodium hydroxide solution (82 mL), THF (82 mL) and methanol (82 mL) was stirred at 70° C. for 7 hr. The reaction mixture was neutralized with 1M hydrochloric acid at 0° C. and extracted with ethyl acetate. The extract was washed with water and saturated brine, and dried over anhydrous magnesium sulfate. The solvent was evaporated under reduced pressure to give the title compound as a crudely purified product. This compound was used in step 1 without further purification.

MS (ESI+): [M+H]$^+$ 483.4.

I) ethyl (3R)-1-(4-((4,4,4-trifluoro-1-(2-methyl-4-(5-(trifluoromethyl)pyridin-2-yl)phenyl)butyl)amino) benzoyl)piperidine-3-carboxylate A solution of 4-((4,4,4-trifluoro-1-(2-methyl-4-(5-(trifluoromethyl)pyridin-2-yl)phenyl)butyl)amino)benzoic acid obtained in step H, ethyl (3R)-piperidine-3-carboxylate (5.05 mL), 1-hydroxybenzotriazole (4.43 g), 1-ethyl-3-(3-dimethylaminopropyl)carbodiimide hydrochloride (6.28 g), diisopropylethylamine (5.72 mL) in dimethylformamide (91 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (15.9 g).

MS (ESI+): [M+H]$^+$ 622.6.

compound with shorter retention time by HPLC (column: CHIRALPAK AD-H (trade name), 4.6 mmID×250 mL, manufactured by DAICEL CHEMICAL INDUSTRIES, LTD., mobile phase: hexane/2-propanol=700/300)

J) (3R)-1-(4-((4,4,4-trifluoro-1-(2-methyl-4-(5-(trifluoromethyl)pyridin-2-yl)phenyl)butyl)amino)benzoyl)piperidine-3-carboxylic acid To a reaction mixture of ethyl (3R)-1-(4-((4,4,4-trifluoro-1-(2-methyl-4-(5-(trifluoromethyl)pyridin-2-yl)phenyl)butyl)amino)benzoyl)piperidine-3-carboxylate (15.6 g), ethanol (50 mL) and tetrahydrofuran (50 ml) was added 1M aqueous sodium hydroxide solution (50.2 mL) at 0° C., and the mixture was stirred at room temperature for 3 hr. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure and the residue was crystallized from diethyl ether to give the title compound (10.4 g) as a white solid.

$^1$H NMR (300 MHz, DMSO-d$_6$) δ 1.27-1.71 (3H, m), 1.81-2.05 (3H, m), 2.30-2.58 (6H, m), 2.81-3.07 (2H, m), 3.82 (1H, brs), 4.05 (1H, brs), 4.72 (1H, q, J=7.1 Hz), 6.48 (2H, d, J=8.7 Hz), 6.81 (1H, d, J=7.6 Hz), 7.10 (2H, d, J=8.5 Hz), 7.50 (1H, d, J=8.2 Hz), 7.93 (1H, dd, J=8.1, 1.6 Hz), 8.01 (1H, d, J=1.4 Hz), 8.11-8.20 (1H, m), 8.21-8.30 (1H, m), 9.00 (1H, d, J=0.8 Hz), 12.37 (1H, brs).

Anal. Calcd for C$_{30}$H$_{29}$F$_6$N$_3$O$_3$: C, 60.71; H, 4.92; N, 7.08. Found: C, 60.53; H, 4.97; N, 7.03.

compound with shorter retention time by HPLC (column: CHIRALPAK AD3 (trade name), 4.6 mmID×250 mL, manufactured by DAICEL CHEMICAL INDUSTRIES, LTD., mobile phase: hexane/ethanol/TFA=700/300/5)

Example 2

(3R)-1-(4-((1-(4-(5-chloropyrimidin-2-yl)-2-methylphenyl)-4,4,4-trifluorobutyl)amino)benzoyl)piperidine-3-carboxylic acid

A) methyl 4-((1-(4-(5-chloropyrimidin-2-yl)-2-methylphenyl)-4,4,4-trifluorobutyl)amino)benzoate A reaction mixture of methyl 4-((4,4,4-trifluoro-1-(2-methyl-4-(4,4,5,5-tetramethyl-1,3,2-dioxaborolan-2-yl)phenyl)butyl)amino)benzoate (7.85 g) obtained in Example 1, step F, 5-chloro-2-iodopyrimidine (4.35 g), tris(dibenzylideneacetone)dipalladium (0.753 g), 2,6-dimethoxy-2'-(dicyclohexylphosphino)biphenyl (1.35 g), cesium carbonate (16.08 g), dimethylformamide (65.8 mL) and water (16.5 ml) was stirred at 60° C. for 24 hr under a nitrogen atmosphere. The reaction mixture was added to saturated aqueous ammonium chloride solution, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) and washed with diethyl ether to give the title compound (4.61 g).

MS (ESI–), found: 462.2.

B) 4-((1-(4-(5-chloropyrimidin-2-yl)-2-methylphenyl)-4,4,4-trifluorobutyl)amino)benzoic acid A reaction mixture of methyl 4-((1-(4-(5-chloropyrimidin-2-yl)-2-methylphenyl)-4,4,4-trifluorobutyl)amino)benzoate (9.63 g), 1M aqueous sodium hydroxide solution (83 mL), THF (40 mL) and methanol (40 mL) was stirred at 70° C. for 6 hr. The reaction mixture was neutralized with 1M hydrochloric acid at 0° C., and extracted with ethyl acetate. The extract was washed with saturated brine, and dried over anhydrous magnesium sulfate. The solvent was evaporated under reduced pressure to give the title compound as a crudely purified product. This compound was used in step C without further purification.

MS (ESI–), found: 448.2.

C) ethyl (3R)-1-(4-((1-(4-(5-chloropyrimidin-2-yl)-2-methylphenyl)-4,4,4-trifluorobutyl)amino)benzoyl)piperidine-3-carboxylate A solution of 4-((1-(4-(5-chloropyrimidin-2-yl)-2-methylphenyl)-4,4,4-trifluorobutyl)amino)benzoic acid, ethyl (3R)-piperidine-3-carboxylate (6.40 mL), 1-hydroxybenzotriazole (5.61 g), 1-ethyl-3-(3-dimethylaminopropyl)carbodiimide hydrochloride (7.96 g) and diisopropylethylamine (7.25 mL) in dimethylformamide (60 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (8.88 g).

MS (ESI+): [M+H]+ 589.2.

compound with shorter retention time by HPLC (column: CHIRALPAK AD (trade name), 4.6 mmID×250 mL, manufactured by DAICEL CHEMICAL INDUSTRIES, LTD., mobile phase: hexane/2-propanol/acetic acid=300/700/1)

D) (3R)-1-(4-((1-(4-(5-chloropyrimidin-2-yl)-2-methylphenyl)-4,4,4-trifluorobutyl)amino)benzoyl)piperidine-3-carboxylic acid To a reaction mixture of ethyl (3R)-1-(4-((1-(4-(5-chloropyrimidin-2-yl)-2-methylphenyl)-4,4,4-trifluorobutyl) amino)benzoyl)piperidine-3-carboxylate (8.88 g), ethanol (30 mL) and tetrahydrofuran (30 mL) was added 1M aqueous sodium hydroxide solution (30.2 ml) at 0° C., and the mixture was stirred at room temperature for 2 hr. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure and the residue was washed with ethyl acetate/diisopropyl ether to give the title compound (6.52 g) as a white solid.

$^1$H NMR (300 MHz, DMSO-$d_6$) δ 1.26-1.45 (1H, m), 1.46-1.69 (2H, m), 1.81-1.99 (3H, m), 2.28-2.64 (6H, m), 2.79-3.07 (2H, m), 3.82 (1H, brs), 3.99-4.15 (1H, m), 4.63-4.80 (1H, m), 6.47 (2H, d, J=8.7 Hz), 6.81 (1H, d, J=7.5 Hz), 7.10 (2H, d, J=8.6 Hz), 7.50 (1H, d, J=8.1 Hz), 8.12 (1H, dd, J=8.2, 1.7 Hz), 8.19 (1H, d, J=1.4 Hz), 8.98 (2H, s), 12.35 (1H, brs).

Anal. Calcd for $C_{28}H_{28}ClF_3N_4O_3$: C, 59.95; H, 5.03; N, 9.99.

Found: C, 59.79; H, 5.27; N, 9.77.

compound with shorter retention time by HPLC (column: CHIRALPAK IC (trade name), 4.6 mmID×250 mmL, manufactured by DAICEL CHEMICAL INDUSTRIES, LTD., mobile phase: hexane/2-propanol/acetic acid=700/300/1)

Example 3

(3R)-1-(4-((4,4,4-trifluoro-1-(2-methyl-4-(5-(trifluoromethyl)pyrimidin-2-yl)phenyl)butyl)amino)benzoyl)piperidine-3-carboxylic acid A) methyl 4-((4,4,4-trifluoro-1-(2-methyl-4-(5-(trifluoromethyl)pyrimidin-2-yl)phenyl)butyl)amino) benzoate A reaction mixture of methyl 4-((4,4,4-trifluoro-1-(2-methyl-4-(4,4,5,5-tetramethyl-1,3,2-dioxaborolan-2-yl)phenyl) butyl)amino)benzoate (5.6 g) obtained in Example 1, step F, 2-chloro-5-(trifluoromethyl)pyrimidine (2.36 g), tetrakistriphenylphosphinepalladium (0.678 g), 2M aqueous sodium carbonate solution (17.6 mL) and dimethoxyethane (52.8 mL) was stirred at 100° C. overnight under a nitrogen atmosphere. The reaction mixture was added to saturated aqueous ammonium chloride solution, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (4.93 g).

MS (ESI–), found: 496.3.

B) 4-((4,4,4-trifluoro-1-(2-methyl-4-(5-(trifluoromethyl)pyrimidin-2-yl)phenyl)butyl)amino)benzoic acid A reaction mixture of methyl 4-((4,4,4-trifluoro-1-(2-methyl-4-(5-(trifluoromethyl)pyrimidin-2-yl)phenyl)butyl) amino)benzoate (4.93 g), 1M aqueous sodium hydroxide solution (39.6 mL), THF (40 mL) and methanol (40 mL) was stirred at 70° C. overnight. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure to give the title compound as a crudely purified product. This compound was used in step C without further purification.

MS (ESI–), found: 482.2.

C) ethyl (3R)-1-(4-((4,4,4-trifluoro-1-(2-methyl-4-(5-(trifluoromethyl)pyrimidin-2-yl)phenyl)butyl) amino)benzoyl)piperidine-3-carboxylate A solution of 4-((4,4,4-trifluoro-1-(2-methyl-4-(5-(trifluoromethyl)pyrimidin-2-yl)phenyl)butyl)amino)benzoic acid, ethyl (3R)-piperidine-3-carboxylate (2.29 mL), 1-hydroxybenzotriazole (2.01 g), 1-ethyl-3-(3-dimethylaminopropyl) carbodiimide hydrochloride (2.85 g) and diisopropylethylamine (2.60 mL) in dimethylformamide (30 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ ethyl acetate) to give the title compound (4.96 g).

MS (ESI+): [M+H]+ 623.2.

compound with longer retention time by HPLC (column: CHIRALPAK AD-3 (trade name), 4.6 mmID×250 mL, manufactured by DAICEL CHEMICAL INDUSTRIES, LTD., mobile phase: hexane/ethanol/diethylamine=700/300/1)

D) (3R)-1-(4-((4,4,4-trifluoro-1-(2-methyl-4-(5-(trifluoromethyl)pyrimidin-2-yl)phenyl)butyl)amino) benzoyl)piperidine-3-carboxylic acid To a reaction mixture of ethyl (3R)-1-(4-((4,4,4-trifluoro-1-(2-methyl-4-(5-(trifluoromethyl)pyrimidin-2-yl)phenyl) butyl)amino)benzoyl)piperidine-3-carboxylate (4.96 g), ethanol (16 ml) and tetrahydrofuran (16 mL) was added 1M aqueous sodium hydroxide solution (15.9 mL) at 0° C., and the mixture was stirred at room temperature overnight. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure and the residue was crystallized from ethyl acetate/diisopropyl ether to give the title compound (4.37 g) as a white solid.

$^1$H NMR (300 MHz, DMSO-$d_6$) δ 1.25-1.70 (3H, m), 1.81-2.05 (3H, m), 2.22-2.62 (6H, m), 2.78-3.08 (2H, m), 3.81 (1H, brs), 3.95-4.23 (1H, m), 4.64-4.81 (1H, m), 6.48 (2H, d, J=8.6 Hz), 6.83 (1H, d, J=7.6 Hz), 7.10 (2H, d, J=8.5 Hz), 7.54 (1H, d, J=8.2 Hz), 8.14-8.35 (2H, m), 9.31 (2H, d, J=0.8 Hz), 12.34 (1H, s).

Anal. Calcd for C₂₉H₂₈F₆N₄O₃: C, 58.58; H, 4.75; N, 9.42. Found: C, 58.42; H, 4.82; N, 9.26.

compound with shorter retention time by HPLC (column: CHIRALPAK AD-3 (trade name), 4.6 mmID×250 mL, manufactured by DAICEL CHEMICAL INDUSTRIES, LTD., mobile phase: hexane/ethanol/TFA=800/200/5)

Example 4

(3R)-1-(4-((1-(4-(5-ethylpyrimidin-2-yl)-2-methylphenyl)-4,4,4-trifluorobutyl)amino)benzoyl)piperidine-3-carboxylic acid A) methyl 4-((1-(4-(5-ethylpyrimidin-2-yl)-2-methylphenyl)-4,4,4-trifluorobutyl)amino)benzoate A reaction mixture of methyl 4-((4,4,4-trifluoro-1-(2-methyl-4-(4,4,5,5-tetramethyl-1,3,2-dioxaborolan-2-yl)phenyl)butyl)amino)benzoate (14.3 g) obtained in Example 1, step F, 2-chloro-5-ethylpyrimidine (4.00 mL), tetrakistriphenylphosphinepalladium (3.46 g), 2M aqueous sodium carbonate solution (44.9 mL) and DME (135 mL) was stirred at 100° C. overnight under a nitrogen atmosphere. The reaction mixture was added to water, and the mixture was extracted with ethyl acetate. The extract was washed with saturated brine, and dried over anhydrous magnesium sulfate. The solvent was evaporated under reduced pressure and the residue was solidified with diisopropyl ether to give the title compound (12.6 g).

MS (ESI+): [M+H]⁺ 458.4.

B) 4-((1-(4-(5-ethylpyrimidin-2-yl)-2-methylphenyl)-4,4,4-trifluorobutyl)amino)benzoic acid A reaction mixture of methyl 4-((1-(4-(5-ethylpyrimidin-2-yl)-2-methylphenyl)-4,4,4-trifluorobutyl)amino)benzoate (12.6 g), 1M aqueous sodium hydroxide solution (82 mL), THF (40 mL) and methanol (40 mL) was stirred at 70° C. for 7 hr. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure to give the title compound as a crudely purified product. This compound was used in step C without further purification.

MS (ESI+): [M+H]⁺ 444.4.

C) ethyl (3R)-1-(4-((1-(4-(5-ethylpyrimidin-2-yl)-2-methylphenyl)-4,4,4-trifluorobutyl)amino)benzoyl)piperidine-3-carboxylate A solution of 4-((1-(4-(5-ethylpyrimidin-2-yl)-2-methylphenyl)-4,4,4-trifluorobutyl)amino)benzoic acid obtained in step B, ethyl (3R)-piperidine-3-carboxylate (5.08 mL), 1-hydroxybenzotriazole (4.46 g), 1-ethyl-3-(3-dimethylaminopropyl)carbodiimide hydrochloride (6.32 g) and diisopropylethylamine (5.76 mL) in dimethylformamide (79 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (15.9 g).

MS (ESI+): [M+H]⁺ 583.6.

compound with shorter retention time by HPLC (column: CHIRALPAK IC (trade name), 4.6 mmID×250 mL, manufactured by DAICEL CHEMICAL INDUSTRIES, LTD., mobile phase: hexane/ethanol=200/800)

D) (3R)-1-(4-((1-(4-(5-ethylpyrimidin-2-yl)-2-methylphenyl)-4,4,4-trifluorobutyl)amino)benzoyl)piperidine-3-carboxylic acid To a reaction mixture of ethyl (3R)-1-(4-((4,4,4-trifluoro-1-(2-methyl-4-(5-(trifluoromethyl)pyridin-2-yl)phenyl)butyl)amino)benzoyl)piperidine-3-carboxylate (15.5 g), ethanol (53 mL) and tetrahydrofuran (53 mL) was added 1M aqueous sodium hydroxide solution (53.2 mL) at 0° C., and the mixture was stirred at room temperature for 3 hr. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure and the residue was crystallized from diethyl ether to give the title compound (13.4 g) as a white solid.

¹H NMR (300 MHz, DMSO-d₆) δ 1.23 (3H, t, J=7.6 Hz), 1.29-1.70 (3H, m), 1.82-2.02 (3H, m), 2.26-2.59 (6H, m), 2.65 (2H, q, J=7.6 Hz), 2.81-3.06 (2H, m), 3.81 (1H, brs), 4.09 (1H, brs), 4.65-4.78 (1H, m), 6.48 (2H, d, J=8.6 Hz), 6.80 (1H, d, J=7.5 Hz), 7.10 (2H, d, J=8.6 Hz), 7.47 (1H, d, J=8.1 Hz), 8.13 (1H, dd, J=8.1, 1.5 Hz), 8.19 (1H, d, J=1.3 Hz), 8.75 (2H, s), 12.35 (1H, brs).

Anal. Calcd for C₃₀H₃₃F₃N₄O₃: C, 64.97; H, 6.00; N, 10.10. Found: C, 64.94; H, 6.17; N, 9.86.

compound with shorter retention time by HPLC (column: CHIRALPAK AD-3 (trade name), 4.6 mmID×250 mL, manufactured by DAICEL CHEMICAL INDUSTRIES, LTD., mobile phase: hexane/ethanol/TFA=700/300/5)

Example 5

(3R)-1-(4-((4,4,4-trifluoro-1-(4'-fluoro-3-methylbiphenyl-4-yl)butyl)amino)benzoyl)piperidine-3-carboxylic acid A) methyl 4-(4,4,4-trifluoro-1-(4'-fluoro-3-methylbiphenyl-4-yl)butylamino)benzoate A reaction mixture of methyl 4-((1-(4-bromo-2-methylphenyl)-4,4,4-trifluorobutyl)amino)benzoate (racemate) (0.55 g) obtained in Example 1, step D, 4-fluorophenylboronic acid (0.215 g), 2M aqueous sodium carbonate solution (1.53 mL), tetrakistriphenylphosphinepalladium (0.074 g) and DME (4 mL) was stirred at 80° C. under a nitrogen atmosphere. The reaction mixture was added to water, and the mixture was extracted with ethyl acetate. The extract was washed with water and saturated brine, dried over anhydrous magnesium sulfate, and the solvent was evaporated under reduced pressure. The residue was purified by silica gel column chromatography (hexane/ethyl acetate) to give the title compound (0.530 g).

MS (ESI−), found: 444.1.

B) (3R)-1-(4-((4,4,4-trifluoro-1-(4'-fluoro-3-methylbiphenyl-4-yl)butyl)amino)benzoyl)piperidine-3-carboxylic acid By a method similar to that in Example 1, steps H to J, the title compound was obtained.

By a method similar to that in Example 5, compounds of the below-mentioned Example 29 and Example 30 were produced.

Example 6

(3R)-1-((6-((4,4,4-trifluoro-1-(4'-fluoro-3-methylbiphenyl-4-yl)butyl)amino)pyridin-3-yl)carbonyl)piperidine-3-carboxylic acid A) methyl 6-((1-(4-bromo-2-methylphenyl)-4,4,4-trifluorobutyl)amino)nicotinate Using methyl 6-aminonicotinate, and by a method similar to that in Example 1, step D, the title compound was obtained.
MS (ESI+): [M+H]⁺ 431.1.

B) (3R)-1-((6-((4,4,4-trifluoro-1-(4'-fluoro-3-methylbiphenyl-4-yl)butyl)amino)pyridin-3-yl)carbonyl)piperidine-3-carboxylic acid By a method similar to that in Example 5, steps A to B, the title compound was obtained.

Example 7

(3R)-1-(4-((4,4,4-trifluoro-1-(4'-methoxy-3-methylbiphenyl-4-yl)butyl)amino)benzoyl)piperidine-3-carboxylic acid A) ethyl (3R)-1-(4-((1-(4-bromo-2-methylphenyl)-4,4,4-trifluorobutyl)amino)benzoyl)piperidine-3-carboxylate Using methyl 4-((1-(4-bromo-2-methylphenyl)-4,4,4-trifluorobutyl)amino)benzoate (racemate) obtained in Example 1, step D, and in the same manner as in Example 1, steps H to I, the title compound was obtained.
MS (ESI+): [M+H]⁺ 555.3.

B) ethyl (3R)-1-(4-((4,4,4-trifluoro-1-(4'-methoxy-3-methylbiphenyl-4-yl)butyl)amino)benzoyl)piperidine-3-carboxylate A reaction mixture of ethyl (3R)-1-(4-((1-(4-bromo-2-methylphenyl)-4,4,4-trifluorobutyl)amino)benzoyl)piperidine-3-carboxylate (200 mg), palladium acetate (4.0 mg), potassium fluoride (62.8 mg), 4-methoxyphenylboronic acid (109 mg), 2-(di-tert-butylphosphino)biphenyl (10.7 mg) and tetrahydrofuran (2 mL) was stirred at room temperature overnight under a nitrogen atmosphere. The reaction mixture was added to water, and the mixture was extracted with ethyl acetate. The extract was washed with water and saturated brine, dried over anhydrous magnesium sulfate, and the solvent was evaporated under reduced pressure. The residue was purified by silica gel column chromatography (hexane/ethyl acetate) to give the title compound (0.173 g).
MS (ESI+): [M+H]⁺ 583.4.

C) (3R)-1-(4-((4,4,4-trifluoro-1-(4'-methoxy-3-methylbiphenyl-4-yl)butyl)amino)benzoyl)piperidine-3-carboxylic acid By a method similar to that in Example 1, step J, the title compound (0.147 g) was obtained.

Example 8

(3R)-1-(4-((1-(4'-cyano-3-methylbiphenyl-4-yl)-4,4,4-trifluorobutyl)amino)benzoyl)piperidine-3-carboxylic acid A) (3R)-1-(4-((1-(4-bromo-2-methylphenyl)-4,4,4-trifluorobutyl)amino)benzoyl)piperidine-3-carboxylic acid Using ethyl (3R)-1-(4-((1-(4-bromo-2-methylphenyl)-4,4,4-trifluorobutyl)amino)benzoyl)piperidine-3-carboxylate obtained in Example 7, step A, and by a method similar to that in Example 1, step J, the title compound was obtained.
MS (ESI+): [M+H]⁺ 527.2.

B) (3R)-1-(4-((1-(4'-cyano-3-methylbiphenyl-4-yl)-4,4,4-trifluorobutyl)amino)benzoyl)piperidine-3-carboxylic acid To (3R)-1-(4-((1-(4-bromo-2-methylphenyl)-4,4,4-trifluorobutyl)amino)benzoyl)piperidine-3-carboxylic acid (42 mg) was added a solution of 4-cyanophenylboronic acid (24 mg) in DME (0.5 mL), polymer-supported triphenylphosphinepalladium(0) (0.1 mg), and a solution of potassium carbonate (16 mg) in water (0.2 mL), and the mixture was stirred at 80° C. overnight. The reaction solution was passed through a filter, and washed twice with THF (2 mL). The solvent was evaporated from the obtained solution by an air blowing apparatus. The residue was purified by HPLC (C18, mobile phase: water/acetonitrile (0.1% TFA-containing system)), and the solvent was evaporated from the obtained solution by an air blowing apparatus. The residue was purified by HPLC (C18, mobile phase: water/acetonitrile (10 mM ammonium acetate-containing system)) to give the title compound (7.8 mg).

By a method similar to that in Example 8, the compounds of the below-mentioned Examples 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 and 62 were produced.

Example 9

(3R)-1-(4-((4,4,4-trifluoro-1-(2-methyl-4-(6-(trifluoromethyl)pyridin-3-yl)phenyl)butyl)amino)benzoyl)piperidine-3-carboxylic acid A) methyl 4-(4,4,4-trifluoro-1-(2-methyl-4-(6-(trifluoromethyl)pyridin-3-yl)phenyl)butylamino)benzoate A reaction mixture of methyl 4-((1-(4-bromo-2-methylphenyl)-4,4,4-trifluorobutyl)amino)benzoate (racemate) (3.6 g) obtained in Example 1, step D, 2-trifluoromethyl-5-pyridineboronic acid (1.76 g), sodium carbonate (2.66 g), tetrakistriphenylphosphinepalladium (0.967 g), DME (24 mL) and water (8 mL) was stirred at 130° C. for 45 min under microwave irradiation under a nitrogen atmosphere. The reaction mixture was added to water, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (3.48 g).
MS (ESI+): [M+H]⁺ 497.2.

B) (3R)-1-(4-((4,4,4-trifluoro-1-(2-methyl-4-(6-(trifluoromethyl)pyridin-3-yl)phenyl)butyl)amino)benzoyl)piperidine-3-carboxylic acid Using methyl 4-(4,4,4-trifluoro-1-(2-methyl-4-(6-(trifluoromethyl)pyridin-3-yl)phenyl)butylamino)benzoate, and by a method similar to that in Example 1, steps H to J, the title compound (3.52 g) was obtained.

By a method similar to that in Example 9, the compounds of the below-mentioned Examples 63, 64, 65, 66, 67, 68, 69, 70, 71, 72, 73, 74, 75, 76, 77, 78, 79, 80, 81, 82, 83 and 84 were produced.

Example 10

(3R)-1-(4-((4,4,4-trifluoro-1-(2-methyl-4-(5-(trifluoromethyl)pyridin-2-yl)phenyl)butyl)amino)benzoyl)piperidine-3-carboxylic acid A) methyl 4-((4,4,4-trifluoro-1-(2-methyl-4-(4,4,5,5-tetramethyl-1,3,2-dioxaborolan-2-yl)phenyl)butyl)amino)benzoate A reaction mixture of methyl 4-((1-(4-bromo-2-methylphenyl)-4,4,4-trifluorobutyl)amino)benzoate (racemate) (3 g) obtained in Example 1, step D, 4,4,4',4',5,5,5',5'-octamethyl-2,2'-bi-1,3,2-dioxaborolane (2.66 g), 1,1'-bis(diphenylphosphino)ferrocene-palladium(II)dichloride-dichloromethane complex (0.287 g), potassium acetate (2.05 g) and DMSO (15 mL) was stirred at 80° C. overnight under a nitrogen atmosphere. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (2.99 g).

MS (ESI−), found: 476.2.

B) methyl 4-(5,5,5-trifluoro-2-(2-methyl-4-(5-(trifluoromethyl)pyridin-2-yl)phenyl)pentyl)benzoate A reaction mixture of methyl 4-((4,4,4-trifluoro-1-(2-methyl-4-(4,4,5,5-tetramethyl-1,3,2-dioxaborolan-2-yl)phenyl)butyl)amino)benzoate (0.500 g), 2-bromo-5-(trifluoromethyl)pyridine (0.284 g), tetrakistriphenylphosphinepalladium (0.121 g), sodium carbonate (0.333 g), DME (3 mL) and water (1 mL) was stirred at 130° C. for 1 hr under microwave irradiation under a nitrogen atmosphere. The reaction mixture was added to water, and the mixture was extracted with ethyl acetate. The extract was washed with saturated brine, and dried over anhydrous magnesium sulfate. The solvent was evaporated under reduced pressure and the residue was purified by silica gel column chromatography (hexane/ethyl acetate) to give the title compound (0.520 g).

MS (ESI+): [M+H]$^+$ 497.2.

C) 4-((4,4,4-trifluoro-1-(2-methyl-4-(5-(trifluoromethyl)pyridin-2-yl)phenyl)butyl)amino)benzoic acid A reaction mixture of methyl 4-(5,5,5-trifluoro-2-(2-methyl-4-(5-(trifluoromethyl)pyridin-2-yl)phenyl)pentyl)benzoate (0.520 g), 1M aqueous sodium hydroxide solution (4.2 mL), THF (4 mL) and methanol (4 mL) was stirred at 70° C. overnight. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure to give the title compound (0.504 g). This compound was used in step D without further purification.

MS (ESI+): [M+H]$^+$ 483.2.

D) ethyl (3R)-1-(4-((4,4,4-trifluoro-1-(2-methyl-4-(5-(trifluoromethyl)pyridin-2-yl)phenyl)butyl)amino)benzoyl)piperidine-3-carboxylate A solution of 4-((4,4,4-trifluoro-1-(2-methyl-4-(5-(trifluoromethyl)pyridin-2-yl)phenyl)butyl)amino)benzoic acid obtained in the aforementioned step C, ethyl (3R)-piperidine-3-carboxylate (0.177 mL), 1-hydroxybenzotriazole monohydrate (0.176 g), 1-ethyl-3-(3-dimethylaminopropyl)carbodiimide hydrochloride (0.220 g) and diisopropylethylamine (0.201 mL) in dimethylformamide (3 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (0.534 g).

MS (ESI+): [M+H]$^+$ 622.3.

E) (3R)-1-(4-((4,4,4-trifluoro-1-(2-methyl-4-(5-(trifluoromethyl)pyridin-2-yl)phenyl)butyl)amino)benzoyl)piperidine-3-carboxylic acid To a reaction mixture of ethyl (3R)-1-(4-((4,4,4-trifluoro-1-(2-methyl-4-(5-(trifluoromethyl)pyridin-2-yl)phenyl)butyl)amino)benzoyl)piperidine-3-carboxylate (0.100 g), ethanol (0.7 mL) and tetrahydrofuran (0.7 mL) was added 1M aqueous sodium hydroxide solution (0.322 mL) at 0° C., and the mixture was stirred at room temperature for 1 hr. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (0.055 g).

$^1$H NMR (300 MHz, DMSO-d$_6$) δ 1.27-1.69 (3H, m), 1.80-1.98 (3H, m), 2.37 (2H, dd, J=9.8, 4.5 Hz), 2.53 (4H, s), 2.82-3.06 (2H, m), 3.81 (1H, brs), 4.01-4.15 (1H, m), 4.65-4.79 (1H, m), 6.48 (2H, d, J=8.3 Hz), 6.80 (1H, d, J=7.6 Hz), 7.10 (2H, d, J=8.7 Hz), 7.50 (1H, d, J=7.9 Hz), 7.93 (1H, dd, J=8.1, 1.7 Hz), 8.01 (1H, d, J=1.5 Hz), 8.11-8.19 (1H, m), 8.21-8.29 (1H, m), 8.95-9.04 (1H, m), 12.33 (1H, brs).

By a method similar to that in Example 10, the compounds of the below-mentioned Examples 85, 86, 87, 88, 89, 90, 91, 92, 93 and 94 were produced.

Example 11

(3R)-1-(4-((4,4,4-trifluoro-1-(2-methyl-4-(5-(trifluoromethyl)pyrimidin-2-yl)phenyl)butyl)amino)benzoyl)piperidine-3-carboxylic acid A) methyl 4-((4,4,4-trifluoro-1-(2-methyl-4-(5-(trifluoromethyl)pyrimidin-2-yl)phenyl)butyl)amino)benzoate A reaction mixture of methyl 4-((4,4,4-trifluoro-1-(2-methyl-4-(4,4,5,5-tetramethyl-1,3,2-dioxaborolan-2-yl)phenyl)

butyl)amino)benzoate (0.300 g) obtained in Example 10, step A, 2-chloro-5-(trifluoromethyl)pyrimidine (0.108 g), tetrakistriphenylphosphinepalladium (0.0726 g), sodium carbonate (0.200 g), DME (3 mL) and water (1 mL) was stirred at 130° C. for 1 hr under microwave irradiation under a nitrogen atmosphere. The reaction mixture was added to water, and the mixture was extracted with ethyl acetate. The extract was washed with saturated brine, and dried over anhydrous magnesium sulfate. The solvent was evaporated under reduced pressure and the residue was purified by silica gel column chromatography (hexane/ethyl acetate) to give the title compound (0.259 g).

MS (ESI−), found: 496.2.

B) 4-((4,4,4-trifluoro-1-(2-methyl-4-(5-(trifluoromethyl)pyrimidin-2-yl)phenyl)butyl)amino)benzoic acid A reaction mixture of methyl 4-((4,4,4-trifluoro-1-(2-methyl-4-(5-(trifluoromethyl)pyrimidin-2-yl)phenyl)butyl)amino)benzoate (0.259 g), 1M aqueous sodium hydroxide solution (2.08 mL), THF (2 mL) and methanol (2 mL) was stirred at 70° C. overnight. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure to give the title compound (0.251 g). This compound was used in step C without further purification.

MS (ESI−), found: 482.1.

C) ethyl (3R)-1-(4-((4,4,4-trifluoro-1-(2-methyl-4-(5-(trifluoromethyl)pyrimidin-2-yl)phenyl)butyl)amino)benzoyl)piperidine-3-carboxylate A solution of 4-((4,4,4-trifluoro-1-(2-methyl-4-(5-(trifluoromethyl)pyrimidin-2-yl)phenyl)butyl)amino)benzoic acid (0.251 g) obtained in the aforementioned step B, ethyl (3R)-piperidine-3-carboxylate (0.088 mL), 1-hydroxybenzotriazole monohydrate (0.087 g), 1-ethyl-3-(3-dimethylaminopropyl)carbodiimide hydrochloride (0.109 g) and diisopropylethylamine (0.100 mL) in dimethylformamide (1.5 mL) was stirred at room temperature overnight. The reaction mixture was added to water, and the mixture was extracted with ethyl acetate. The extract was washed with water and saturated brine, dried over anhydrous magnesium sulfate, and the solvent was evaporated under reduced pressure. The residue was purified by silica gel column chromatography (hexane/ethyl acetate) to give the title compound (0.285 g).

MS (ESI+): [M+H]+ 623.3.

D) (3R)-1-(4-((4,4,4-trifluoro-1-(2-methyl-4-(5-(trifluoromethyl)pyrimidin-2-yl)phenyl)butyl)amino)benzoyl)piperidine-3-carboxylic acid To a reaction mixture of ethyl (3R)-1-(4-((4,4,4-trifluoro-1-(2-methyl-4-(5-(trifluoromethyl)pyridin-2-yl)phenyl)butyl)amino)benzoyl)piperidine-3-carboxylate (0.285 g), ethanol (1 mL) and tetrahydrofuran (1 mL) was added 1M aqueous sodium hydroxide solution (0.917 mL) at 0° C., and the mixture was stirred at room temperature for 1 hr. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (0.252 g).

$^1$H NMR (300 MHz, DMSO-d$_6$) δ 1.27-1.69 (3H, m), 1.81-2.01 (3H, m), 2.24-2.64 (6H, m), 2.79-3.07 (2H, m), 3.82 (1H, brs), 4.06 (1H, brs), 4.66-4.80 (1H, m), 6.48 (2H, d, J=8.3 Hz), 6.82 (1H, d, J=7.6 Hz), 7.10 (2H, d, J=8.7 Hz), 7.54 (1H, d, J=8.3 Hz), 8.18-8.26 (1H, m), 8.29 (1H, d, J=1.1 Hz), 9.30 (2H, d, J=0.8 Hz), 12.36 (1H, brs).

Example 12

(3R)-1-(4-((1-(4-(5-chloropyrimidin-2-yl)-2-methylphenyl)-4,4,4-trifluorobutyl)amino)benzoyl)piperidine-3-carboxylic acid

A) 4-((1-(4-bromo-2-methylphenyl)-4,4,4-trifluorobutyl)amino)benzoic acid

A reaction mixture of methyl 4-((1-(4-bromo-2-methylphenyl)-4,4,4-trifluorobutyl)amino)benzoate (racemate) (4 g) obtained in Example 1, step D, 1M aqueous sodium hydroxide solution (37.2 mL), THF (37 mL) and methanol (37 mL) was stirred at 70° C. overnight. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure to give the title compound. This compound was used in step B without further purification.

B) 4-((4,4,4-trifluoro-1-(2-methyl-4-(4,4,5,5-tetramethyl-1,3,2-dioxaborolan-2-yl)phenyl)butyl)amino)benzoic acid A reaction mixture of 4-((1-(4-bromo-2-methylphenyl)-4,4,4-trifluorobutyl)amino)benzoic acid (3.87 g) obtained in the aforementioned step A, 4,4,4',4',5,5,5',5'-octamethyl-2,2'-bi-1,3,2-dioxaborolane (3.54 g), 1,1'-bis(diphenylphosphino)ferrocene-palladium(II)dichloride-dichloromethane complex (0.383 g), potassium acetate (3.65 g) and DMSO (20 mL) was stirred at 90° C. under a nitrogen atmosphere. The insoluble material was filtered off through celite. The filtrate was poured into water, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (3.50 g).

MS (ESI−), found: 462.2.

C) 4-((1-(4-(5-chloropyrimidin-2-yl)-2-methylphenyl)-4,4,4-trifluorobutyl)amino)benzoic acid A reaction mixture of 4-((4,4,4-trifluoro-1-(2-methyl-4-(4,4,5,5-tetramethyl-1,3,2-dioxaborolan-2-yl)phenyl)butyl)amino)benzoic acid (0.500 g), 2-bromo-5-chloropyrimidine (0.251 g), tetrakistriphenylphosphinepalladium (0.125 g), sodium carbonate (0.343 g), DME (3 mL) and water (1 mL) was stirred at 130° C. for 1 hr under microwave irradiation under a nitrogen atmosphere. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (0.407 g).

MS (ESI+): [M+H]+ 450.1.

D) ethyl (3R)-1-(4-((1-(4-(5-chloropyrimidin-2-yl)-2-methylphenyl)-4,4,4-trifluorobutyl)amino)benzoyl)piperidine-3-carboxylate A solution of 4-((1-(4-(5-chloropyrimidin-2-yl)-2-methylphenyl)-4,4,4-trifluorobutyl)amino)benzoic acid (0.407 g), ethyl (3R)-piperidine-3-carboxylate (0.153 mL), 1-hydroxybenzotriazole monohydrate (0.152 g), 1-ethyl-3-(3-dimethylaminopropyl)carbodiimide hydrochloride (0.191 g) and diisopropylethylamine (0.174 mL) in dimethylformamide (3 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (0.419 g).
MS (ESI+): [M+H]$^+$ 589.3.

E) (3R)-1-(4-((1-(4-(5-chloropyrimidin-2-yl)-2-methylphenyl)-4,4,4-trifluorobutyl)amino)benzoyl)piperidine-3-carboxylic acid To a reaction mixture of ethyl (3R)-1-(4-((1-(4-(5-chloropyrimidin-2-yl)-2-methylphenyl)-4,4,4-trifluorobutyl)amino)benzoyl)piperidine-3-carboxylate (0.414 g), ethanol (1.4 mL) and tetrahydrofuran (1.4 mL) was added 1M aqueous sodium hydroxide solution (1.4 mL) at 0° C., and the mixture was stirred at room temperature for 3 hr. The reaction mixture was neutralized with 1M hydrochloric acid at 0° C., and extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (0.348 g).
$^1$H NMR (300 MHz, DMSO-d$_6$) δ 1.28-1.71 (3H, m), 1.90 (3H, d, J=6.8 Hz), 2.29-2.65 (6H, m), 2.83-3.05 (2H, m), 3.81 (1H, brs), 4.09 (1H, brs), 4.71 (1H, d, J=6.0 Hz), 6.47 (2H, d, J=8.3 Hz), 6.80 (1H, d, J=7.6 Hz), 7.10 (2H, d, J=8.7 Hz), 7.49 (1H, d, J=7.9 Hz), 8.07-8.21 (2H, m), 8.98 (2H, s), 12.28 (1H, brs).

Example 13

(3R)-1-(4-((1-(4-(5-ethylpyrimidin-2-yl)-2-methylphenyl)-4,4,4-trifluorobutyl)amino)benzoyl)piperidine-3-carboxylic acid

A) methyl 4-((1-(4-(5-ethylpyrimidin-2-yl)-2-methylphenyl)-4,4,4-trifluorobutyl)amino)benzoate A reaction mixture of methyl 4-((4,4,4-trifluoro-1-(2-methyl-4-(4,4,5,5-tetramethyl-1,3,2-dioxaborolan-2-yl)phenyl)butyl)amino)benzoate (0.600 g) obtained in Example 10, step A, 2-chloro-5-ethylpyrimidine (0.215 g), tetrakistriphenylphosphinepalladium (0.145 g), sodium carbonate (0.400 g), DME (3 mL) and water (1 ml) was stirred at 130° C. for 1 hr under microwave irradiation under a nitrogen atmosphere. The reaction mixture was added to water, and the mixture was extracted with ethyl acetate. The extract was washed with saturated brine, and dried over anhydrous magnesium sulfate. The solvent was evaporated under reduced pressure and the residue was purified by silica gel column chromatography (hexane/ethyl acetate) to give the title compound (0.507 g).
$^1$H NMR (300 MHz, DMSO-d$_6$) δ 1.23 (3H, t, J=7.6 Hz), 1.91 (2H, d, J=6.8 Hz), 2.35-2.58 (8H, m), 2.64 (2H, q, J=7.7 Hz), 4.74 (1H, d, J=5.7 Hz), 6.47 (2H, d, J=8.3 Hz), 6.94 (1H, brs), 7.44 (1H, d, J=8.3 Hz), 7.59 (2H, d, J=8.7 Hz), 8.05-8.23 (2H, m), 8.74 (2H, s).

B) 4-((1-(4-(5-ethylpyrimidin-2-yl)-2-methylphenyl)-4,4,4-trifluorobutyl)amino)benzoic acid A reaction mixture of methyl 4-((1-(4-(5-ethylpyrimidin-2-yl)-2-methylphenyl)-4,4,4-trifluorobutyl)amino)benzoate (0.507 g), 1M aqueous sodium hydroxide solution (4.43 mL), THF (4.4 mL) and methanol (4.4 mL) was stirred at 70° C. overnight. The reaction mixture was neutralized with 1M hydrochloric acid at 0° C., and extracted with ethyl acetate. The extract was washed with water and then saturated brine, and dried over anhydrous magnesium sulfate. The solvent was evaporated under reduced pressure to give the title compound (0.486 g). This compound was used in step C without further purification.
MS (ESI+): [M+H]$^+$ 444.2.

C) ethyl (3R)-1-(4-((1-(4-(5-ethylpyrimidin-2-yl)-2-methylphenyl)-4,4,4-trifluorobutyl)amino)benzoyl)piperidine-3-carboxylate A solution of 4-((1-(4-(5-ethylpyrimidin-2-yl)-2-methylphenyl)-4,4,4-trifluorobutyl)amino)benzoic acid, ethyl (3R)-piperidine-3-carboxylate (0.186 mL), 1-hydroxybenzotriazole monohydrate (0.185 g), 1-ethyl-3-(3-dimethylaminopropyl)carbodiimide hydrochloride (0.231 g) and diisopropylethylamine (0.211 mL) in dimethylformamide (3 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure and the residue was purified by silica gel column chromatography (hexane/ethyl acetate) to give the title compound (0.574 g).
MS (ESI+): [M+H]$^+$ 583.3.

D) (3R)-1-(4-((1-(4-(5-ethylpyrimidin-2-yl)-2-methylphenyl)-4,4,4-trifluorobutyl)amino)benzoyl)piperidine-3-carboxylic acid To a reaction mixture of ethyl (3R)-1-(4-((4,4,4-trifluoro-1-(2-methyl-4-(5-(trifluoromethyl)pyridin-2-yl)phenyl)butyl)amino)benzoyl)piperidine-3-carboxylate (0.051 g), ethanol (0.5 mL) and tetrahydrofuran (0.5 mL) was added 1M aqueous sodium hydroxide solution (0.088 mL) at 0° C., and the mixture was stirred at room temperature for 2 hr. The reaction mixture was neutralized with 1M hydrochloric acid at 0° C., and extracted with ethyl acetate. The extract was washed with water and then saturated brine, and dried over anhydrous magnesium sulfate. The solvent was evaporated under reduced pressure and the residue was purified by silica gel column chromatography (hexane/ethyl acetate) to give the title compound (0.042 g).
$^1$H NMR (300 MHz, DMSO-d$_6$) δ 1.23 (3H, t, J=7.6 Hz), 1.37 (1H, d, J=9.4 Hz), 1.47-1.69 (2H, m), 1.79-2.02 (3H, m), 2.24-2.56 (6H, m), 2.65 (2H, q, J=7.6 Hz), 2.82-3.07 (2H, m), 3.83 (1H, brs), 4.06 (1H, brs), 4.70 (1H, d, J=6.0 Hz), 6.48 (2H, d, J=8.7 Hz), 6.78 (1H, d, J=7.6 Hz), 7.10 (2H, d, J=8.3 Hz), 7.47 (1H, d, J=8.3 Hz), 8.12 (1H, d, J=8.3 Hz), 8.19 (1H, s), 8.74 (2H, s), 12.32 (1H, brs).

Example 14

(3R)-1-(4-((4,4,4-trifluoro-1-(2-methyl-4-(6-(trifluoromethyl)pyridin-3-yl)phenyl)butyl)amino)benzoyl)piperidine-3-carboxylic acid Racemate (120 mg) of (3R)-1-(4-((4,4,4-trifluoro-1-(2-methyl-4-(6-(trifluoromethyl)pyridin-3-yl)phenyl)butyl)amino)benzoyl)piperidine-3-carboxylic acid obtained in Example 9 was fractionated by SFC (column: CHIRALPAK IA (trade name), 20 mmID×250 mL, manufactured by DAICEL CHEMICAL INDUSTRIES, LTD., mobile phase: carbon dioxide/methanol/diethylamine=740/260/2) to give the title compound (59 mg) with shorter retention time.

compound with shorter retention time by SFC (column: CHIRALPAK IA (trade name), 4.6 mmID×150 mL, manufactured by DAICEL CHEMICAL INDUSTRIES, LTD., mobile phase: carbon dioxide/methanol/TFA=740/260/3)

Example 15

(3R)-1-((6-((1-(4'-chloro-3-methylbiphenyl-4-yl)-4,4,4-trifluorobutyl)amino)pyridin-3-yl)carbonyl)piperidine-3-carboxylic acid Using methyl 6-((1-(4-bromo-2-methylphenyl)-4,4,4-trifluorobutyl)amino)nicotinate obtained in Example 6, step A, and by a method similar to that in Example 9, the title compound was obtained.

Example 16

(3R)-1-(4-(((4'-chloro-3-methylbiphenyl-4-yl)(cyclohexyl)methyl)amino)benzoyl)piperidine-3-carboxylic acid

A) (4-bromo-2-methylphenyl)(cyclohexyl)methanol

Using cyclohexylmagnesium bromide, and in the same manner as in Example 1, step B, the title compound was obtained.

$^1$H NMR (300 MHz, DMSO-$d_6$) δ 0.94-1.13 (4H, m), 1.21-1.85 (7H, m), 2.25 (3H, s), 4.43 (1H, dd, J=6.0, 4.5 Hz), 5.00 (1H, d, J=4.5 Hz), 7.22-7.40 (3H, m).

B) 4-bromo-1-(chloro(cyclohexyl)methyl)-2-methylbenzene

In the same manner as in Example 1, step C, the title compound was obtained.

$^1$H NMR (300 MHz, DMSO-$d_6$) δ 0.81-0.98 (1H, m), 1.04-1.36 (5H, m), 1.60 (2H, d, J=9.1 Hz), 1.75 (1H, d, J=12.5 Hz), 1.86-2.01 (1H, m), 2.13 (1H, d, J=12.5 Hz), 2.33 (3H, s), 5.02 (1H, d, J=9.1 Hz), 7.35-7.46 (3H, m).

C) methyl 4-(((4-bromo-2-methylphenyl)(cyclohexyl)methyl)amino)benzoate

In the same manner as in Example 1, step D, the title compound was obtained.
MS (ESI+): [M+H]$^+$ 416.0.

D) (3R)-1-(((4'-chloro-3-methylbiphenyl-4-yl)(cyclohexyl)methyl)amino)benzoyl)piperidine-3-carboxylic acid In the same manner as in Example 9, the title compound was obtained.

Example 17

(3R)-1-((6-(((4'-chloro-3-methylbiphenyl-4-yl) (cyclohexyl)methyl)amino)pyridin-3-yl)carbonyl)piperidine-3-carboxylic acid

A) methyl 6-(((4-bromo-2-methylphenyl)(cyclohexyl)methyl)amino)nicotinate

Using 4-bromo-1-(chloro(cyclohexyl)methyl)-2-methylbenzene obtained in Example 16, step B and methyl 6-aminonicotinate, and in the same manner as in Example 1, step D, the title compound was obtained.
MS (ESI+): [M+H]$^+$ 417.2.

B) (3R)-1-((6-(((4'-chloro-3-methylbiphenyl-4-yl)(cyclohexyl)methyl)amino)pyridin-3-yl)carbonyl)piperidine-3-carboxylic acid In the same manner as in Example 9, the title compound was obtained.

Example 18

(3R)-1-(4-((1-(4'-chloro-2,6-dimethylbiphenyl-4-yl)-4,4,4-trifluorobutyl)amino)benzoyl)piperidine-3-carboxylic acid

A) 4-formyl-2,6-dimethylphenyl trifluoromethanesulfonate

To a solution of 4-hydroxy-3,5-dimethylbenzaldehyde (2 g) in pyridine (30 mL) was added a solution (5 mL) of trifluoromethanesulfonic acid anhydride (2.92 ml) in toluene at 0° C. The reaction mixture was stirred at room temperature for 30 min, concentrated, and then azeotropically distilled with toluene. To the residue was added 1M hydrochloric acid, and the mixture was extracted with ethyl acetate. The extract was washed with water, saturated aqueous sodium hydrogen carbonate solution and saturated brine, and dried over anhydrous magnesium sulfate. The solvent was evaporated under reduced pressure and the residue was purified by silica gel column chromatography (ethyl acetate/hexane) to give the title compound (2.17 g).

$^1$H NMR (300 MHz, DMSO-$d_6$) δ 2.43 (6H, s), 7.85 (2H, s), 9.98 (1H, s).

B) 4'-chloro-2,6-dimethylbiphenyl-4-carbaldehyde

A reaction mixture of 4-formyl-2,6-dimethylphenyl trifluoromethanesulfonate (2.17 g), 4-chlorophenylboronic acid (1.80 g), tris(dibenzylideneacetone)dipalladium (0.282 g), 2,6-dimethoxy-2'-(dicyclohexylphosphino)biphenyl (0.505 g), sodium carbonate (2.45 g), toluene (34.5 mL) and water (11.5 mL) was stirred at 100° C. overnight under a nitrogen atmosphere. The insoluble material was filtered off through celite, and the filtrate was extracted with ethyl acetate. The extract was washed with saturated brine, and dried over anhydrous magnesium sulfate. The solvent was evaporated under reduced pressure and the residue was purified by silica gel column chromatography (hexane/ethyl acetate) to give the title compound.
$^1$H NMR (300 MHz, DMSO-d$_6$) δ 2.05 (6H, s), 7.22 (2H, d, J=8.7 Hz), 7.56 (2H, d, J=8.7 Hz), 7.68 (2H, s), 9.98 (1H, s).

C) (3R)-1-(4-((1-(4'-chloro-2,6-dimethylbiphenyl-4-yl)-4,4,4-trifluorobutyl)amino)benzoyl)piperidine-3-carboxylic acid Using 4'-chloro-2,6-dimethylbiphenyl-4-carbaldehyde obtained in step B, and in the same manner as in Example 1, steps B, C, D, H, I and J, the title compound was obtained.
By a method similar to that in Example 18, the compound of the below-mentioned Example 95 was produced.

Example 19

(3R)-1-(4-((4,4,4-trifluoro-1-(4-(3-isopropyl-1H-pyrazol-1-yl)-2-methylphenyl)butyl)amino)benzoyl)piperidine-3-carboxylic acid A) methyl 4-((4,4,4-trifluoro-1-(4-(3-isopropyl-1H-pyrazol-1-yl)-2-methylphenyl)butyl)amino)benzoate Under a nitrogen atmosphere, a mixture of methyl 4-((1-(4-bromo-2-methylphenyl)-4,4,4-trifluorobutyl)amino)benzoate (racemate) (400 mg), 3-isopropylpyrazole (154 mg), copper(I) iodide (212 mg), trans-N,N'-dimethylcyclohexane-1,2-diamine (0.352 mL), potassium carbonate (385 mg) and toluene (1.8 mL) was stirred at 110° C. overnight, water was added at room temperature, and the insoluble material was filtered off through celite. The filtrate was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (316.2 mg).
MS (ESI+): [M+H]$^+$ 460.2.

B) ethyl (3R)-1-(4-((4,4,4-trifluoro-1-(4-(3-isopropyl-1H-pyrazol-1-yl)-2-methylphenyl)butyl)amino)benzoyl)piperidine-3-carboxylate By a method similar to that in Example 1, steps H to I, the title compound was obtained.
MS (ESI+): [M+H]$^+$ 557.3.

C) (3R)-1-(4-((4,4,4-trifluoro-1-(4-(3-isopropyl-1H-pyrazol-1-yl)-2-methylphenyl)butyl)amino)benzoyl)piperidine-3-carboxylic acid By a method similar to that in Example 1, step J, the title compound was obtained.
By a method similar to that in Example 19, the compounds of the below-mentioned Examples 96, 97, 98, 99, 100, 101, 102, 103, 104, 105, 106, 107 and 108 were produced.

Example 20

(3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylic acid A) methyl 4-((4,4,4-trifluoro-1-(2-methyl-4-(4,5,6,7-tetrahydro-2H-indazol-2-yl)phenyl)butyl)amino)benzoate Under a nitrogen atmosphere, a mixture of methyl 4-((1-(4-bromo-2-methylphenyl)-4,4,4-trifluorobutyl)amino)benzoate (racemate) (300 mg), 4,5,6,7-tetrahydroindazole (128 mg), copper(I) iodide (159 mg), trans-N,N'-dimethylcyclohexane-1,2-diamine (0.264 mL), potassium carbonate (289 mg) and toluene (1.4 mL) was stirred at 110° C. overnight. To the reaction mixture was added water at room temperature, and the insoluble material was filtered off through celite. The filtrate was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (243.9 mg).
MS (ESI+): [M+H]$^+$ 472.2.

B) 4-((4,4,4-trifluoro-1-(2-methyl-4-(4,5,6,7-tetrahydro-2H-indazol-2-yl)phenyl)butyl)amino)benzoic acid To a mixture of methyl 4-((4,4,4-trifluoro-1-(2-methyl-4-(4,5,6,7-tetrahydro-2H-indazol-2-yl)phenyl)butyl)amino)benzoate (243.9 mg), THF (1.0 ml) and methanol (1.0 mL) was added 1M aqueous sodium hydroxide solution (1.035 mL), and the mixture was stirred at 50° C. overnight. To the reaction mixture was added 1M hydrochloric acid (1.1 mL), and the mixture was extracted with ethyl acetate. The extract was washed with water and saturated brine, and dried over anhydrous magnesium sulfate. The solvent was evaporated under reduced pressure to give the title compound as a crudely purified product. This compound was used in step C without further purification.
MS (ESI+): [M+H]$^+$ 458.2.

C) ethyl (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylate A mixture of 4-((4,4,4-trifluoro-1-(2-methyl-4-(4,5,6,7-tetrahydro-2H-indazol-2-yl)phenyl)butyl)amino)benzoic acid obtained in step B, ethyl (3R)-piperidine-3-carboxylate (0.157 mL), 1-(3-dimethylaminopropyl)-3-ethylcarbodiimide hydrochloride (158 mg), 1-hydroxybenzotriazole monohydrate (156 mg), N,N-diisopropylethylamine (0.267 mL), 4-dimethylaminopyridine (6.21 mg) and DMF (1.2 mL) was stirred at room temperature overnight. To the reaction mixture was added water, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (155.4 mg).
MS (ESI+): [M+H]$^+$ 597.4.

D) (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylic acid To a mixture of ethyl (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylate (155.4 mg), THF (0.5 mL) and ethanol (0.5 mL) was added 1M aqueous sodium hydroxide solution (0.521 mL), and the mixture was stirred at room temperature for 1 hr. To the reaction mixture was added 1M hydrochloric acid (0.6 and the mixture was extracted with ethyl acetate. The extract was washed with water and saturated brine, and dried over anhydrous magnesium sulfate. The solvent was evaporated under reduced pressure to give the title compound (131.6 mg).

¹H NMR (300 MHz, DMSO-d$_6$) δ 1.28-2.10 (10H, m), 2.28-2.69 (10H, m), 2.80-3.11 (2H, m), 3.71-3.92 (1H, m), 3.96-4.22 (1H, m), 4.53-4.76 (1H, m), 6.47 (2H, d, J=8.7 Hz), 6.74 (1H, d, J=7.5 Hz), 7.10 (2H, d, J=8.3 Hz), 7.30-7.41 (1H, m), 7.44-7.52 (1H, m), 7.58 (1H, d, J=1.9 Hz), 8.06 (1H, s), 12.35 (1H, brs).

Example 21

(3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylic acid A) methyl 4-((4,4,4-trifluoro-1-(2-methyl-4-(4,5,6,7-tetrahydro-2H-indazol-2-yl)phenyl)butyl)amino)benzoate Under a nitrogen atmosphere, a mixture of methyl 4-((1-(4-bromo-2-methylphenyl)-4,4,4-trifluorobutyl)amino)benzoate (optically active form, compound with longer retention time) (3.0 g), 4,5,6,7-tetrahydroindazole (1.278 g), copper(I) iodide (1.594 g), trans-N,N'-dimethylcyclohexane-1,2-diamine (2.64 mL), cesium carbonate (6.82 g) and toluene (17.4 mL) was stirred at 110° C. for 18 hr. To the reaction mixture was added water at room temperature, and the insoluble material was filtered off through celite. The filtrate was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (2.11 g).

MS (ESI+): [M+H]$^+$ 472.5.

B) 4-((4,4,4-trifluoro-1-(2-methyl-4-(4,5,6,7-tetrahydro-2H-indazol-2-yl)phenyl)butyl)amino)benzoic acid To a mixture of methyl 4-((4,4,4-trifluoro-1-(2-methyl-4-(4,5,6,7-tetrahydro-2H-indazol-2-yl)phenyl)butyl)amino)benzoate (8.01 g), THF (34 mL) and methanol (34 mL) was added 1M aqueous sodium hydroxide solution (68 mL), and the mixture was stirred at 50° C. overnight. To the reaction mixture was added THF (34 ml), and the mixture was stirred at 60° C. for 7 hr. The reaction mixture was neutralized with 1M hydrochloric acid (68 mL), and extracted with ethyl acetate. The extract was washed with saturated brine, and dried over anhydrous magnesium sulfate. The solvent was evaporated under reduced pressure to give the title compound as a crudely purified product. This compound was used in step C without further purification.

MS (ESI+): [M+H]$^+$ 458.4.

C) ethyl (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylate A mixture of 4-((4,4,4-trifluoro-1-(2-methyl-4-(4,5,6,7-tetrahydro-2H-indazol-2-yl)phenyl)butyl)amino)benzoic acid, ethyl (3R)-piperidine-3-carboxylate (5.24 mL), 1-(3-dimethylaminopropyl)-3-ethylcarbodiimide hydrochloride (6.51 g), 1-hydroxybenzotriazole (4.59 g), N,N-diisopropylethylamine (8.90 mL), 4-dimethylaminopyridine (0.208 g) and DMF (42.5 ml) was stirred at room temperature overnight. To the reaction mixture was added water, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (9.61 g).

MS (ESI+): [M+H]$^+$ 597.7.

D) (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylic acid To a mixture of ethyl (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylate (9.61 g), THF (32 mL) and ethanol (32 mL) was added 1M aqueous sodium hydroxide solution (32.2 mL), and the mixture was stirred at room temperature for 2 hr. The solvent was evaporated under reduced pressure, the reaction mixture was neutralized with 1M hydrochloric acid (32.2 mL), and the mixture was extracted with ethyl acetate. The extract was washed with saturated brine, and dried over anhydrous magnesium sulfate. The solvent was evaporated under reduced pressure to give the title compound as a crudely purified product. The crudely purified product obtained here and separately synthesized crudely purified product (1.68 g) were combined, and recrystallized from a mixed solvent of ethyl acetate-hexane to give the title compound (8.49 g).

¹H NMR (400 MHz, DMSO-d$_6$) δ 1.20-2.08 (10H, m), 2.28-2.74 (10H, m), 2.82-3.09 (2H, m), 3.70-3.93 (1H, m), 3.96-4.18 (1H, m), 4.50-4.74 (1H, m), 6.47 (2H, d, J=8.4 Hz), 6.73 (1H, d, J=7.5 Hz), 7.10 (2H, d, J=8.4 Hz), 7.37 (1H, d, J=8.4 Hz), 7.48 (1H, d, J=8.0 Hz), 7.57 (1H, s), 8.05 (1H, s), 12.36 (1H, brs).

compound with shorter retention time by SFC (column: CHIRALCEL ODH (trade name), 4.6 mmID×150 mL, manufactured by DAICEL CHEMICAL INDUSTRIES, LTD., mobile phase: carbon dioxide/methanol/TFA=740/260/3)

Example 22

(3R)-1-(4-((4,4,4-trifluoro-1-(4-(3-isopropyl-1H-pyrazol-1-yl)-2-methylphenyl)butyl)amino)benzoyl)piperidine-3-carboxylic acid A) ethyl (3R)-1-(4-((4,4,4-trifluoro-1-(4-(3-isopropyl-1H-pyrazol-1-yl)-2-methylphenyl)butyl)amino)benzoyl)piperidine-3-carboxylate Racemate of ethyl (3R)-1-(4-((4,4,4-trifluoro-1-(4-(3-isopropyl-1H-pyrazol-1-yl)-2-methylphenyl)butyl)amino)benzoyl)piperidine-3-carboxylate (9300 mg) was fractionated by HPLC (column: CHIRALCEL OD (trade name), 50 mmID×500 mL, manufactured by DAICEL CHEMICAL INDUSTRIES, LTD., mobile phase: hexane/ethanol=850/150) to give the title compound (3870 mg) with shorter retention time.

MS (ESI+): [M+H]$^+$ 585.2.

compound with shorter retention time by HPLC (column: CHIRALCEL OD (trade name), 4.6 mmID×250 mL, manufactured by DAICEL CHEMICAL INDUSTRIES, LTD., mobile phase: hexane/ethanol=850/150)

B) (3R)-1-(4-((4,4,4-trifluoro-1-(4-(3-isopropyl-1H-pyrazol-1-yl)-2-methylphenyl)butyl)amino)benzoyl)piperidine-3-carboxylic acid By a method similar to that in Example 1, step J, the title compound was obtained.

Example 23

(3R)-1-(4-((1-(4-(5-tert-butyl-1,3-oxazol-2-yl)-2-methylphenyl)-4,4,4-trifluorobutyl)amino)benzoyl)piperidine-3-carboxylic acid A) 3-methyl-4-(4,4,4-trifluoro-1-((4-(methoxycarbonyl)phenyl)amino)butyl)benzoic acid Under a nitrogen atmosphere, to a mixture of methyl 4-((1-(4-bromo-2-methylphenyl)-4,4,4-trifluorobutyl)amino)benzoate (racemate) (1.5 g), 1,1'-bis(diphenylphosphino)ferrocene-palladium(II)dichloride dichloromethane complex (0.285 g), N,N-diisopropylethylamine (3.65 mL), lithium acetate 2 hydrate (2.85 g) and DMF (17 mL) was added acetic anhydride (1.977 mL), and the mixture was stirred at 120° C. overnight. To the reaction mixture was added water at room temperature, and the insoluble material was filtered off through celite. The filtrate was extracted with ethyl acetate, and the extract was washed with 1M hydrochloric acid and saturated brine, and dried over anhydrous magnesium sulfate. The solvent was evaporated under reduced pressure and the residue was purified by silica gel column chromatography (ethyl acetate/hexane) to give the title compound (725.6 mg).

MS (ESI+): [M+H]$^+$ 396.1.

B) methyl 4-((4,4,4-trifluoro-1-(4-((2-hydroxy-3,3-dimethylbutyl)carbamoyl)-2-methylphenyl)butyl)amino)benzoate A mixture of 3-methyl-4-(4,4,4-trifluoro-1-((4-(methoxycarbonyl)phenyl)amino)butyl)benzoic acid (725.6 mg), 1-amino-3,3-dimethylbutan-2-ol (430 mg), 1-(3-dimethylaminopropyl)-3-ethylcarbodiimide hydrochloride (704 mg), 1-hydroxybenzotriazole monohydrate (562 mg), N,N-diisopropylethylamine (0.962 mL), 4-dimethylaminopyridine (22.42 mg) and DMF (4.5 mL) was stirred at room temperature overnight, and water was added. The mixture was extracted with ethyl acetate, and the extract was washed with water and saturated brine, and dried over anhydrous magnesium sulfate.

The solvent was evaporated under reduced pressure and the residue was purified by silica gel column chromatography (ethyl acetate/hexane) to give the title compound (479.1 mg).

MS (ESI+): [M+H]$^+$ 495.3.

C) methyl 4-((1-(4-((3,3-dimethyl-2-oxobutyl)carbamoyl)-2-methylphenyl)-4,4,4-trifluorobutyl)amino)benzoate To a mixture of methyl 4-((4,4,4-trifluoro-1-(4-((2-hydroxy-3,3-dimethylbutyl)carbamoyl)-2-methylphenyl)butyl)amino)benzoate (479.1 mg) and ethyl acetate (10 mL) was added Dess-Martin Periodinane (616 mg) at room temperature, and the mixture was stirred overnight. To the reaction mixture were added saturated aqueous sodium hydrogen carbonate solution and saturated aqueous sodium thiosulfate solution, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (433.8 mg).

MS (ESI+): [M+H]$^+$ 493.3.

D) methyl 4-((1-(4-(5-tert-butyl-1,3-oxazol-2-yl)-2-methylphenyl)-4,4,4-trifluorobutyl)amino)benzoate To methyl 4-((1-(4-((3,3-dimethyl-2-oxobutyl)carbamoyl)-2-methylphenyl)-4,4,4-trifluorobutyl)amino)benzoate (200 mg) was added phosphoryl chloride (0.5 ml) at room temperature. The reaction mixture was heated at 90° C. for 1 hr, and water was added at room temperature. The filtrate was extracted with ethyl acetate, and the extract was washed with 1M aqueous sodium hydroxide solution and saturated brine, and dried over anhydrous magnesium sulfate. The solvent was evaporated and the residue was purified by silica gel column chromatography (ethyl acetate/hexane) to give the title compound (155.4 mg).

MS (ESI+): [M+H]$^+$ 475.2.

E) (3R)-1-(4-((1-(4-(5-tert-butyl-1,3-oxazol-2-yl)-2-methylphenyl)-4,4,4-trifluorobutyl)amino)benzoyl)piperidine-3-carboxylic acid By a method similar to that in Example 1, steps H to J, the title compound was obtained.

By a method similar to that in Example 23, the compounds of the below-mentioned Examples 109 and 110 were produced.

Example 24

(3R)-1-(4-(((4'-chlorobiphenyl-4-yl)(cyclohexyl)methyl)amino)benzoyl)piperidine-3-carboxylic acid A) (4'-chlorobiphenyl-4-yl)(cyclohexyl)methanone To a mixture of 4-chlorobiphenyl (1.0 g), cyclohexanecarbonyl chloride (0.788 mL) and nitromethane (10.6 mL) was added aluminum chloride (0.848 g) at 0° C. The reaction mixture was stirred at 0° C. for 3 hr, and water was added at 0° C. The mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (0.792 g).

$^1$H NMR (400 MHz, DMSO-$d_6$) δ 1.14-1.26 (1H, m), 1.28-1.52 (4H, m), 1.64-1.87 (5H, m), 3.37-3.50 (1H, m), 7.56 (2H, d, J=8.5 Hz), 7.74-7.87 (4H, m), 8.04 (2H, d, J=8.2 Hz).

B) (4'-chlorobiphenyl-4-yl)(cyclohexyl)methanol

To a mixture of (4'-chlorobiphenyl-4-yl)(cyclohexyl)methanone (792.1 mg), THF (5.68 mL) and methanol (0.947 mL) was added sodium borohydride (120 mg) at 0° C. The reaction mixture was stirred at room temperature for 2 hr, and saturated aqueous sodium hydrogen carbonate solution was added at 0° C. The mixture was extracted with ethyl acetate, and the extract was washed with water and saturated brine, and dried over anhydrous magnesium sulfate. The solvent was evaporated under reduced pressure to give the title compound as a crudely purified product. This compound was used in step C without further purification.

$^1$H NMR (400 MHz, DMSO-$d_6$) δ 0.90-1.21 (5H, m), 1.37 (1H, d, J=10.5 Hz), 1.43-1.53 (1H, m), 1.55-1.76 (3H, m), 1.84 (1H, d, J=11.2 Hz), 4.28 (1H, t, J=5.1 Hz), 5.09 (1H, d, J=4.1 Hz), 7.35 (2H, d, J=8.0 Hz), 7.50 (2H, d, J=8.4 Hz), 7.60 (2H, d, J=8.2 Hz), 7.69 (2H, d, J=8.4 Hz).

C) methyl 4-(((4'-chlorobiphenyl-4-yl)(cyclohexyl)methyl)amino)benzoate

Under a nitrogen atmosphere, to a mixture of (4'-chlorobiphenyl-4-yl)(cyclohexyl)methanol obtained in step B, N,N, N',N'-tetramethyl-1,3-propanediamine (0.265 mL) and toluene (4.432 mL) was added methanesulfonyl chloride (0.124 mL) at 0° C., and the reaction mixture was stirred at room temperature for 4 hr. To the reaction mixture were added methyl 4-aminobenzoate (301 mg) and N,N-diisopropylethylamine (0.464 mL) at room temperature, and the mixture was stirred at 100° C. overnight. To the reaction mixture was added water at room temperature, the mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (382.4 mg).

$^1$H NMR (400 MHz, DMSO-d$_6$) δ 0.90-1.26 (4H, m), 1.34 (1H, d, J=11.3 Hz), 1.55-1.81 (4H, m), 1.93-2.07 (1H, m), 2.50 (1H, s), 3.69 (3H, s), 4.23 (1H, t, J=7.7 Hz), 6.61 (2H, d, J=8.7 Hz), 7.03 (1H, d, J=8.2 Hz), 7.42 (2H, d, J=8.0 Hz), 7.48 (2H, d, J=8.4 Hz), 7.59 (4H, t, J=8.6 Hz), 7.67 (2H, d, J=8.4 Hz).

D) (3R)-1-(4-(((4'-chlorobiphenyl-4-yl)(cyclohexyl)methyl)amino)benzoyl)piperidine-3-carboxylic acid By a method similar to that in Example 1, steps H to J, the title compound was obtained.

Example 25

(3R)-1-(4-((4,4,4-trifluoro-1-(5-phenylpyridin-2-yl)butyl)amino)benzoyl)piperidine-3-carboxylic acid A)
5-bromo-N-methoxy-N-methylpyridine-2-carboxamide A mixture of 5-bromopyridine-2-carboxylic acid (3.0 g), N,O-dimethylhydroxylamine hydrochloride (2.9 g), 1-(3-dimethylaminopropyl)-3-ethylcarbodiimide hydrochloride (5.69 g), 1-hydroxybenzotriazole (4.01 g), N,N-diisopropylethylamine (12.97 mL), 4-dimethylaminopyridine (0.181 g) and DMF (37.1 mL) was stirred at room temperature for 5 hr, and water was added. The mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (2.76 g).

$^1$H NMR (400 MHz, DMSO-d$_6$) δ 3.31 (3H, s), 3.65 (3H, s), 7.58 (1H, d, J=8.2 Hz), 8.19 (1H, dd, J=8.3, 2.3 Hz), 8.75 (1H, d, J=2.3 Hz).

B) 5-(4-chlorophenyl)-N-methoxy-N-methylpyridine-2-carboxamide

Under a nitrogen atmosphere, a mixture of 5-bromo-N-methoxy-N-methylpyridine-2-carboxamide (2.76 g), 4-chlorophenylboronic acid (2.113 g), 1,1'-bis(diphenylphosphino)ferrocene-palladium(II)dichloride dichloromethane complex (0.920 g), sodium carbonate (3.58 g), toluene (43.3 mL) and water (13 mL) was stirred at 100° C. overnight. To the reaction mixture was added water at room temperature, the mixture was extracted with ethyl acetate, and the extract was washed with water and saturated brine, and dried over anhydrous magnesium sulfate. The solvent was evaporated under reduced pressure and the residue was fractionated by HPLC (C18, mobile phase: water/acetonitrile (10 mM ammonium hydrogencarbonate-containing system)), the solvent was evaporated under reduced pressure, and the residue was extracted with ethyl acetate. The extract was washed with water and saturated brine, dried over anhydrous magnesium sulfate, and the solvent was evaporated under reduced pressure to give the title compound (1.242 g).

MS (ESI+): [M+H]$^+$ 277.2.

C) 1-(5-(4-chlorophenyl)pyridin-2-yl)-4,4,4-trifluorobutan-1-one

To a mixture of 5-(4-chlorophenyl)-N-methoxy-N-methylpyridine-2-carboxamide (1.24 g) and THF (18 ml) was added iodo(3,3,3-trifluoropropyl)magnesium diethyl ether solution (8.96 mL) at 0° C. Under a nitrogen atmosphere, the reaction mixture was stirred at 40° C. for 5 hr, and saturated aqueous ammonium chloride solution was added at room temperature. The mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (821.7 mg).

MS (ESI+): [M+H]$^+$ 314.2.

D) 1-(5-(4-chlorophenyl)pyridin-2-yl)-4,4,4-trifluoro-N-methoxybutan-1-imine

A mixture of 1-(5-(4-chlorophenyl)pyridin-2-yl)-4,4,4-trifluorobutan-1-one (821.7 mg), O-methylhydroxylamine hydrochloride (656 mg) and pyridine (5.239 mL) was stirred at room temperature overnight, and water was added. The mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (842.7 mg).

MS (ESI+): [M+H]$^+$ 343.2.

E) 4,4,4-trifluoro-1-(5-phenylpyridin-2-yl)butan-1-amine

Under a hydrogen atmosphere, a mixture of 1-(5-(4-chlorophenyl)pyridin-2-yl)-4,4,4-trifluoro-N-methoxybutan-1-imine (169.5 mg), palladium on carbon (263 mg) and methanol (1.648 mL) was stirred at room temperature overnight. The insoluble material was filtered off through celite, the filtrate was washed with 1M aqueous sodium hydroxide solution and saturated brine, and the solvent was evaporated under reduced pressure to give the title compound as a crudely purified product. This compound was used in step F without further purification.

MS (ESI+): [M+H]$^+$ 281.1.

F) ethyl 4-((4,4,4-trifluoro-1-(5-phenylpyridin-2-yl)butyl)amino)benzoate

Under a nitrogen atmosphere, a mixture of 4,4,4-trifluoro-1-(5-phenylpyridin-2-yl)butan-1-amine (125.1 mg) obtained in step E, ethyl 4-bromobenzoate (0.214 mL), tris(dibenzylideneacetone)dipalladium (82 mg), 5-(di-tert-butylphosphino)-1',3',5'-triphenyl-1'H-[1,4']bipyrazole (90 mg), sodium tert-butoxide (129 mg), tert-butanol (2.008 mL) and water (0.223 mL) was stirred at 70° C. overnight. To the reaction mixture was added water at room temperature, and the insoluble material was filtered off through celite. The filtrate was extracted with ethyl acetate, and the extract was washed with water and saturated brine, and dried over anhydrous magnesium sulfate. The solvent was evaporated under reduced pressure and the residue was fractionated by HPLC (C18, mobile phase: water/acetonitrile (10 mM ammonium hydrogencarbonate-containing system)). The solvent was evaporated under reduced pressure, and the residue was extracted with ethyl acetate. The extract was washed with water and saturated brine, dried over anhydrous magnesium sulfate, and the solvent was evaporated under reduced pressure to give the title compound (35.3 mg).
MS (ESI+): [M+H]$^+$ 429.4.

G) (3R)-1-(4-((4,4,4-trifluoro-1-(5-phenylpyridin-2-yl)butyl)amino)benzoyl)piperidine-3-carboxylic acid By a method similar to that in Example 1, steps H to J, the title compound was obtained.
By a method similar to that in Example 25, the compound of the below-mentioned Example 111 was produced.

Example 26

(3R)-1-(4-((2-methyl-1-(2-methyl-4-(5-(trifluoromethyl)pyridin-2-yl)phenyl)propyl)amino)benzoyl)piperidine-3-carboxylic acid A) 1-(4-bromo-2-methylphenyl)-2-methylpropan-1-ol To zinc chloride (0.303 g) and lithium chloride (1.037 g) dried by heating under reduced pressure was added a 1M solution (4.45 ml) of trimethylsilylmethylmagnesium chloride in diethyl ether at room temperature, and the mixture was stirred for 15 min. To the reaction mixture was added a 1M solution (24.25 ml) of isopropylmagnesium bromide in THF at room temperature, and the mixture was stirred for 45 min. The reaction mixture was cooled to 0° C., and a solution of 4-bromo-2-methylbenzaldehyde (4.42 g) in THF (3 mL) was added dropwise. The reaction mixture was stirred at 0° C. for 3 hr, and at room temperature overnight. To the reaction mixture was added saturated aqueous ammonium chloride solution, the mixture was extracted with ethyl acetate, and the extract was washed with saturated brine, and dried over anhydrous magnesium sulfate. The solvent was evaporated under reduced pressure and the residue was purified by silica gel column chromatography (ethyl acetate/hexane) to give the title compound (2.43 g).
$^1$H NMR (400 MHz, DMSO-d$_6$) δ 0.74-0.92 (6H, m), 1.76 (1H, dq, J=13.2, 6.6 Hz), 2.26 (3H, s), 4.43 (1H, t, J=5.0 Hz), 5.05 (1H, d, J=4.3 Hz), 7.25-7.39 (3H, m).

B) methyl 4-((1-(4-bromo-2-methylphenyl)-2-methylpropyl)amino)benzoate

Under a nitrogen atmosphere, to a mixture of 1-(4-bromo-2-methylphenyl)-2-methylpropan-1-ol (1.0 g), N,N,N',N'-tetramethyl-1,3-propanediamine (0.820 mL) and toluene (13.71 mL) was added methanesulfonyl chloride (0.382 mL), and the mixture was stirred at 60° C. for 1.5 hr. To the reaction mixture were added methyl 4-aminobenzoate (0.933 g) and N,N-diisopropylethylamine (1.437 mL) at room temperature, and the mixture was stirred at 100° C. overnight. To the reaction mixture was added water at room temperature, the mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (821.4 mg).
MS (ESI+): [M+H]$^+$ 376.2.

C) (3R)-1-(4-((2-methyl-1-(2-methyl-4-(5-(trifluoromethyl)pyridin-2-yl)phenyl)propyl)amino)benzoyl)piperidine-3-carboxylic acid By a method similar to that in Example 1, steps F to J, the title compound was obtained.
By a method similar to that in Example 26, the compound of the below-mentioned Example 112 was produced.

Example 27

(3R)-1-(4-((1-(4'-chlorobiphenyl-4-yl)-4,4,4-trifluorobutyl)amino)benzoyl)piperidine-3-carboxylic acid A) 1-(4-bromophenyl)-4,4,4-trifluorobutan-1-ol To a mixture of 4,4,4-trifluorobutanoic acid (1.0 g), oxalyl dichloride (0.820 mL) and bromobenzene (3.71 mL) was added DMF (0.008 mL), and the mixture was stirred at room temperature for 2 hr. To the reaction mixture was added aluminum chloride (1.408 g) at 0° C., and the mixture was stirred at room temperature for 3 hr. To the reaction mixture was added water at 0° C., the mixture was extracted with ethyl acetate, and the extract was washed with water and saturated brine, and dried over anhydrous magnesium sulfate. The solvent was evaporated under reduced pressure. To a mixture of the residue, ethanol (15 mL) and THF (5 mL) was added sodium borohydride (0.266 g) at 0° C., and the mixture was stirred at room temperature for 2 hr. To the reaction mixture was added water at 0° C., the mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (1.49 g).
$^1$H NMR (300 MHz, DMSO-d$_6$) δ 1.64-1.88 (2H, m), 2.14-2.37 (2H, m), 4.57-4.66 (1H, m), 5.54 (1H, d, J=4.5 Hz), 7.26-7.36 (2H, m), 7.47-7.58 (2H, m).

B) methyl 4-((1-(4-bromophenyl)-4,4,4-trifluorobutyl)amino)benzoate

By a method similar to that in Example 1, steps C and D, the title compound was obtained.
MS (ESI+), found: 265.0.

C) (3R)-ethyl 1-(4-((1-(4-bromophenyl)-4,4,4-trifluorobutyl)amino)benzoyl)piperidine-3-carboxylate By a method similar to that in Example 1, steps H and I, the title compound was obtained.
MS (ESI+): [M+H]$^+$ 542.2.

D) (3R)-1-(4-((1-(4'-chlorobiphenyl-4-yl)-4,4,4-trifluorobutyl)amino)benzoyl)piperidine-3-carboxylic acid By a method similar to that in Example 8, steps A to B, the title compound was obtained.
By a method similar to that in Example 27, the compounds of the below-mentioned Examples 113 and 114 were produced.

Example 28

(3R)-1-((6-((1-(4'-chlorobiphenyl-4-yl)-4,4,4-trifluorobutyl)amino)pyridin-3-yl)carbonyl)piperidine-3-carboxylic acid A) methyl 6-((1-(4-bromophenyl)-4,4,4-trifluorobutyl)amino)nicotinate Using methyl 6-aminonicotinate and in the same manner as in Example 1, steps C to D, the title compound was obtained from 1-(4-bromophenyl)-4,4,4-trifluorobutan-1-ol obtained in Example 27, step A.
MS (ESI+): [M+H]$^+$ 418.1.

B) (3R)-1-((6-((1-(4'-chlorobiphenyl-4-yl)-4,4,4-trifluorobutyl)amino)pyridin-3-yl)carbonyl)piperidine-3-carboxylic acid By a method similar to that in Example 27, steps C to D, the title compound was obtained.
By a method similar to that in Example 28, the compound of the below-mentioned Example 115 was produced.

Example 116

(3R)-1-(4-((2-methyl-1-(2-methyl-4-(4,5,6,7-tetrahydro-2H-indazol-2-yl)phenyl)propyl)amino)benzoyl)piperidine-3-carboxylic acid A) methyl 4-((1-(4-bromo-2-methylphenyl)-2-methylpropyl)amino)benzoate To a mixture of 1-(4-bromo-2-methylphenyl)-2-methylpropan-1-ol (600 mg), N,N,N',N'-tetramethyl-1,3-propanediamine (0.492 mL) and toluene (0.823 mL) was added methanesulfonyl chloride (0.229 mL), and the mixture was stirred at 60° C. for 2 hr. To the reaction mixture were added methyl 4-aminobenzoate (560 mg) and N,N-diisopropylethylamine (0.862 mL) at room temperature, and the mixture was stirred at 100° C. overnight under a nitrogen atmosphere. To the reaction mixture was added water at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (457.4 mg).
$^1$H NMR (400 MHz, DMSO-d$_6$) δ 0.84 (3H, d, J=6.7 Hz), 1.02 (3H, d, J=6.5 Hz), 1.87-2.05 (1H, m), 2.43 (3H, s), 3.70 (3H, s), 4.32 (1H, dd, J=7.3 Hz), 6.50 (2H, d, J=8.4 Hz), 6.88 (1H, d, J=7.5 Hz), 7.21 (1H, d, J=8.4 Hz), 7.31 (1H, d, J=8.4 Hz), 7.37 (1H, s), 7.59 (2H, d, J=8.7 Hz).

B) methyl 4-((2-methyl-1-(2-methyl-4-(4,5,6,7-tetrahydro-2H-indazol-2-yl)phenyl)propyl)amino)benzoate Under a nitrogen atmosphere, a mixture of methyl 4-((1-(4-bromo-2-methylphenyl)-2-methylpropyl)amino)benzoate
  (racemate) (200 mg), 4,5,6,7-tetrahydroindazole (97 mg), copper(I) iodide (121 mg), trans-N,N'-dimethylcyclohexane-1,2-diamine (0.201 mL), potassium carbonate (220 mg) and toluene (1.3 mL) was stirred at 110° C. overnight. To the reaction mixture was added water at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (137.3 mg).
MS (ESI+): [M+H]$^+$ 418.4.

C) 4-((2-methyl-1-(2-methyl-4-(4,5,6,7-tetrahydro-2H-indazol-2-yl)phenyl)propyl)amino)benzoic acid To a mixture of methyl 4-((2-methyl-1-(2-methyl-4-(4,5,6,7-tetrahydro-2H-indazol-2-yl)phenyl)propyl)amino)benzoate (137.3 mg), THF (0.6 mL) and methanol (0.6 mL) was added 1M aqueous sodium hydroxide solution (0.658 mL), and the mixture was stirred at 50° C. overnight. The solvent was evaporated under reduced pressure, the resulting mixture was neutralized with 1M hydrochloric acid (0.658 mL), and extracted with ethyl acetate. The extract was washed with saturated brine, and dried over anhydrous magnesium sulfate. The solvent was evaporated under reduced pressure to give the title compound as a crudely purified product. This compound was used in step D without further purification.
MS (ESI+): [M+H]$^+$ 404.5.

D) ethyl (3R)-1-(4-((2-methyl-1-(2-methyl-4-(4,5,6,7-tetrahydro-2H-indazol-2-yl)phenyl)propyl)amino)benzoyl)piperidine-3-carboxylate A mixture of 4-((2-methyl-1-(2-methyl-4-(4,5,6,7-tetrahydro-2H-indazol-2-yl)phenyl)propyl)amino)benzoic acid obtained in step C, ethyl (3R)-piperidine-3-carboxylate (0.106 mL), 1-(3-dimethylaminopropyl)-3-ethylcarbodiimide hydrochloride (132 mg), 1-hydroxybenzotriazole (93 mg), N,N-diisopropylethylamine (0.180 mL), 4-dimethylaminopyridine (4.2 mg) and DMF (0.860 mL) was stirred at room temperature overnight. To the reaction mixture was added water, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (152.3 mg).
MS (ESI+): [M+H]$^+$ 543.7.

E) (3R)-1-(4-((2-methyl-1-(2-methyl-4-(4,5,6,7-tetrahydro-2H-indazol-2-yl)phenyl)propyl)amino)benzoyl)piperidine-3-carboxylic acid To a mixture of ethyl (3R)-1-(4-((2-methyl-1-(2-methyl-4-(4,5,6,7-tetrahydro-2H-indazol-2-yl)phenyl)propyl)amino)benzoyl)piperidine-3-carboxylate (152.3 mg), THF (0.56 mL) and ethanol (0.56 mL) was added 1M aqueous sodium hydroxide solution (0.561 mL), and the mixture was stirred at room temperature for 1 hr. The solvent was evaporated under reduced pressure, the reaction mixture was neutralized with 1M hydrochloric acid (0.561 mL), and extracted with ethyl acetate. The extract was washed with saturated brine, and dried over anhydrous magnesium sulfate. The solvent was evaporated under reduced pressure to give the title compound (140.4 mg).
$^1$H NMR (400 MHz, DMSO-d$_6$) δ 0.87 (3H, d, J=6.8 Hz), 1.03 (3H, d, J=6.5 Hz), 1.37 (1H, d, J=11.7 Hz), 1.49-1.82 (6H, m), 1.89-2.10 (2H, m), 2.29-2.72 (8H, m), 2.81-3.06 (2H, m), 3.74-3.90 (1H, m), 3.98-4.16 (1H, m), 4.30 (1H, dd, J=7.5 Hz), 6.38-6.57 (3H, m), 7.07 (2H, d, J=8.4 Hz), 7.34 (1H, d, J=8.3 Hz), 7.46 (1H, d, J=9.0 Hz), 7.53 (1H, s), 8.05 (1H, s), 12.35 (1H, brs).

Example 117

(3R)-1-(4-((2-methyl-1-(2-methyl-4-(4,5,6,7-tetrahydro-2H-indazol-2-yl)phenyl)propyl)amino)benzoyl)piperidine-3-carboxylic acid (3R)-1-(4-((2-methyl-1-(2-methyl-4-(4,5,6,7-tetrahydro-2H-indazol-2-yl)phenyl)propyl)amino)benzoyl)piperidine-3-carboxylic acid Racemate of (3R)-1-(4-((2-methyl-1-(2-methyl-4-(4,5,6,7-tetrahydro-2H-indazol-2-yl)phenyl)propyl)amino)benzoyl)piperidine-3-carboxylic acid obtained in Example 116, step E, was fractionated by SFC (column: CHIRALCEL OJ-H (trade name), 20 mmID×250 mL, manufactured by DAICEL CHEMICAL INDUSTRIES, LTD., mobile phase: carbon dioxide/methanol=740/260) to give the title compound (44 mg) with longer retention time.
>99% ee (tR1(AS-H))

compound with shorter retention time by SFC (column: CHIRALPAK AS-H (trade name), 4.6 mmID×150 mL, manufactured by DAICEL CHEMICAL INDUSTRIES, LTD., mobile phase: carbon dioxide/ethanol=600/400)

$^1$H NMR (400 MHz, DMSO-$d_6$) δ 0.87 (3H, d, J=6.5 Hz), 1.03 (3H, d, J=6.4 Hz), 1.29-1.41 (1H, m), 1.47-1.81 (6H, m), 1.90-2.07 (2H, m), 2.26-2.40 (1H, m), 2.47 (3H, s), 2.52-2.57 (2H, m), 2.58-2.66 (2H, m), 2.76-3.06 (2H, m), 3.73-3.92 (1H, m), 3.98-4.16 (1H, m), 4.30 (1H, dd, J=6.7 Hz), 6.39-6.55 (3H, m), 7.07 (2H, d, J=8.3 Hz), 7.34 (1H, d, J=8.4 Hz), 7.46 (1H, d, J=8.5 Hz), 7.53 (1H, s), 8.05 (1H, s), 12.28 (1H, brs).

The Example compounds produced according to the above-mentioned method or a method analogous thereto are shown in the following Table. MS in the Tables shows measured values.

TABLE 1

| Ex. No. | IUPAC name | structure | MS |
|---|---|---|---|
| 1 | (3R)-1-(4-((4,4,4-trifluoro-1-(2-methyl-4-(5-(trifluoromethyl)-pyridin-2-yl)phenyl)-butyl)amino)benzoyl)-piperidine-3-carboxylic acid | 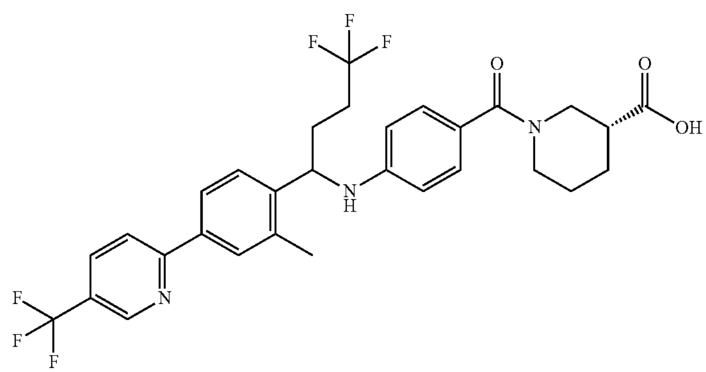 | 594.6 |
| 2 | (3R)-1-(4-((1-(4-(5-chloropyrimidin-2-yl)-2-methylphenyl)-4,4,4-trifluorobutyl)amino)-benzoyl)piperidine-3-carboxylic acid | 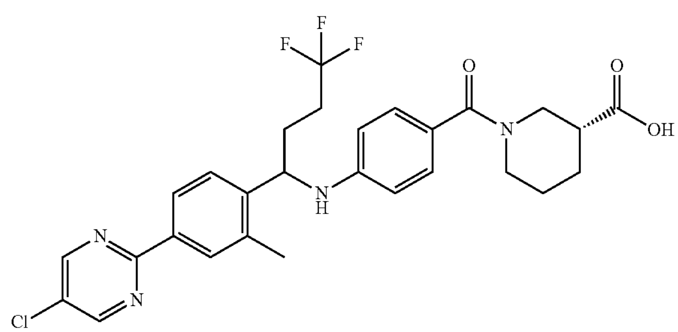 [SMILES: Cc1cc(-c2ncc(Cl)cn2)ccc1C(CCC(F)(F)F)Nc1ccc(C(=O)N2CCC[C@@H](C(=O)O)C2)cc1] | 561.2 |
| 3 | (3R)-1-(4-((4,4,4-trifluoro-1-(2-methyl-4-(5-(trifluoromethyl)-pyrimidin-2-yl)phenyl)-butyl)amino)benzoyl)-piperidine-3-carboxylic acid | 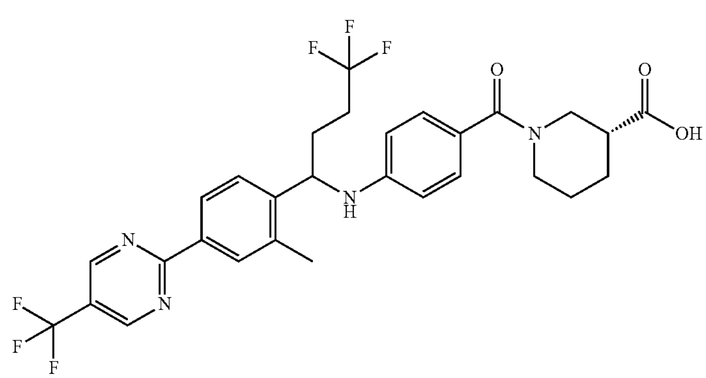 [SMILES: Cc1cc(-c2ncc(C(F)(F)F)cn2)ccc1C(CCC(F)(F)F)Nc1ccc(C(=O)N2CCC[C@@H](C(=O)O)C2)cc1] | 595.2 |

TABLE 1-continued

| Ex. No. | IUPAC name | structure | MS |
|---|---|---|---|
| 4 | (3R)-1-(4-((1-(4-(5-ethylpyrimidin-2-yl)-2-methylphenyl)-4,4,4-trifluorobutyl)amino)benzoyl)piperidine-3-carboxylic acid | 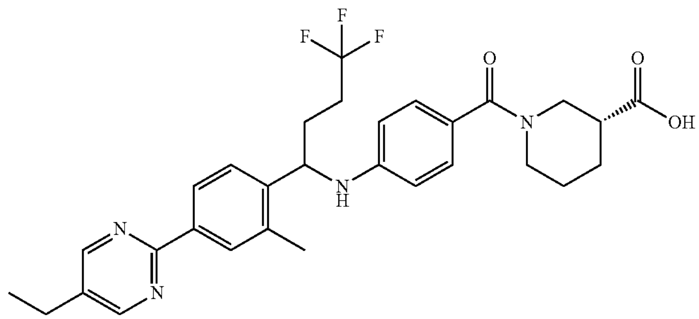 [SMILES: CCc1cnc(-c2ccc(C(CCC(F)(F)F)Nc3ccc(C(=O)N4CCC[C@@H](C(=O)O)C4)cc3)c(C)c2)nc1] | 555.6 |
| 5 | (3R)-1-(4-((4,4,4-trifluoro-1-(4'-fluoro-3-methylbiphenyl-4-yl)butyl)amino)benzoyl)-piperidine-3-carboxylic acid | 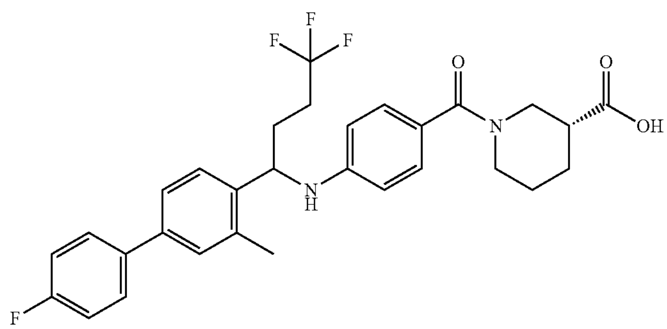 [SMILES: Cc1cc(-c2ccc(F)cc2)ccc1C(CCC(F)(F)F)Nc1ccc(C(=O)N2CCC[C@@H](C(=O)O)C2)cc1] | 543.4 |
| 6 | (3R)-1-((6-((4,4,4-trifluoro-1-(4'-fluoro-3-methylbiphenyl-4-yl)butyl)amino)pyridin-3-yl)carbonyl)-piperidine-3-carboxylic acid | 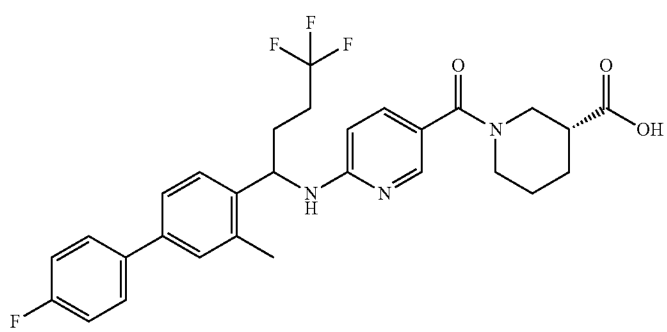 [SMILES: Cc1cc(-c2ccc(F)cc2)ccc1C(CCC(F)(F)F)Nc1ccc(C(=O)N2CCC[C@@H](C(=O)O)C2)cn1] | 544.4 |
| 7 | (3R)-1-(4-((4,4,4-trifluoro-1-(4'-methoxy-3-methylbiphenyl-4-yl)butyl)amino)benzoyl)-piperidine-3-carboxylic acid | 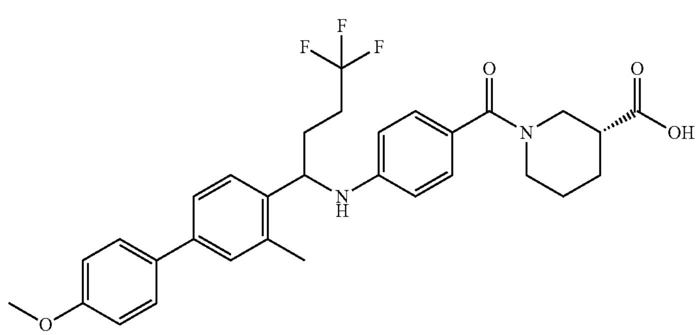 [SMILES: COc1ccc(-c2ccc(C(CCC(F)(F)F)Nc3ccc(C(=O)N4CCC[C@@H](C(=O)O)C4)cc3)c(C)c2)cc1] | 555.4 |

TABLE 1-continued

| Ex. No. | IUPAC name | structure | MS |
|---|---|---|---|
| 8 | (3R)-1-(4-((1-(4'-cyano-3-methylbiphenyl-4-yl)-4,4,4-trifluorobutyl)-amino)benzoyl)-piperidine-3-carboxylic acid | 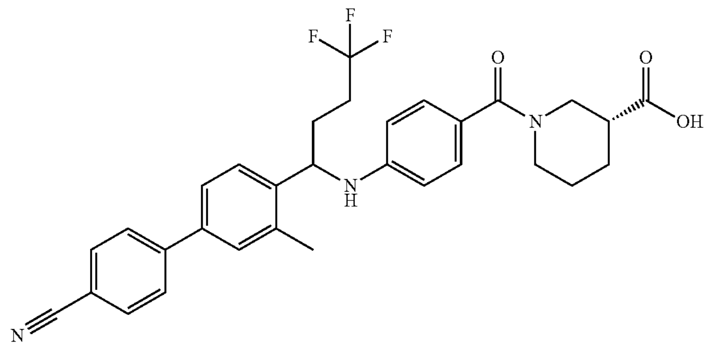 [SMILES: Cc1cc(-c2ccc(C#N)cc2)ccc1C(CCC(F)(F)F)Nc1ccc(C(=O)N2CCC[C@@H](C(=O)O)C2)cc1] | 550.3 |
| 9 | (3R)-1-(4-((4,4,4-trifluoro-1-(2-methyl-4-(6-(trifluoromethyl)-pyridin-3-yl)phenyl)-butyl)amino)benzoyl)-piperidine-3-carboxylic acid | 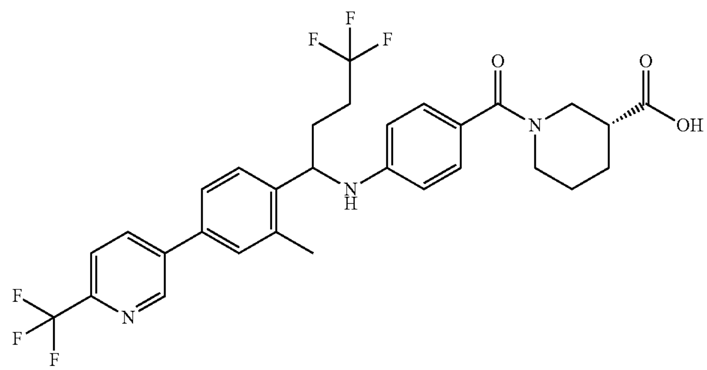 [SMILES: Cc1cc(-c2ccc(C(F)(F)F)nc2)ccc1C(CCC(F)(F)F)Nc1ccc(C(=O)N2CCC[C@@H](C(=O)O)C2)cc1] | 594.3 |
| 10 | (3R)-1-(4-((4,4,4-trifluoro-1-(2-methyl-4-(5-(trifluoromethyl)-pyridin-2-yl)phenyl)-butyl)amino)benzoyl)-piperidine-3-carboxylic acid | 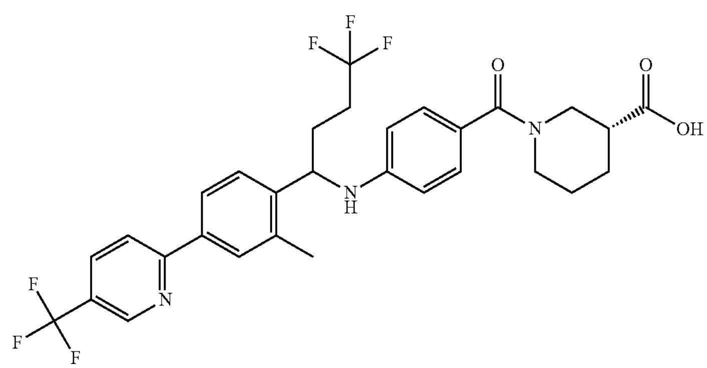 [SMILES: Cc1cc(-c2ccc(C(F)(F)F)cn2)ccc1C(CCC(F)(F)F)Nc1ccc(C(=O)N2CCC[C@@H](C(=O)O)C2)cc1] | 594.3 |

TABLE 2

| 11 | (3R)-1-(4-((4,4,4-trifluoro-1-(2-methyl-4-(5-(trifluoromethyl)-pyrimidin-2-yl)phenyl)-butyl)amino)benzoyl)-piperidine-3-carboxylic acid | | 595.3 |

TABLE 2-continued

| | | | |
|---|---|---|---|
| 12 | (3R)-1-(4-((1-(4-(5-chloropyrimidin-2-yl)-2-methylphenyl)-4,4,4-trifluorobutyl)amino)-benzoyl)piperidine-3-carboxylic acid | 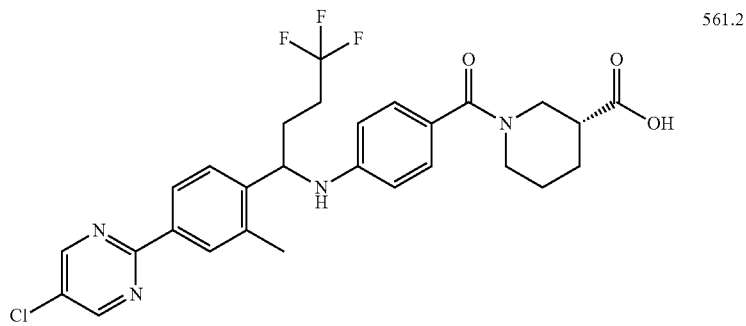 | 561.2 |
| 13 | (3R)-1-(4-((1-(4-(5-ethylpyrimidin-2-yl)-2-methylphenyl)-4,4,4-trifluorobutyl)amino)-benzoyl)piperidine-3-carboxylic acid | 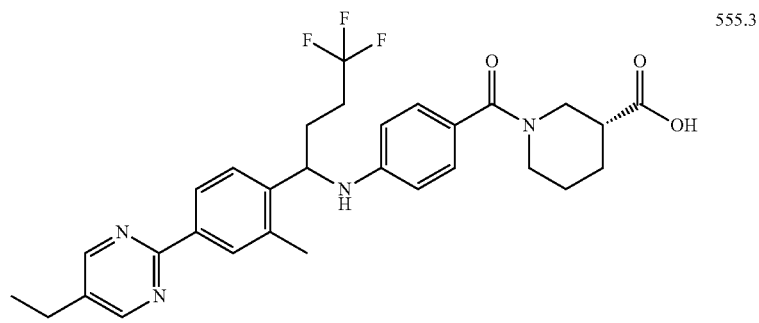 | 555.3 |
| 14 | (3R)-1-(4-((4,4,4-trifluoro-1-(2-methyl-4-(6-(trifluoromethyl)-pyridin-3-yl)phenyl)-butyl)amino)benzoyl)-piperidine-3-carboxylic acid | 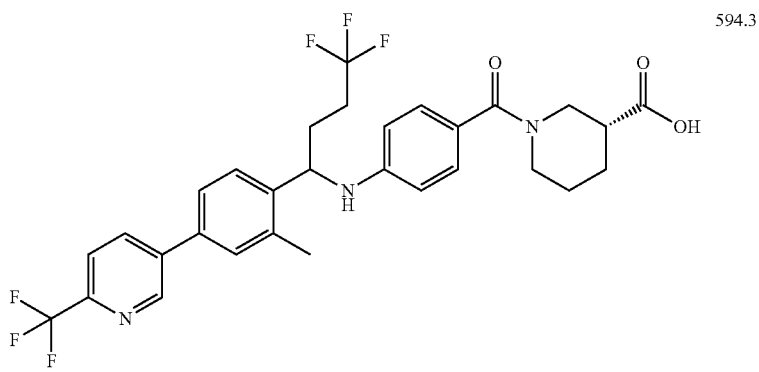 | 594.3 |
| 15 | (3R)-1-((6-((1-(4'-chloro-3-methylbiphenyl-4-yl)-4,4,4-trifluorobutyl)-amino)pyridin-3-yl)carbonyl)piperidine-3-carboxylic acid | 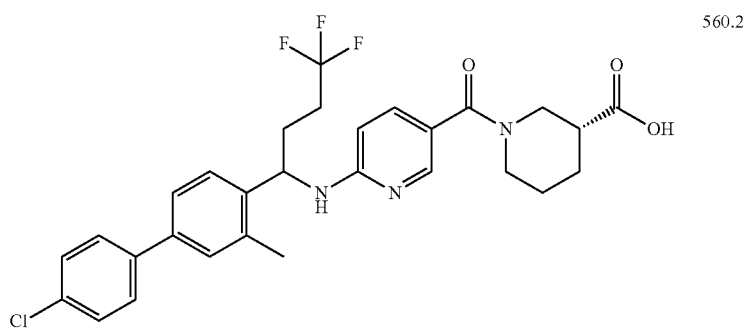 | 560.2 |
| 16 | (3R)-1-(4-(((4'-chloro-3-methylbiphenyl-4-yl)(cyclohexyl)methyl)-amino)benzoyl)-piperidine-3-carboxylic acid | 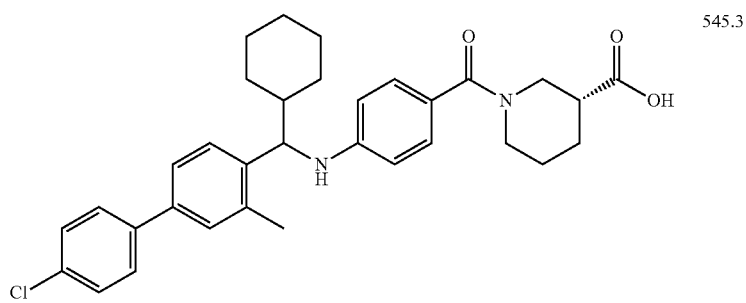 | 545.3 |

TABLE 2-continued

| | | | |
|---|---|---|---|
| 17 | (3R)-1-((6-(((4'-chloro-3-methylbiphenyl-4-yl)(cyclohexyl)methyl)-amino)pyridin-3-yl)carbonyl)piperidine-3-carboxylic acid | 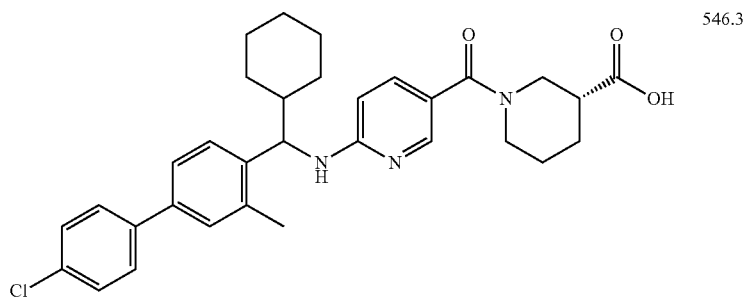 | 546.3 |
| 18 | (3R)-1-(4-((1-(4'-chloro-2,6-(dimethylbiphenyl-4-yl)-4,4,4-trifluorobutyl)-amino)benzoyl)-piperidine-3-carboxylic acid | 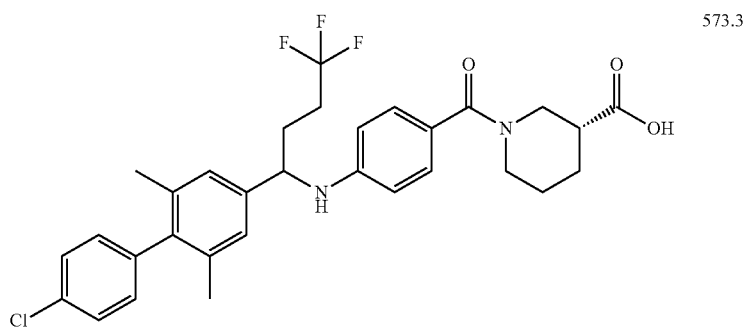 | 573.3 |
| 19 | (3R)-1-(4-((4,4,4-trifluoro-1-(4-(3-isopropyl-1H-pyrazol-1-yl)-2-methylphenyl)-butyl)amino)benzoyl)-piperidine-3-carboxylic acid | 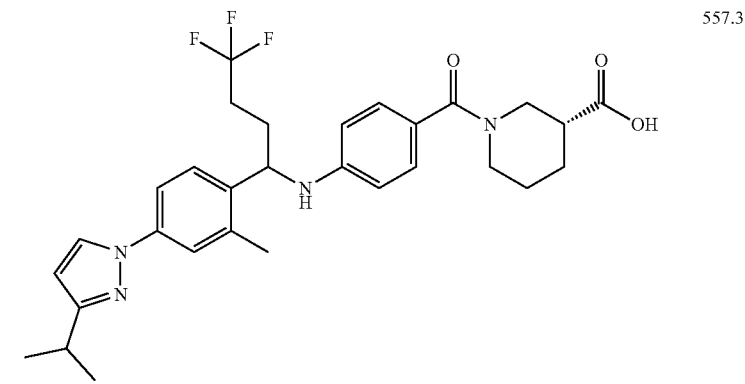 | 557.3 |
| 20 | (3R)-1-(4-((4,4,4-trifluoro-1-(2-methyl-4-(4,5,6,7-tetrahydro-2H-indazol-2-yl)phenyl)butyl)amino)-benzoyl)piperidine-3-carboxylic acid | 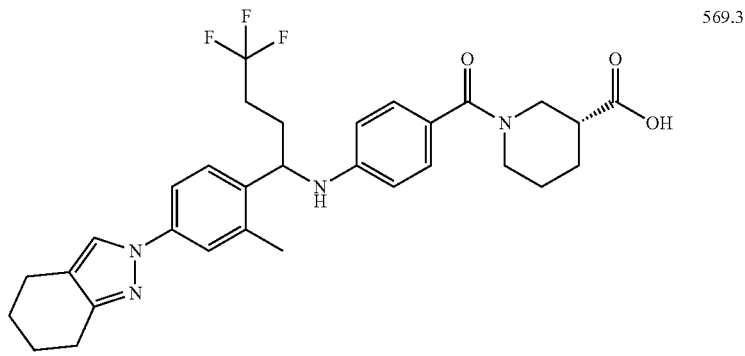 | 569.3 |

TABLE 3

| | | | |
|---|---|---|---|
| 21 | (3R)-1-(4-((4,4,4-trifluoro-1-(2-methyl-4-(4,5,6,7-tetrahydro-2H-indazol-2-yl)-phenyl)butyl)amino)-benzoyl)piperidine-3-carboxylic acid | 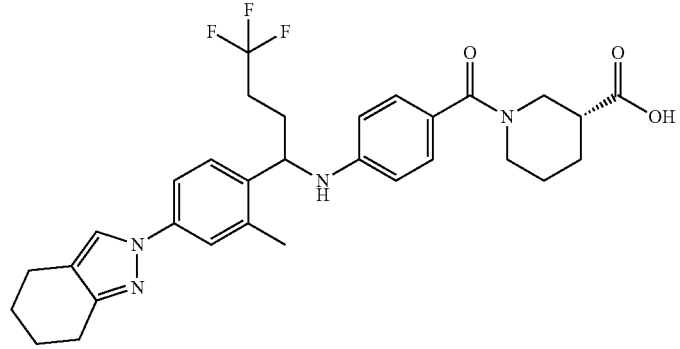 [SMILES: Cc1cc(-n2cc3c(n2)CCCC3)ccc1C(CCC(F)(F)F)Nc1ccc(C(=O)N2CCC[C@@H](C(=O)O)C2)cc1] | 569.6 |
| 22 | (3R)-1-(4-((4,4,4-trifluoro-1-(4-(3-isopropyl-1H-pyrazol-1-yl)-2-methylphenyl)-butyl)amino)benzoyl)-piperidine-3-carboxylic acid | 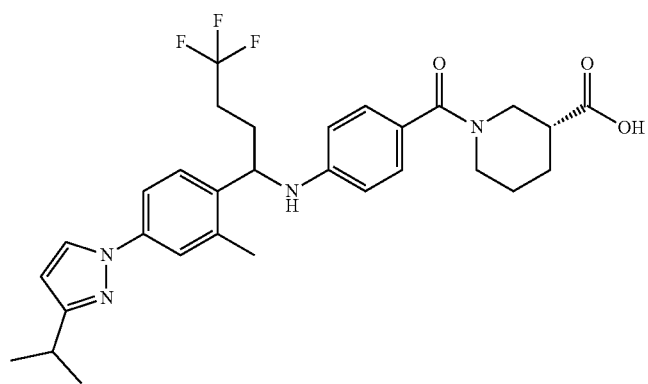 [SMILES: Cc1cc(-n2ccc(C(C)C)n2)ccc1C(CCC(F)(F)F)Nc1ccc(C(=O)N2CCC[C@@H](C(=O)O)C2)cc1] | 557.4 |
| 23 | (3R)-1-(4-((1-(4-(5-tert-butyl-1,3-oxazol-2-yl)-2-methylphenyl)-4,4,4-trifluorobutyl)-amino)benzoyl)-piperidine-3-carboxylic acid | 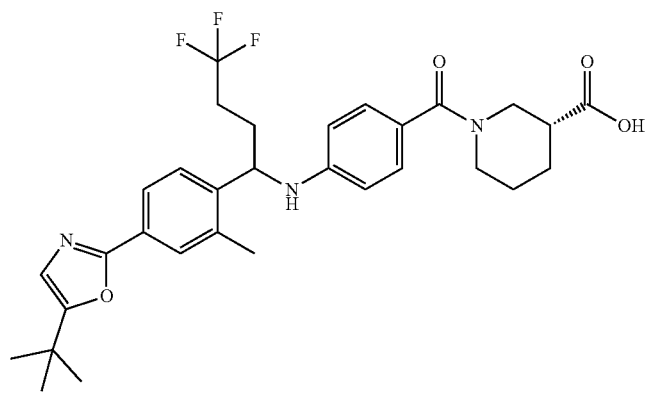 [SMILES: Cc1cc(-c2ncc(C(C)(C)C)o2)ccc1C(CCC(F)(F)F)Nc1ccc(C(=O)N2CCC[C@@H](C(=O)O)C2)cc1] | 572.3 |
| 24 | (3R)-1-(4-(((4'-chlorobiphenyl-4-yl)(cyclohexyl)methyl)-amino)benzoyl)-piperidine-3-carboxylic acid | 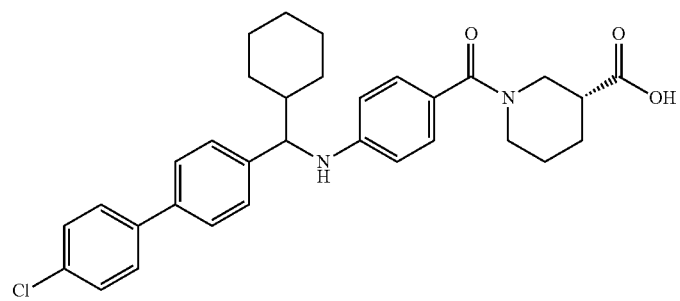 [SMILES: O=C(O)[C@@H]1CCCN(C(=O)c2ccc(NC(c3ccc(-c4ccc(Cl)cc4)cc3)C3CCCCC3)cc2)C1] | 531.6 |

TABLE 3-continued

| | | | |
|---|---|---|---|
| 25 | (3R)-1-(4-((4,4,4-trifluoro-1-(5-phenylpyridin-2-yl)-butyl)amino)benzoyl)-piperidine-3-carboxylic acid | 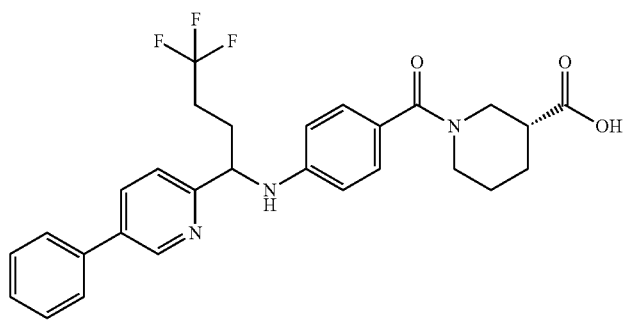 [SMILES: O=C(O)[C@@H]1CCCN(C(=O)c2ccc(NC(CCC(F)(F)F)c3ccc(-c4ccccc4)cn3)cc2)C1] | 512.5 |
| 26 | (3R)-1-(4-((2-methyl-1-(2-methyl-4-(5-(trifluoromethyl)-pyridin-2-yl)phenyl)-propyl)amino)benzoyl)-piperidine-3-carboxylic acid | 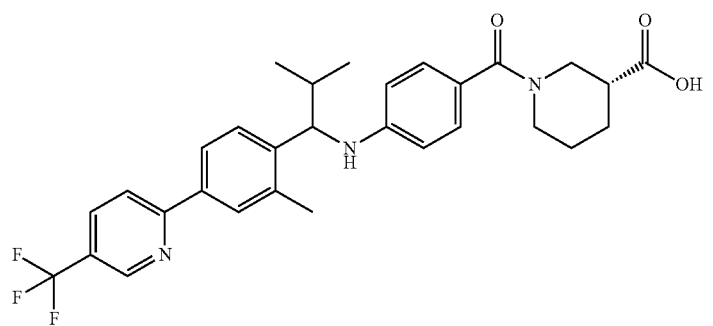 [SMILES: Cc1cc(-c2ccc(C(F)(F)F)cn2)ccc1C(Nc1ccc(C(=O)N2CCC[C@@H](C(=O)O)C2)cc1)C(C)C] | 540.6 |
| 27 | (3R)-1-(4-((1-(4'-chlorobiphenyl-4-yl)-4,4,4-trifluorobutyl)-amino)benzoyl)-piperidine-3-carboxylic acid | 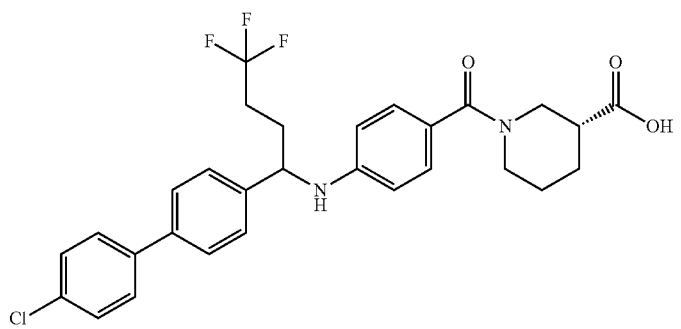 [SMILES: O=C(O)[C@@H]1CCCN(C(=O)c2ccc(NC(CCC(F)(F)F)c3ccc(-c4ccc(Cl)cc4)cc3)cc2)C1] | 545.2 |
| 28 | (3R)-1-((6-((1-(4'-chlorobiphenyl-4-yl)-4,4,4-trifluorobutyl)-amino)pyridin-3-yl)carbonyl)piperidine-3-carboxylic acid | 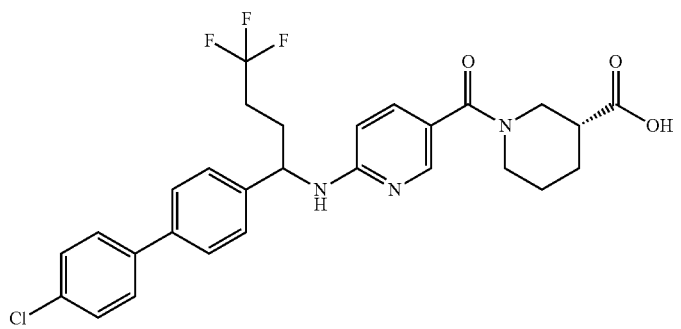 [SMILES: O=C(O)[C@@H]1CCCN(C(=O)c2ccc(NC(CCC(F)(F)F)c3ccc(-c4ccc(Cl)cc4)cc3)nc2)C1] | 546.2 |

TABLE 3-continued

| 29 | (3R)-1-(4-((4,4,4-trifluoro-1-(3-methyl-4'-(trifluoromethyl)-biphenyl-4-yl)butyl)-amino)benzoyl)-piperidine-3-carboxylic acid | 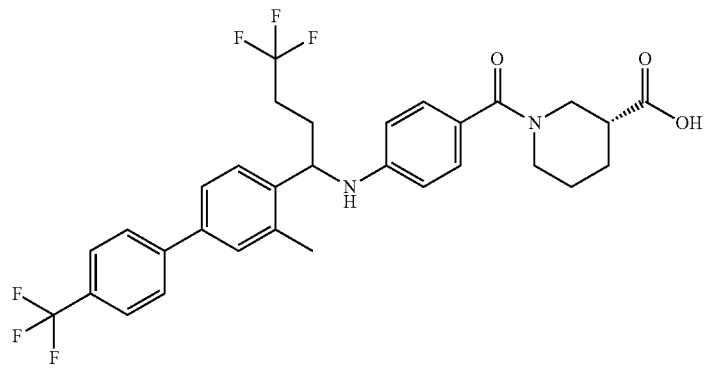 [SMILES: Cc1cc(-c2ccc(C(F)(F)F)cc2)ccc1C(CCC(F)(F)F)Nc1ccc(C(=O)N2CCC[C@@H](C(=O)O)C2)cc1] | 593.4 |

| 30 | (3R)-1-(4-((4,4,4-trifluoro-1-(3-methyl-4'-(trifluoromethoxy)-biphenyl-4-yl)butyl)-amino)benzoyl)-piperidine-3-carboxylic acid | 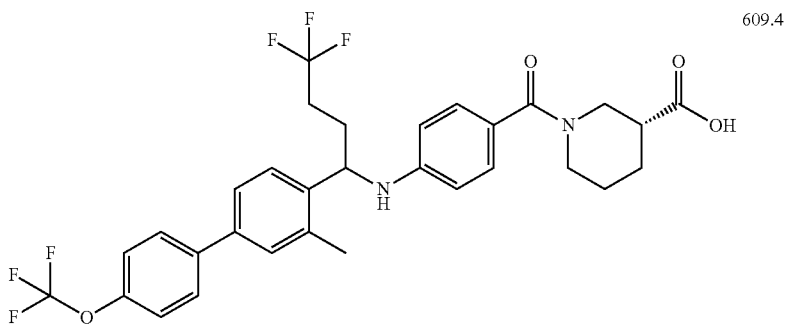 | 609.4 |

TABLE 4

| 31 | (3R)-1-(4-((1-(4'-carbamoyl-3-methylbiphenyl-4-yl)-4,4,4-trifluorobutyl)-amino)benzoyl)-piperidine-3-carboxylic acid | 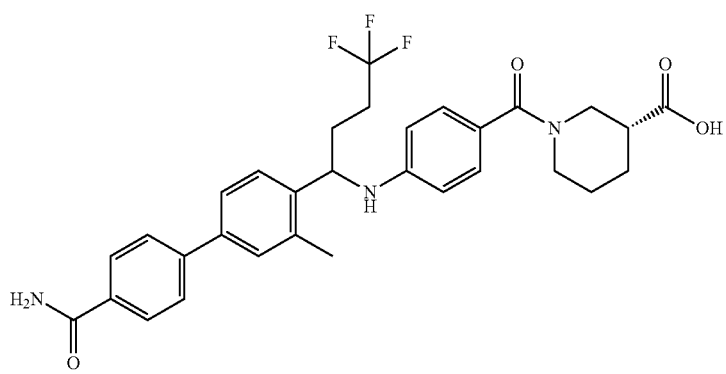 [SMILES: Cc1cc(-c2ccc(C(N)=O)cc2)ccc1C(CCC(F)(F)F)Nc1ccc(C(=O)N2CCC[C@@H](C(=O)O)C2)cc1] | 568.3 |

| 32 | (3R)-1-(4-((1-(2',4'-dichloro-3-methylbiphenyl-4-yl)-4,4,4-trifluorobutyl)-amino)benzoyl)-piperidine-3-carboxylic acid | 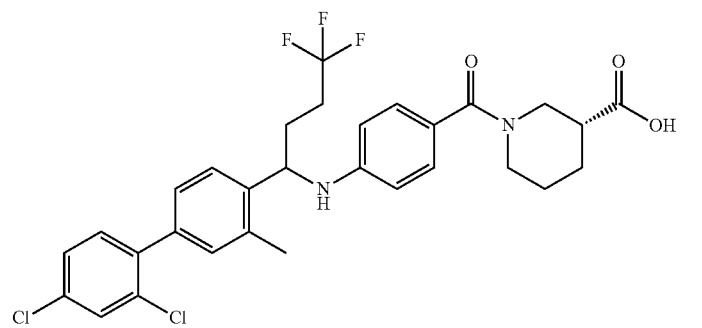 [SMILES: Cc1cc(-c2ccc(Cl)cc2Cl)ccc1C(CCC(F)(F)F)Nc1ccc(C(=O)N2CCC[C@@H](C(=O)O)C2)cc1] | 593.2 |

TABLE 4-continued

| | | | |
|---|---|---|---|
| 33 | (3R)-1-(4-((1-(2',3-dimethylbiphenyl-4-yl)-4,4,4-trifluorobutyl)-amino)benzoyl)-piperidine-3-carboxylic acid | 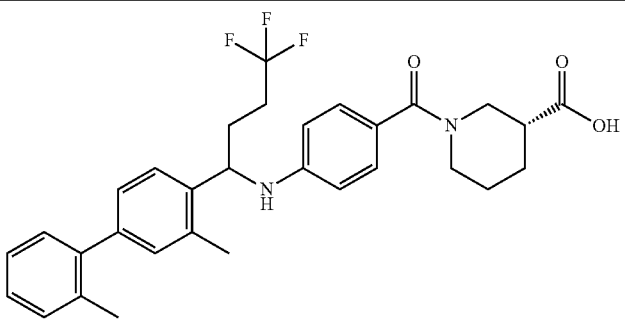 | 539.3 |
| 34 | (3R)-1-(4-((1-(2'-chloro-3-methylbiphenyl-4-yl)-4,4,4-trifluorobutyl)-amino)benzoyl)-piperidine-3-carboxylic acid | 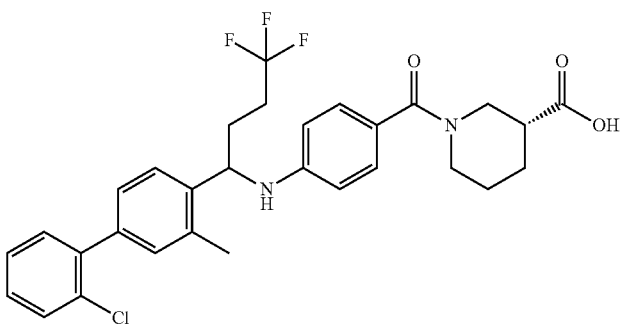 [SMILES: Cc1cc(-c2ccccc2Cl)ccc1C(CCC(F)(F)F)Nc1ccc(C(=O)N2CCC[C@@H](C(=O)O)C2)cc1] | 559.3 |
| 35 | (3R)-1-(4-((1-(2',5'-dichloro-3-methylbiphenyl-4-yl)-4,4,4-trifluorobutyl)-amino)benzoyl)-piperidine-3-carboxylic acid | 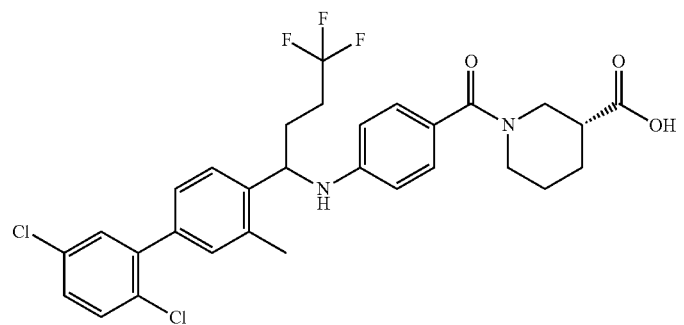 [SMILES: Cc1cc(-c2cc(Cl)ccc2Cl)ccc1C(CCC(F)(F)F)Nc1ccc(C(=O)N2CCC[C@@H](C(=O)O)C2)cc1] | 593.2 |
| 36 | (3R)-1-(4-((4,4,4-trifluoro-1-(3-methyl-3'-((methylsulfonyl)-amino)biphenyl-4-yl)-butyl)amino)benzoyl)-piperidine-3-carboxylic acid | 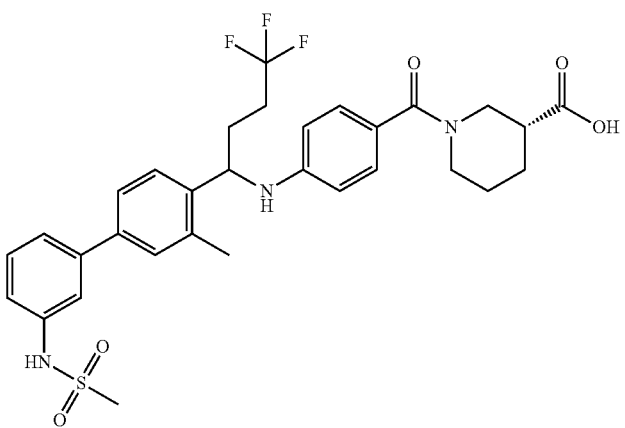 [SMILES: Cc1cc(-c2cccc(NS(C)(=O)=O)c2)ccc1C(CCC(F)(F)F)Nc1ccc(C(=O)N2CCC[C@@H](C(=O)O)C2)cc1] | 618.3 |

TABLE 4-continued

| 37 | (3R)-1-(4-((1-(5'-chloro-2'-isopropoxy-3-methylbiphenyl-4-yl)-4,4,4-trifluorobutyl)-amino)benzoyl)-piperidine-3-carboxylic acid | 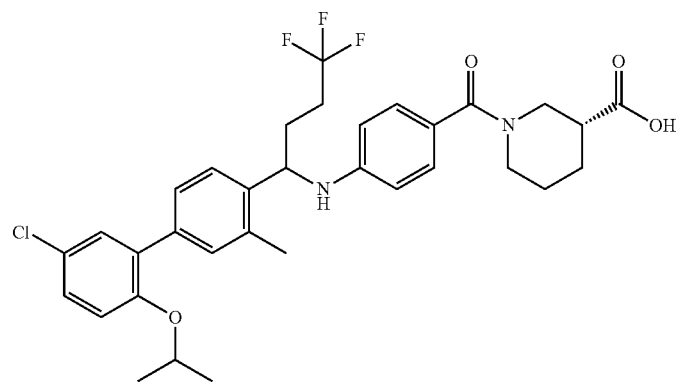 [SMILES: Cc1cc(-c2cc(Cl)ccc2OC(C)C)ccc1C(CCC(F)(F)F)Nc1ccc(C(=O)N2CCC[C@@H](C(=O)O)C2)cc1] | 617.3 |
| 38 | (3R)-1-(4-((1-(3'-cyano-3-methylbiphenyl-4-yl)-4,4,4-trifluorobutyl)amino)-benzoyl)piperidine-3-carboxylic acid | 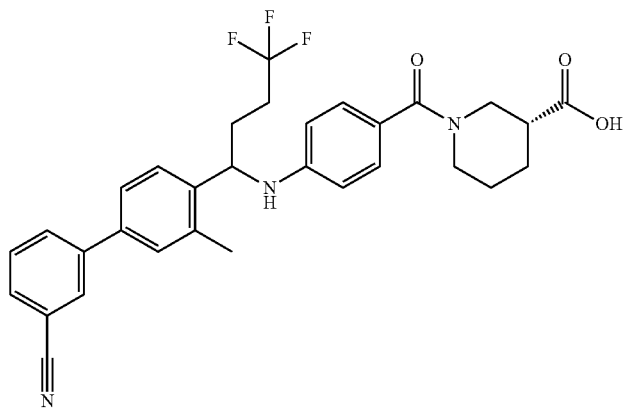 [SMILES: Cc1cc(-c2cccc(C#N)c2)ccc1C(CCC(F)(F)F)Nc1ccc(C(=O)N2CCC[C@@H](C(=O)O)C2)cc1] | 550.3 |
| 39 | (3R)-1-(4-((4,4,4-trifluoro-1-(3-methyl-2'-((methylsulfonyl)-amino)biphenyl-4-yl)butyl)amino)-benzoyl)piperidine-3-carboxylic acid | 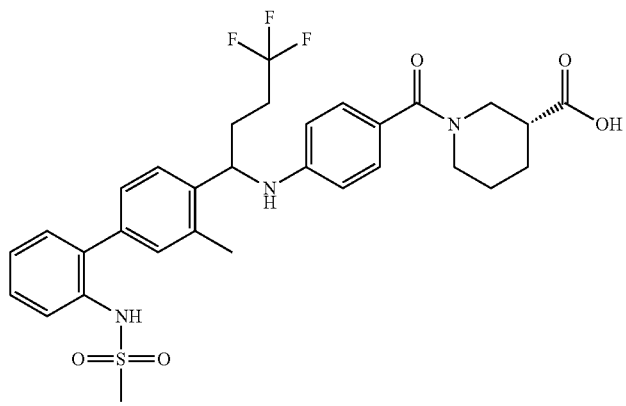 [SMILES: Cc1cc(-c2ccccc2NS(C)(=O)=O)ccc1C(CCC(F)(F)F)Nc1ccc(C(=O)N2CCC[C@@H](C(=O)O)C2)cc1] | 618.3 |
| 40 | (3R)-1-(4-((4,4,4-trifluoro-1-(2-methyl-4-(pyridin-3-yl)-phenyl)butyl)amino)-benzoyl)piperidine-3-carboxylic acid | 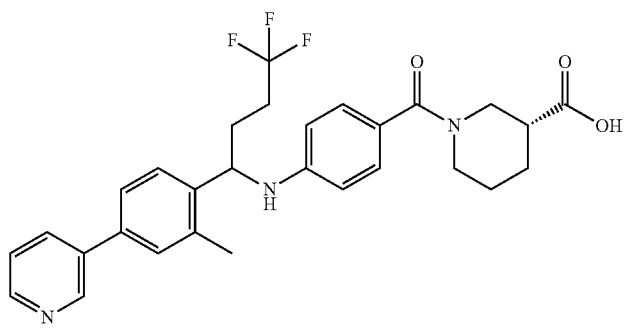 [SMILES: Cc1cc(-c2cccnc2)ccc1C(CCC(F)(F)F)Nc1ccc(C(=O)N2CCC[C@@H](C(=O)O)C2)cc1] | 527.3 |

TABLE 5

| 41 | (3R)-1-(4-((4,4,4-trifluoro-1-(2-methyl-4-(pyridin-4-yl)-phenyl)butyl)amino)-benzoyl)piperidine-3-carboxylic acid | 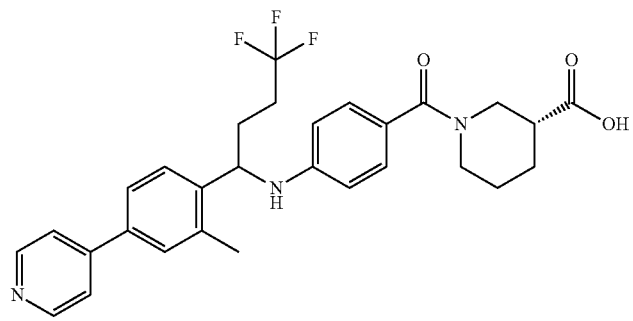 [SMILES: Cc1cc(-c2ccncc2)ccc1C(CCC(F)(F)F)Nc1ccc(C(=O)N2CCC[C@@H](C(=O)O)C2)cc1] | 526.3 |
| 42 | (3R)-1-(4-((4,4,4-trifluoro-1-(4-(2-methoxypyridin-3-yl)-2-methylphenyl)butyl)-amino)benzoyl)-piperidine-3-carboxylic acid | 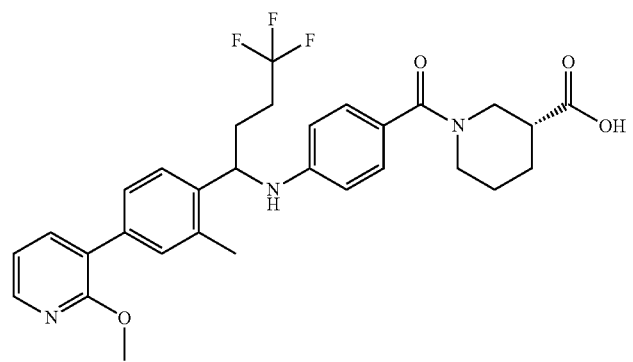 [SMILES: COc1ncccc1-c1ccc(C(CCC(F)(F)F)Nc2ccc(C(=O)N3CCC[C@@H](C(=O)O)C3)cc2)c(C)c1] | 556.3 |
| 43 | (3R)-1-(4-((1-(3'-chloro-3-methylbiphenyl-4-yl)-4,4,4-trifluorobutyl)-amino)benzoyl)-piperidine-3-carboxylic acid | 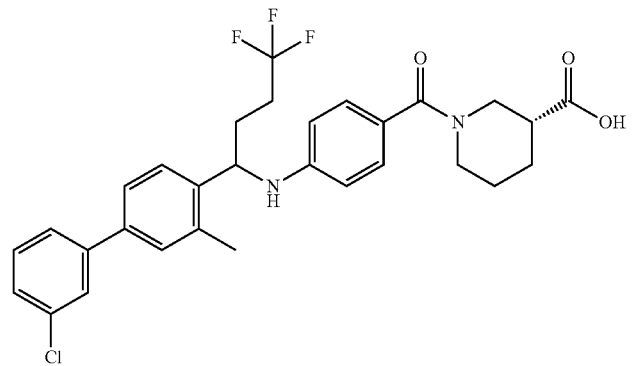 [SMILES: Cc1cc(-c2cccc(Cl)c2)ccc1C(CCC(F)(F)F)Nc1ccc(C(=O)N2CCC[C@@H](C(=O)O)C2)cc1] | 559.3 |
| 44 | (3R)-1-(4-((1-(4'-chloro-3-methylbiphenyl-4-yl)-4,4,4-trifluorobutyl)-amino)benzoyl)-piperidine-3-carboxylic acid | 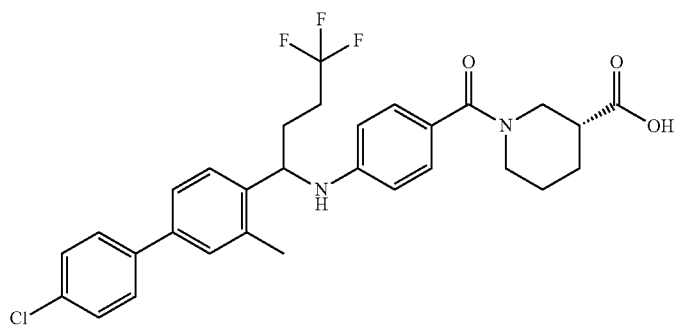 [SMILES: Cc1cc(-c2ccc(Cl)cc2)ccc1C(CCC(F)(F)F)Nc1ccc(C(=O)N2CCC[C@@H](C(=O)O)C2)cc1] | 559.2 |

TABLE 5-continued

| 45 | (3R)-1-(4-((1-(4'-chloro-2',3-dimethylbiphenyl-4-yl)-4,4,4-trifluorobutyl)-amino)benzoyl)-piperidine-3-carboxylic acid | 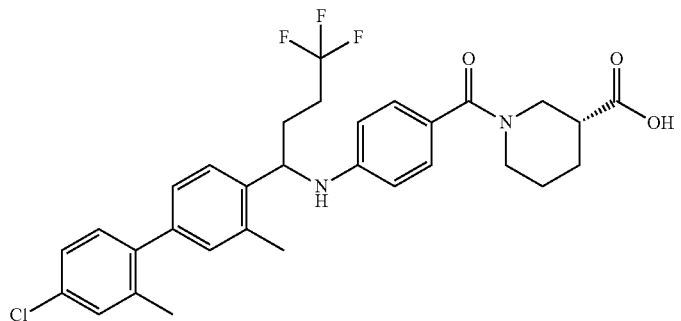 [SMILES: Cc1cc(Cl)ccc1-c1ccc(C(CCC(F)(F)F)Nc2ccc(C(=O)N3CCC[C@@H](C(=O)O)C3)cc2)c(C)c1] | 573.3 |
| 46 | (3R)-1-(4-((4,4,4-trifluoro-1-(3,3',5'-trimethylbiphenyl-4-yl)butyl)amino)-benzoyl)piperidine-3-carboxylic acid | 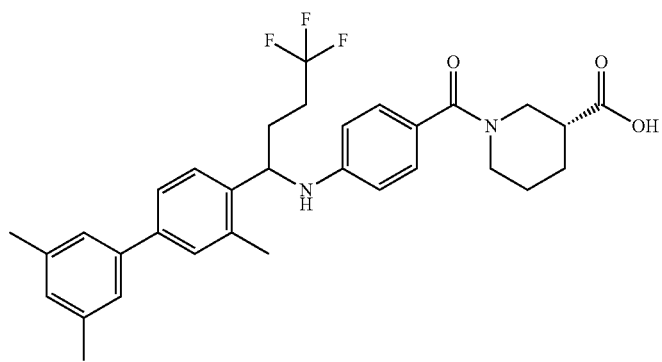 [SMILES: Cc1cc(C)cc(-c2ccc(C(CCC(F)(F)F)Nc3ccc(C(=O)N4CCC[C@@H](C(=O)O)C4)cc3)c(C)c2)c1] | 553.3 |
| 47 | (3R)-1-(4-((1-(2'-chloro-3-methyl-5'-(trifluoromethyl)-biphenyl-4-yl)-4,4,4-trifluorobutyl)amino)-benzoyl)piperidine-3-carboxylic acid | 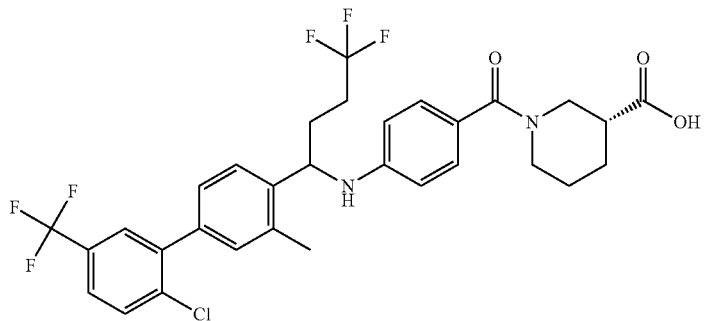 [SMILES: Cc1cc(-c2cc(C(F)(F)F)ccc2Cl)ccc1C(CCC(F)(F)F)Nc1ccc(C(=O)N2CCC[C@@H](C(=O)O)C2)cc1] | 627.3 |
| 48 | (3R)-1-(4-((4,4,4-trifluoro-1-(2'-isopropoxy-3-methylbiphenyl-4-yl)butyl)amino)-benzoyl)piperidine-3-carboxylic acid | 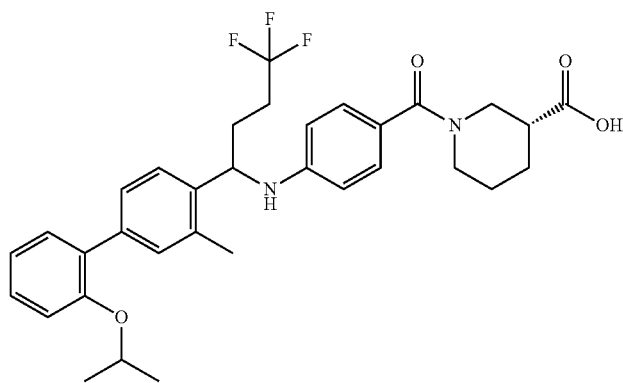 [SMILES: Cc1cc(-c2ccccc2OC(C)C)ccc1C(CCC(F)(F)F)Nc1ccc(C(=O)N2CCC[C@@H](C(=O)O)C2)cc1] | 583.3 |

TABLE 5-continued

| | | | |
|---|---|---|---|
| 49 | (3R)-1-(4-((1-(3'-acetamido-3-methylbiphenyl-4-yl)-4,4,4-trifluorobutyl)-amino)benzoyl)-piperidine-3-carboxylic acid | 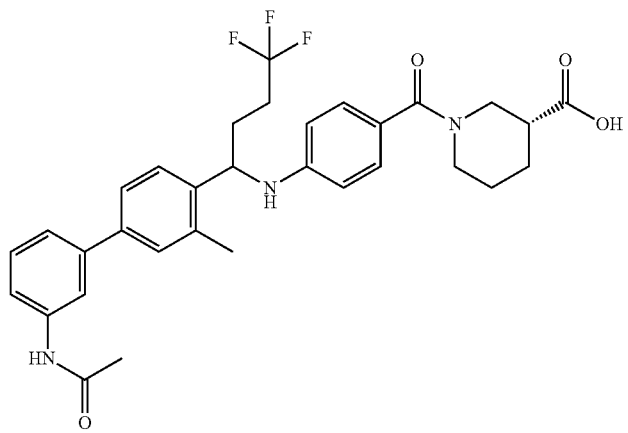 [SMILES: CC(=O)Nc1cccc(-c2ccc(C(CCC(F)(F)F)Nc3ccc(C(=O)N4CCC[C@@H](C(=O)O)C4)cc3)c(C)c2)c1] | 582.3 |
| 50 | (3R)-1-(4-((1-(2'-acetamido-3-methylbiphenyl-4-yl)-4,4,4-trifluorobutyl)-amino)benzoyl)-piperidine-3-carboxylic acid | 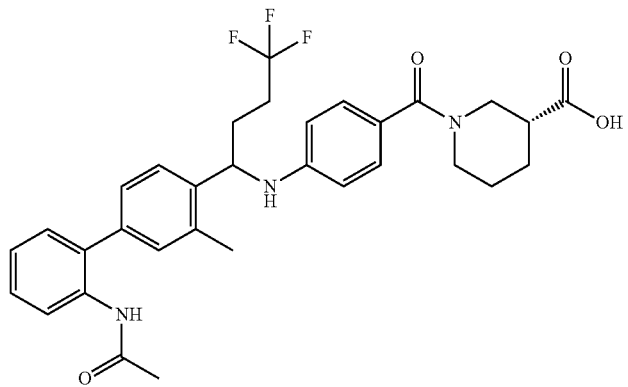 [SMILES: CC(=O)Nc1ccccc1-c1ccc(C(CCC(F)(F)F)Nc2ccc(C(=O)N3CCC[C@@H](C(=O)O)C3)cc2)c(C)c1] | 582.3 |

TABLE 6

| | | | |
|---|---|---|---|
| 51 | (3R)-1-(4-((1-(3'-((2-cyanoethyl)carbamoyl)-3-methylbiphenyl-4-yl)-4,4,4-trifluorobutyl)-amino)benzoyl)-piperidine-3-carboxylic acid | 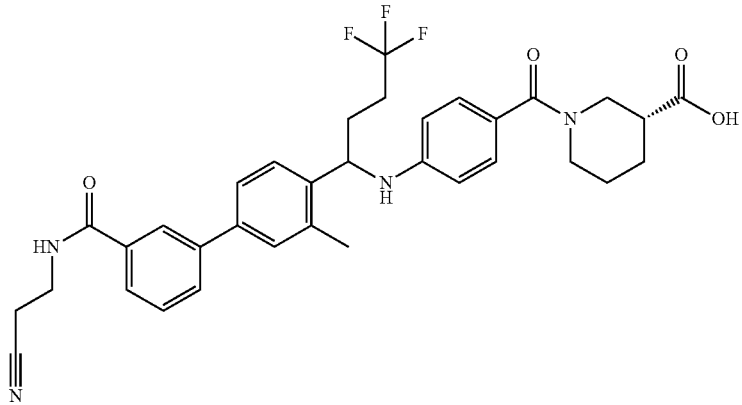 [SMILES: Cc1cc(-c2cccc(C(=O)NCCC#N)c2)ccc1C(CCC(F)(F)F)Nc1ccc(C(=O)N2CCC[C@@H](C(=O)O)C2)cc1] | 621.3 |
| 52 | (3R)-1-(4-((4,4,4-trifluoro-1-(3-methyl-3'-(((methylsulfonyl)-amino)methyl)biphenyl-4-yl)butyl)amino)-benzoyl)piperidine-3-carboxylic acid | 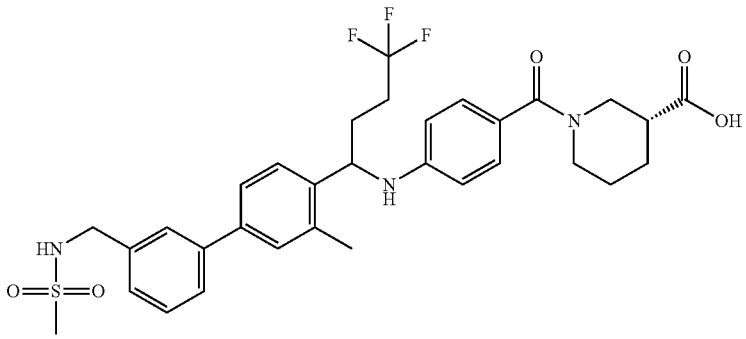 [SMILES: Cc1cc(-c2cccc(CNS(C)(=O)=O)c2)ccc1C(CCC(F)(F)F)Nc1ccc(C(=O)N2CCC[C@@H](C(=O)O)C2)cc1] | 632.3 |

TABLE 6-continued

| 53 | (3R)-1-(4-((4,4,4-trifluoro-1-(2-methyl-4-(pyrimidin-5-yl)phenyl)butyl)amino)-benzoyl)piperidine-3-carboxylic acid | 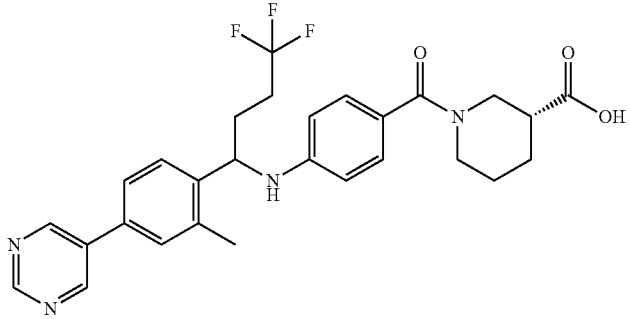 [SMILES: Cc1cc(-c2cncnc2)ccc1C(CCC(F)(F)F)Nc1ccc(C(=O)N2CCC[C@@H](C(=O)O)C2)cc1] | 527.3 |
| 54 | (3R)-1-(4-((1-(4-(3,5-dimethyl-1,2-oxazol-4-yl)-2-methylphenyl)-4,4,4-trifluorobutyl)-amino)benzoyl)-piperidine-3-carboxylic acid | 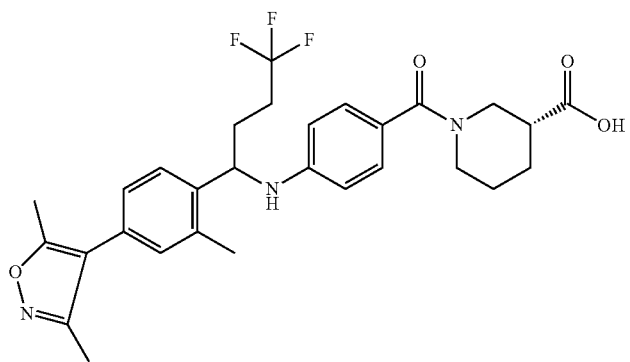 [SMILES: Cc1cc(-c2c(C)noc2C)ccc1C(CCC(F)(F)F)Nc1ccc(C(=O)N2CCC[C@@H](C(=O)O)C2)cc1] | 544.3 |
| 55 | (3R)-1-(4-((1-(3',4'-dichloro-3-methylbiphenyl-4-yl)-4,4,4-trifluorobutyl)-amino)benzoyl)-piperidine-3-carboxylic acid | 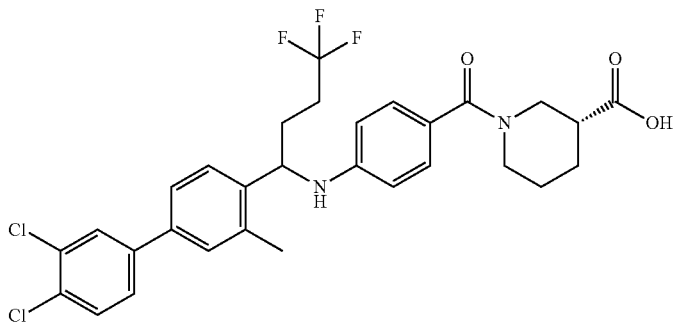 [SMILES: Cc1cc(-c2ccc(Cl)c(Cl)c2)ccc1C(CCC(F)(F)F)Nc1ccc(C(=O)N2CCC[C@@H](C(=O)O)C2)cc1] | 593.2 |
| 56 | (3R)-1-(4-((1-(3'-(cyanomethyl)-3-methylbiphenyl-4-yl)-4,4,4-trifluorobutyl)-amino)benzoyl)-piperidine-3-carboxylic acid | 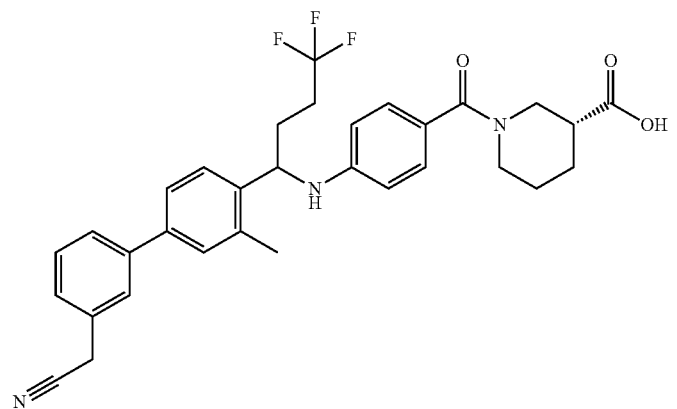 [SMILES: Cc1cc(-c2cccc(CC#N)c2)ccc1C(CCC(F)(F)F)Nc1ccc(C(=O)N2CCC[C@@H](C(=O)O)C2)cc1] | 564.3 |

TABLE 6-continued

| | | | |
|---|---|---|---|
| 57 | (3R)-1-(4-((4,4,4-trifluoro-1-(3'-isobutoxy-3-methylbiphenyl-4-yl)-butyl)amino)benzoyl)-piperidine-3-carboxylic acid | 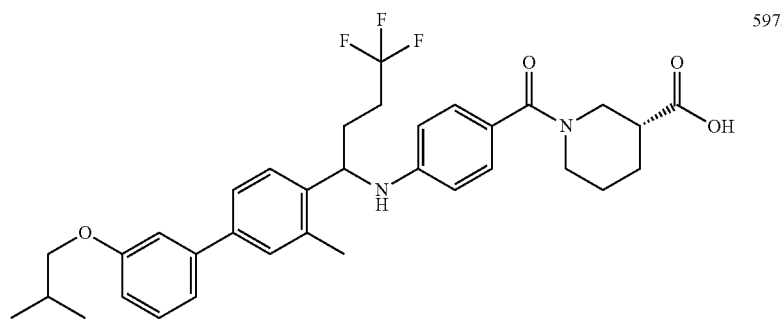 | 597.4 |
| 58 | (3R)-1-(4-((1-(4'-acetamido-3-methylbiphenyl-4-yl)-4,4,4-trifluorobutyl)-amino)benzoyl)-piperidine-3-carboxylic acid | 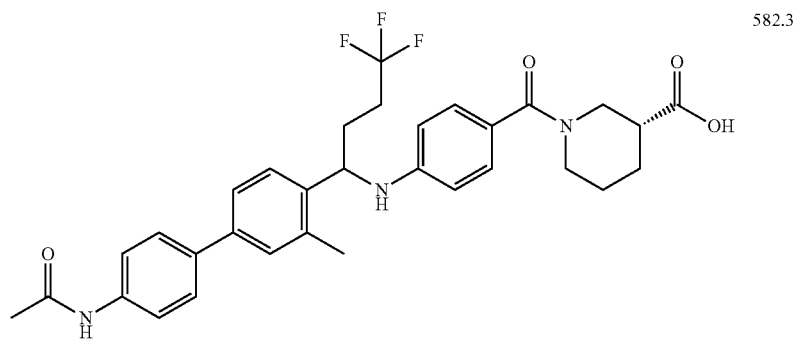 | 582.3 |
| 59 | (3R)-1-(4-((4,4,4-trifluoro-1-(3-methyl-4'-(methylsulfonyl)-biphenyl-4-yl)butyl)-amino)benzoyl)-piperidine-3-carboxylic acid | 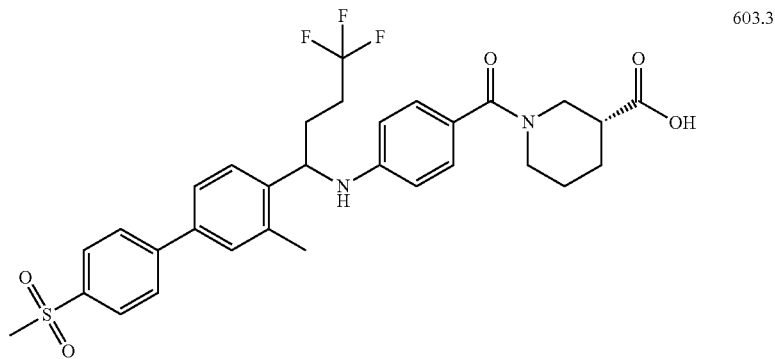 | 603.3 |
| 60 | (3R)-1-(4-((4,4,4-trifluoro-1-(3-methyl-4'-((methylsulfonyl)-amino)biphenyl-4-yl)-butyl)amino)benzoyl)-piperidine-3-carboxylic acid | 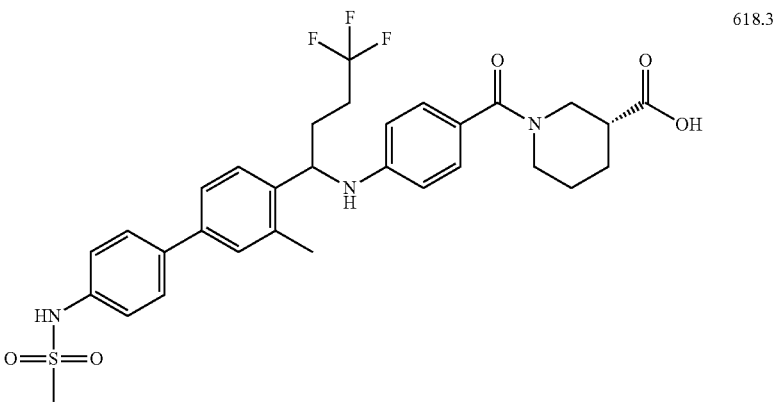 | 618.3 |

TABLE 7

| 61 | (3R)-1-(4-((4,4,4-trifluoro-1-(4-(2-fluoropyridin-3-yl)-2-methylphenyl)butyl)amino)-benzoyl)piperidine-3-carboxylic acid | 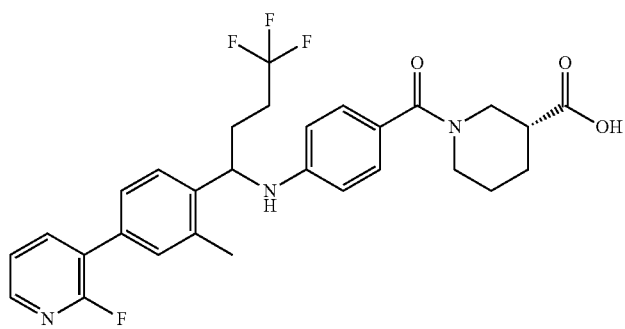 [SMILES: Cc1cc(-c2cccnc2F)ccc1C(CCC(F)(F)F)Nc1ccc(C(=O)N2CCC[C@@H](C(=O)O)C2)cc1] | 544.3 |
| 62 | (3R)-1-(4-((4,4,4-trifluoro-1-(2-methyl-4-(6-methylpyridin-3-yl)phenyl)butyl)amino)-benzoyl)piperidine-3-carboxylic acid | 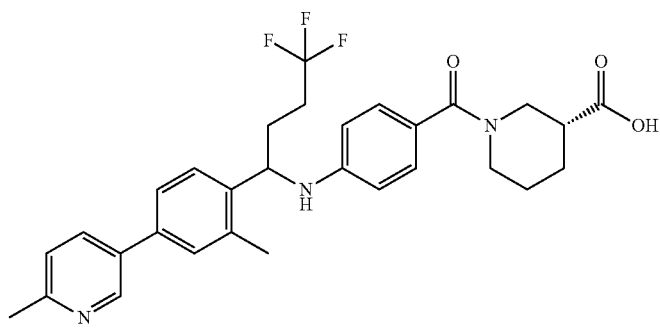 [SMILES: Cc1ccc(-c2ccc(C(CCC(F)(F)F)Nc3ccc(C(=O)N4CCC[C@@H](C(=O)O)C4)cc3)c(C)c2)cn1] | 540.3 |
| 63 | (3R)-1-(4-((4,4,4-trifluoro-1-(2-methyl-4-(1-methyl-1H-pyrazol-4-yl)phenyl)butyl)-amino)benzoyl)-piperidine-3-carboxylic acid | 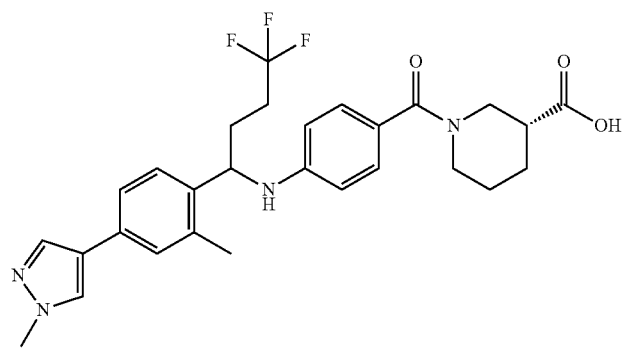 [SMILES: Cc1cc(-c2cnn(C)c2)ccc1C(CCC(F)(F)F)Nc1ccc(C(=O)N2CCC[C@@H](C(=O)O)C2)cc1] | 529.3 |
| 64 | (3R)-1-(4-((4,4,4-trifluoro-1-(4-(2-fluoro-6-methylpyridin-3-yl)-2-methylphenyl)-butyl)amino)benzoyl)-piperidine-3-carboxylic acid | 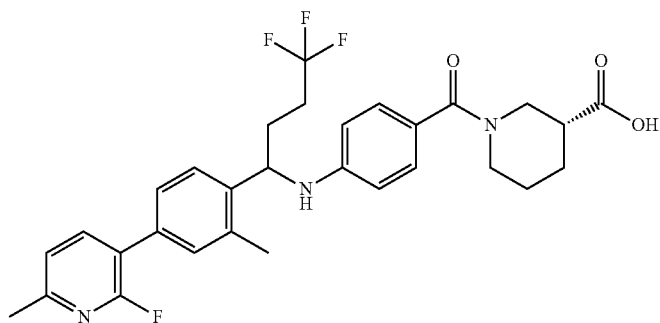 [SMILES: Cc1ccc(-c2ccc(C(CCC(F)(F)F)Nc3ccc(C(=O)N4CCC[C@@H](C(=O)O)C4)cc3)c(C)c2)c(F)n1] | 558.3 |

TABLE 7-continued

| 65 | (3R)-1-(4-((1-(2'-cyano-3-methylbiphenyl-4-yl)-4,4,4-trifluorobutyl)amino)benzoyl)piperidine-3-carboxylic acid | 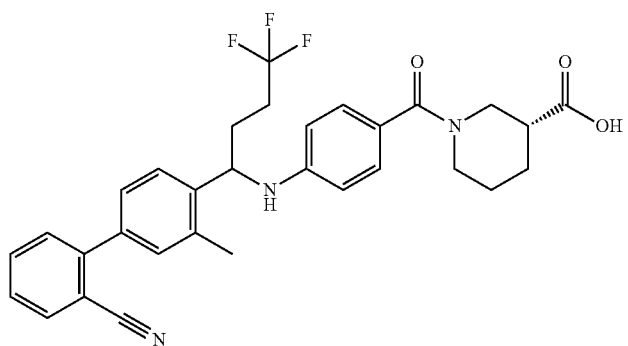 [SMILES: Cc1cc(-c2ccccc2C#N)ccc1C(CCC(F)(F)F)Nc1ccc(C(=O)N2CCC[C@@H](C(=O)O)C2)cc1] | 550.3 |
| 66 | (3R)-1-(4-((1-(4'-(tert-butylsulfamoyl)-3-methylbiphenyl-4-yl)-4,4,4-trifluorobutyl)amino)benzoyl)-piperidine-3-carboxylic acid | 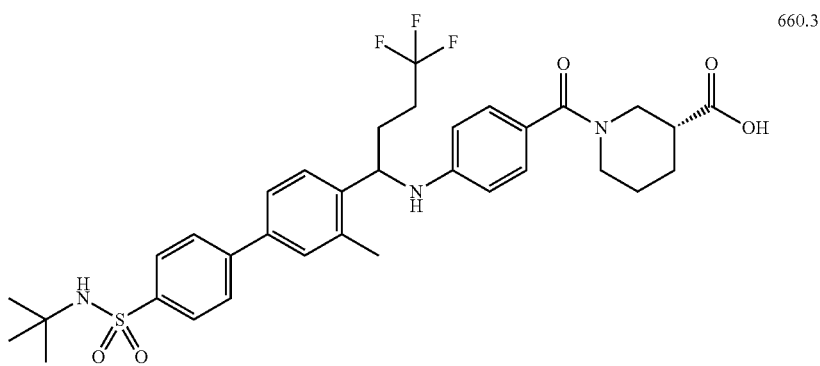 | 660.3 |
| 67 | (3R)-1-(4-((4,4,4-trifluoro-1-(2-methyl-4-(1-methyl-1H-pyrrol-2-yl)phenyl)butyl)amino)benzoyl)-piperidine-3-carboxylic acid | 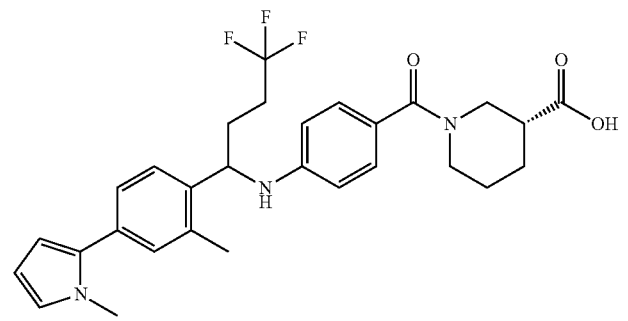 [SMILES: Cc1cc(-c2cccn2C)ccc1C(CCC(F)(F)F)Nc1ccc(C(=O)N2CCC[C@@H](C(=O)O)C2)cc1] | 528.3 |
| 68 | (3R)-1-(4-((1-(4-(6-ethoxypyridin-3-yl)-2-methylphenyl)-4,4,4-trifluorobutyl)amino)benzoyl)piperidine-3-carboxylic acid | 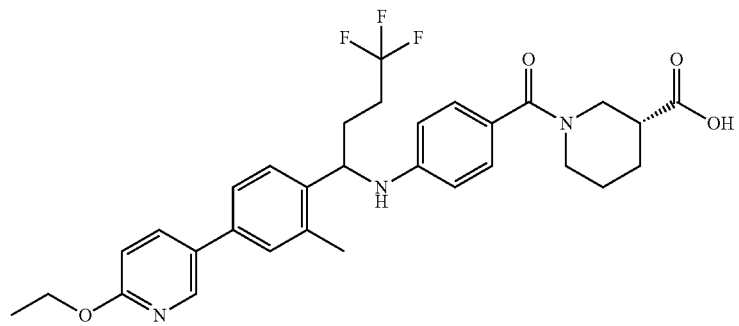 [SMILES: CCOc1ccc(-c2ccc(C(CCC(F)(F)F)Nc3ccc(C(=O)N4CCC[C@@H](C(=O)O)C4)cc3)c(C)c2)cn1] | 570.3 |

TABLE 7-continued

| | | | |
|---|---|---|---|
| 69 | (3R)-1-(4-((4,4,4-trifluoro-1-(2-methyl-4-(6-(morpholin-4-yl)pyridin-3-yl)-phenyl)butyl)amino)-benzoyl)piperidine-3-carboxylic acid | 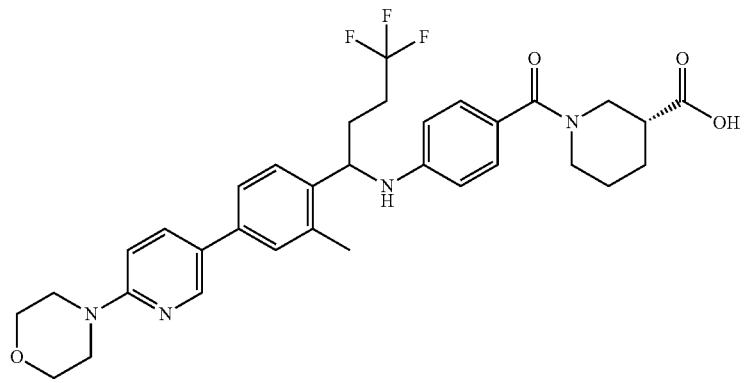 [SMILES: Cc1cc(-c2ccc(N3CCOCC3)nc2)ccc1C(CCC(F)(F)F)Nc1ccc(C(=O)N2CCC[C@@H](C(=O)O)C2)cc1] | 611.3 |
| 70 | (3R)-1-(4-((4,4,4-trifluoro-1-(2-methyl-4-(1-methyl-1H-pyrazol-5-yl)phenyl)butyl)-amino)benzoyl)-piperidine-3-carboxylic acid | 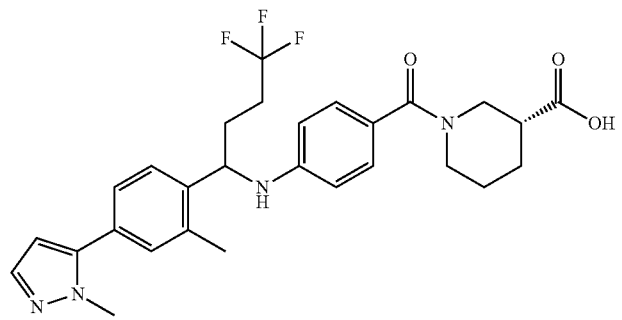 [SMILES: Cc1cc(-c2ccnn2C)ccc1C(CCC(F)(F)F)Nc1ccc(C(=O)N2CCC[C@@H](C(=O)O)C2)cc1] | 529.3 |

TABLE 8

| | | | |
|---|---|---|---|
| 71 | (3R)-1-(4-((4,4,4-trifluoro-1-(2-methyl-4-(6-(pyrrolidin-1-yl)pyridin-3-yl)-phenyl)butyl)amino)-benzoyl)piperidine-3-carboxylic acid | 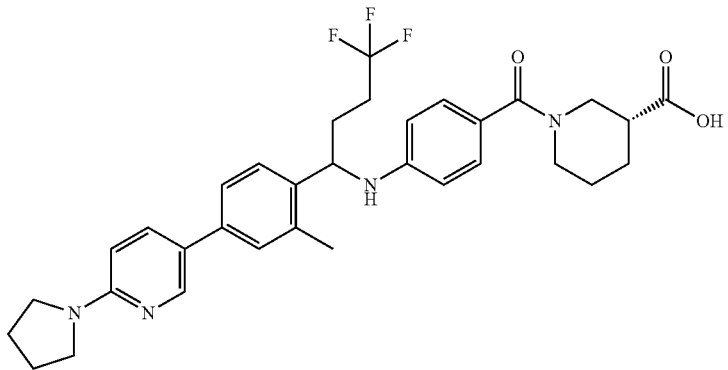 [SMILES: Cc1cc(-c2ccc(N3CCCC3)nc2)ccc1C(CCC(F)(F)F)Nc1ccc(C(=O)N2CCC[C@@H](C(=O)O)C2)cc1] | 595.4 |
| 72 | (3R)-1-(4-((4,4,4-trifluoro-1-(2-methyl-4-(4-methyl-3,4-dihydro-2H-pyrido[3,2-b][1,4]oxazin-7-yl)phenyl)butyl)amino)-benzoyl)piperidine-3-carboxylic acid | 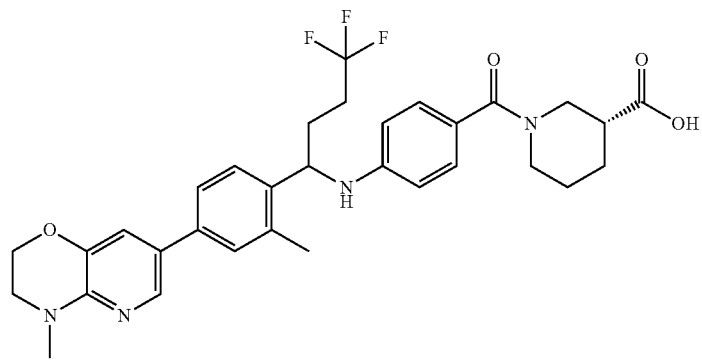 [SMILES: Cc1cc(-c2cnc3c(c2)OCCN3C)ccc1C(CCC(F)(F)F)Nc1ccc(C(=O)N2CCC[C@@H](C(=O)O)C2)cc1] | 597.3 |

TABLE 8-continued

| 73 | (3R)-1-(4-((4,4,4-trifluoro-1-(2-methyl-4-(6-(tetrahydro-2H-pyran-4-yloxy)pyridin-3-yl)phenyl)butyl)amino)benzoyl)-piperidine-3-carboxylic acid | 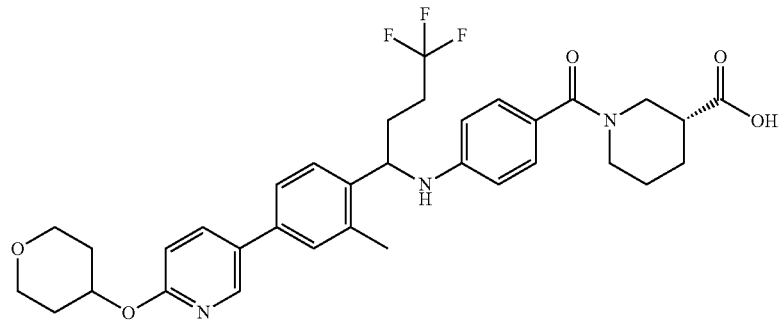 [SMILES: Cc1cc(-c2ccc(OC3CCOCC3)nc2)ccc1C(CCC(F)(F)F)Nc1ccc(C(=O)N2CCC[C@@H](C(=O)O)C2)cc1] | 626.3 |
| 74 | (3R)-1-(4-((1-(4-(6-chloropyridin-3-yl)-2-methylphenyl)-4,4,4-trifluorobutyl)amino)-benzoyl)piperidine-3-carboxylic acid | 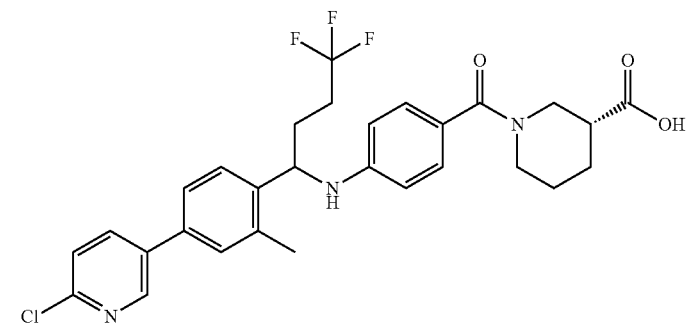 | 560.2 |
| 75 | (3R)-1-(4-((4,4,4-trifluoro-1-(4-(6-isopropoxypyridin-3-yl)-2-methylphenyl)-butyl)amino)benzoyl)-piperidine-3-carboxylic acid | 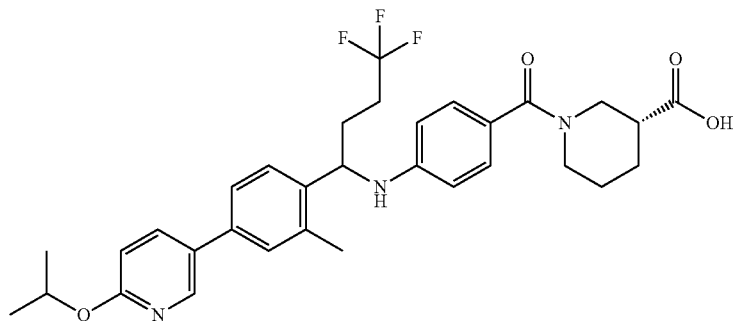 [SMILES: Cc1cc(-c2ccc(OC(C)C)nc2)ccc1C(CCC(F)(F)F)Nc1ccc(C(=O)N2CCC[C@@H](C(=O)O)C2)cc1] | 584.3 |
| 76 | (3R)-1-(4-((4,4,4-trifluoro-1-(2-methyl-4-(6-(2,2,2-trifluoroethoxy)-pyridin-3-yl)phenyl)-butyl)amino)benzoyl)-piperidine-3-carboxylic acid | 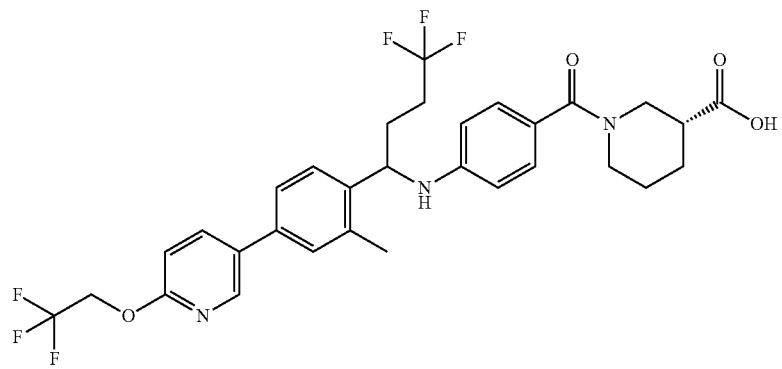 [SMILES: Cc1cc(-c2ccc(OCC(F)(F)F)nc2)ccc1C(CCC(F)(F)F)Nc1ccc(C(=O)N2CCC[C@@H](C(=O)O)C2)cc1] | 624.3 |

TABLE 8-continued

| 77 | (3R)-1-(4-((1-(4-(6-cyclopropylpyridin-3-yl)-2-methylphenyl)-4,4,4-trifluorobutyl)amino)benzoyl)-piperidine-3-carboxylic acid | 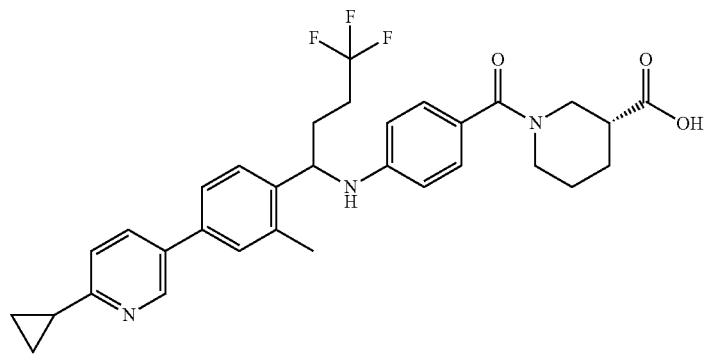 [SMILES: Cc1cc(-c2ccc(C3CC3)nc2)ccc1C(CCC(F)(F)F)Nc1ccc(C(=O)N2CCC[C@@H](C(=O)O)C2)cc1] | 566.3 |
| 78 | (3R)-1-(4-((1-(4'-tert-butyl-3-methylbiphenyl-4-yl)-4,4,4-trifluorobutyl)amino)-benzoyl)piperidine-3-carboxylic acid | 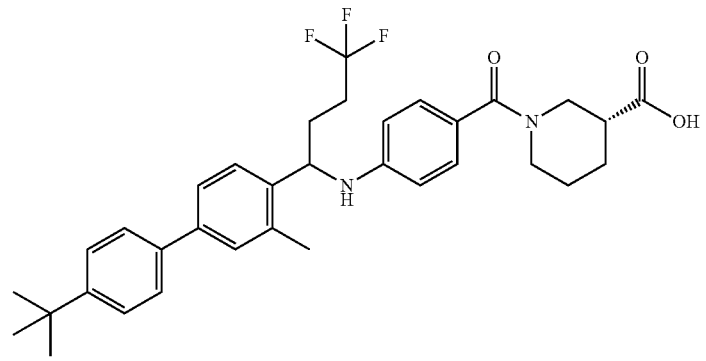 [SMILES: Cc1cc(-c2ccc(C(C)(C)C)cc2)ccc1C(CCC(F)(F)F)Nc1ccc(C(=O)N2CCC[C@@H](C(=O)O)C2)cc1] | 581.4 |
| 79 | (3R)-1-(4-((4,4,4-trifluoro-1-(3-methylbiphenyl-4-yl)-butyl)amino)benzoyl)-piperidine-3-carboxylic acid | 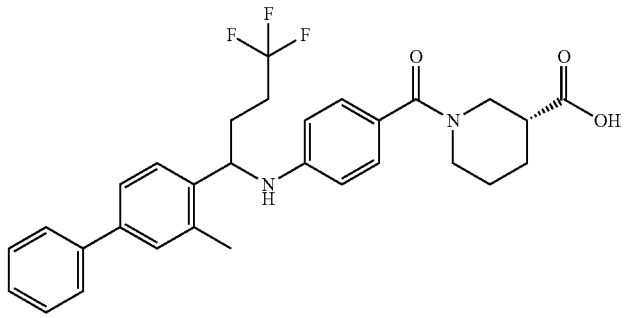 [SMILES: Cc1cc(-c2ccccc2)ccc1C(CCC(F)(F)F)Nc1ccc(C(=O)N2CCC[C@@H](C(=O)O)C2)cc1] | 525.4 |
| 80 | (3R)-1-(4-((1-(4-(6-(cyclopropylmethoxy)-pyridin-3-yl)-2-methylphenyl)-4,4,4-trifluorobutyl)amino)-benzoyl)piperidine-3-carboxylic acid | 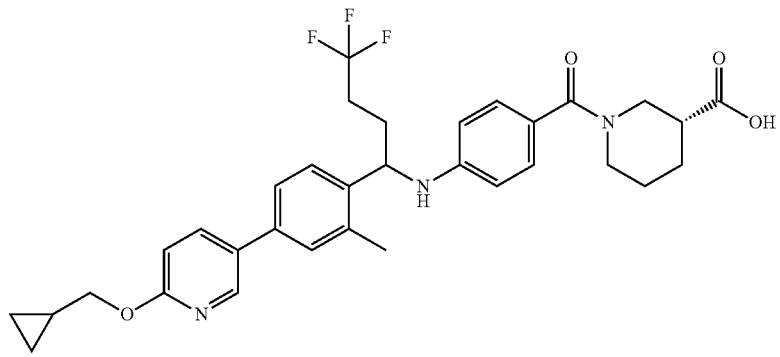 [SMILES: Cc1cc(-c2ccc(OCC3CC3)nc2)ccc1C(CCC(F)(F)F)Nc1ccc(C(=O)N2CCC[C@@H](C(=O)O)C2)cc1] | 596.3 |

TABLE 9

| 81 | (3R)-1-(4-((1-(4-(2-ethoxypyrimidin-5-yl)-2-methylphenyl)-4,4,4-trifluorobutyl)amino)-benzoyl)piperidine-3-carboxylic acid | 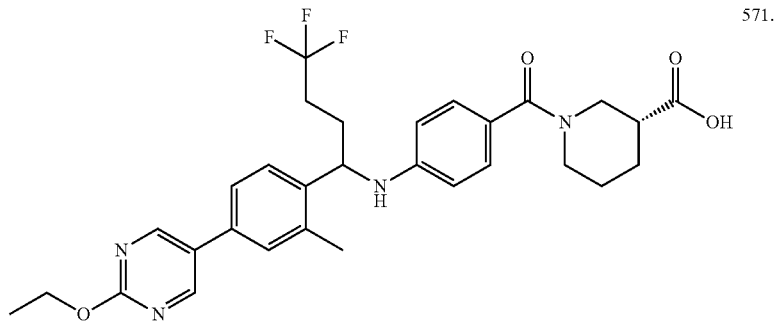 | 571.3 |
| 82 | (3R)-1-(4-((1-(4-(1-tert-butyl-1H-pyrazol-4-yl)-2-methylphenyl)-4,4,4-trifluorobutyl)-amino)benzoyl)-piperidine-3-carboxylic acid | 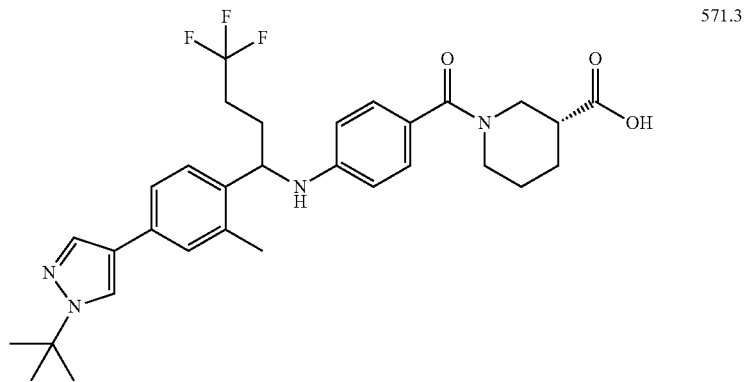 | 571.3 |
| 83 | (3R)-1-(4-((4,4,4-trifluoro-1-(4-(1-isopropyl-1H-pyrazol-4-yl)-2-methylphenyl)-butyl)amino)benzoyl)-piperidine-3-carboxylic acid | 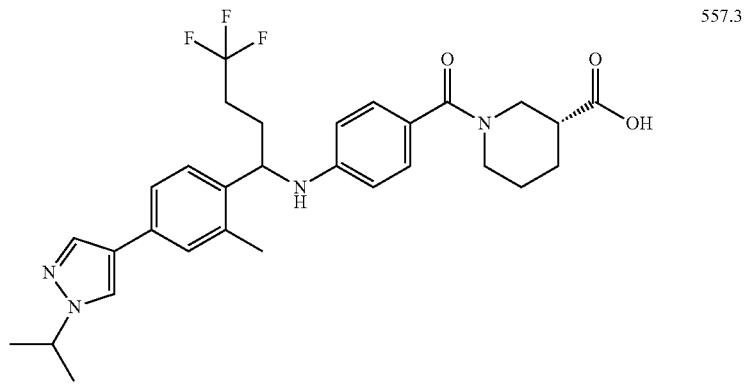 | 557.3 |
| 84 | (3R)-1-(4-((4,4,4-trifluoro-1-(4-(1-(4-fluorophenyl)-1H-pyrazol-4-yl)-2-methylphenyl)butyl-amino)benzoyl)-piperidine-3-carboxylic acid | 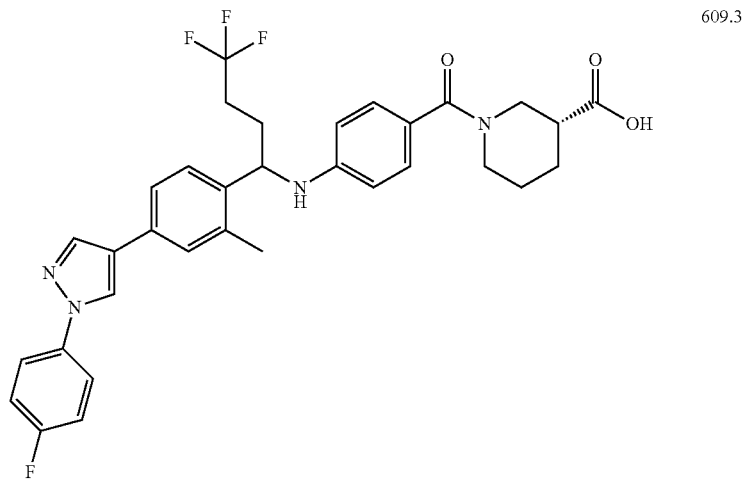 | 609.3 |

TABLE 9-continued

| 85 | (3R)-1-(4-((1-(4-(5-chloropyridin-2-yl)-2-methylphenyl)-4,4,4-trifluorobutyl)amino)-benzoyl)piperidine-3-carboxylic acid | 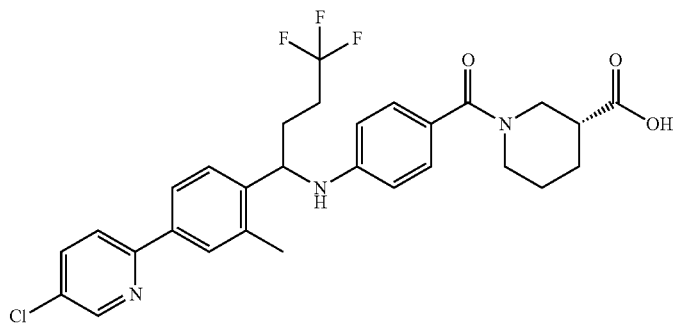 [SMILES: Cc1cc(-c2ccc(Cl)cn2)ccc1C(CCC(F)(F)F)Nc1ccc(C(=O)N2CCC[C@@H](C(=O)O)C2)cc1] | 560.3 |
| 86 | (3R)-1-(4-((4,4,4-trifluoro-1-(2-methyl-4-(5-(trifluoromethyl)-pyridin-3-yl)phenyl)-butyl)amino)benzoyl)-piperidine-3-carboxylic acid | 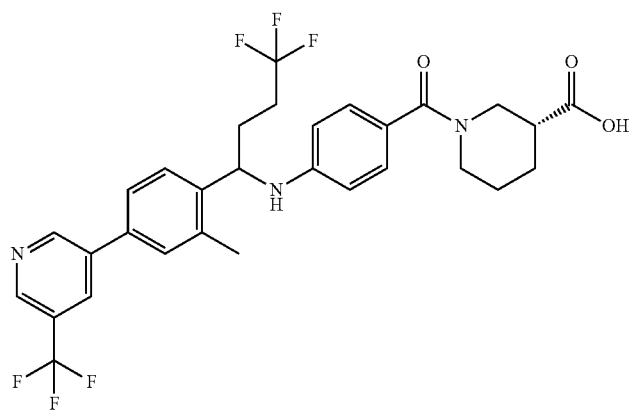 [SMILES: Cc1cc(-c2cncc(C(F)(F)F)c2)ccc1C(CCC(F)(F)F)Nc1ccc(C(=O)N2CCC[C@@H](C(=O)O)C2)cc1] | 594.3 |
| 87 | (3R)-1-(4-((4,4,4-trifluoro-1-(2-methyl-4-(4-(trifluoromethyl)-pyridin-2-yl)phenyl)-butyl)amino)benzoyl)-piperidine-3-carboxylic acid | 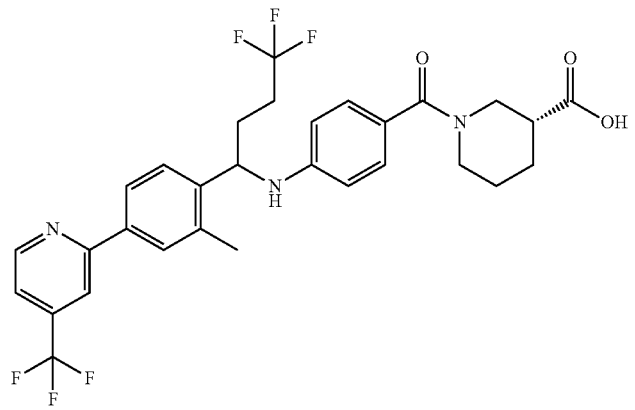 [SMILES: Cc1cc(-c2cc(C(F)(F)F)ccn2)ccc1C(CCC(F)(F)F)Nc1ccc(C(=O)N2CCC[C@@H](C(=O)O)C2)cc1] | 594.2 |
| 88 | (3R)-1-(4-((4,4,4-trifluoro-1-(2-methyl-4-(2-(trifluoromethyl)-pyrimidin-5-yl)phenyl)-butyl)amino)benzoyl)-piperidine-3-carboxylic acid | 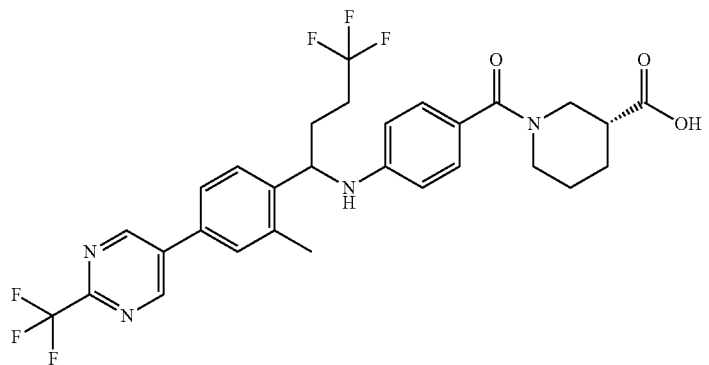 [SMILES: Cc1cc(-c2cnc(C(F)(F)F)nc2)ccc1C(CCC(F)(F)F)Nc1ccc(C(=O)N2CCC[C@@H](C(=O)O)C2)cc1] | 595.2 |

TABLE 9-continued

| 89 | (3R)-1-(4-((4,4,4-trifluoro-1-(2-methyl-4-(6-(trifluoromethyl)-pyridin-2-yl)phenyl)-butyl)amino)benzoyl)-piperidine-3-carboxylic acid | 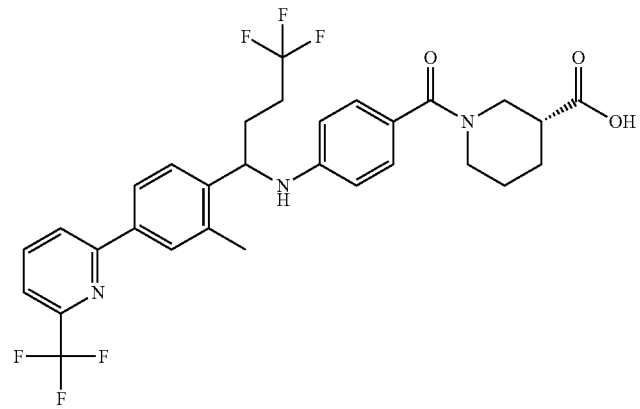 [SMILES: Cc1cc(-c2cccc(C(F)(F)F)n2)ccc1C(CCC(F)(F)F)Nc1ccc(C(=O)N2CCC[C@@H](C(=O)O)C2)cc1] | 594.3 |
| 90 | (3R)-1-(4-((4,4,4-trifluoro-1-(4-(3-fluoro-5-(trifluoromethyl)-pyridin-2-yl)-2-methylphenyl)butyl)-amino)benzoyl)-piperidine-3-carboxylic acid | 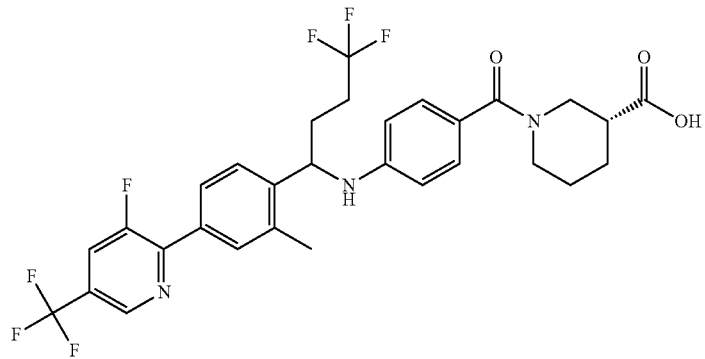 [SMILES: Cc1cc(-c2ncc(C(F)(F)F)cc2F)ccc1C(CCC(F)(F)F)Nc1ccc(C(=O)N2CCC[C@@H](C(=O)O)C2)cc1] | 612.3 |

TABLE 10

| 91 | (3R)-1-(4-((4,4,4-trifluoro-1-(2-methyl-4-(4-(trifluoromethyl)-pyrimidin-2-yl)phenyl)-butyl)amino)benzoyl)-piperidine-3-carboxylic acid | 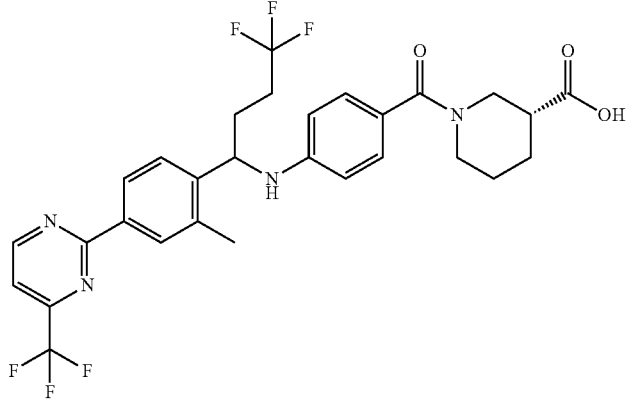 [SMILES: Cc1cc(-c2nccc(C(F)(F)F)n2)ccc1C(CCC(F)(F)F)Nc1ccc(C(=O)N2CCC[C@@H](C(=O)O)C2)cc1] | 595.3 |
| 92 | (3R)-1-(4-((4,4,4-trifluoro-1-(2-methyl-4-(5-(trifluoromethyl)-pyrazin-2-yl)phenyl)-butyl)amino)benzoyl)-piperidine-3-carboxylic acid | 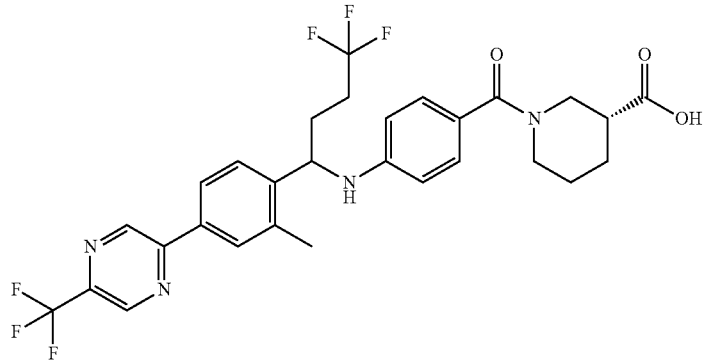 [SMILES: Cc1cc(-c2cnc(C(F)(F)F)cn2)ccc1C(CCC(F)(F)F)Nc1ccc(C(=O)N2CCC[C@@H](C(=O)O)C2)cc1] | 595.3 |

TABLE 10-continued

| 93 | (3R)-1-(4-((4,4,4-trifluoro-1-(2-methyl-4-(6-(trifluoromethyl)-pyridazin-3-yl)phenyl)-butyl)amino)benzoyl)-piperidine-3-carboxylic acid | 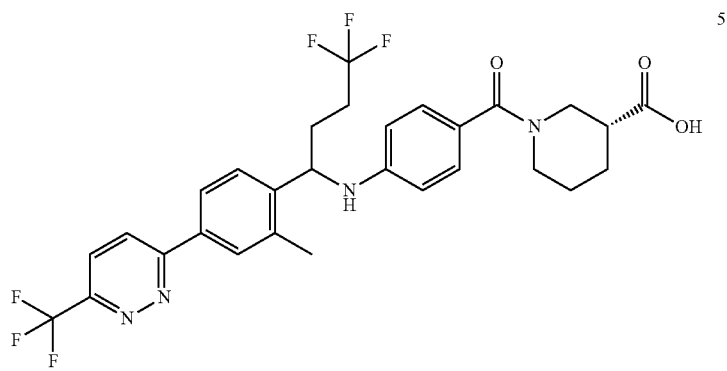 | 595.3 |
| 94 | (3R)-1-(4-((1-(4-(5-ethylpyridin-2-yl)-2-methylphenyl)-4,4,4-trifluorobutyl)amino)-benzoyl)piperidine-3-carboxylic acid | 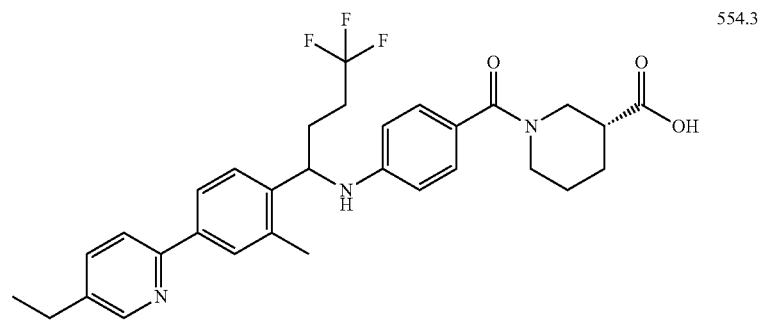 | 554.3 |
| 95 | (3R)-1-(4-((1-(4'-chloro-2-methylbiphenyl-4-yl)-4,4,4-trifluorobutyl)-amino)benzoyl)-piperidine-3-carboxylic acid | 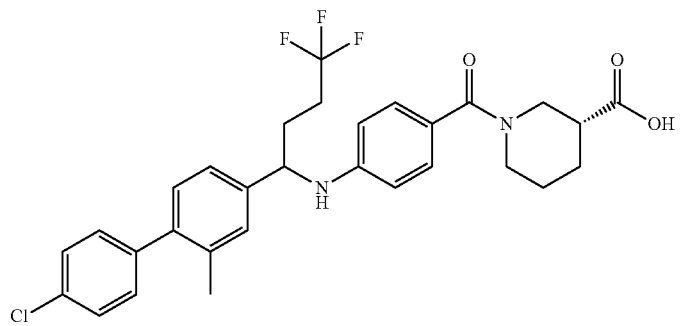 [SMILES: Cc1cc(C(CCC(F)(F)F)Nc2ccc(C(=O)N3CCC[C@@H](C(=O)O)C3)cc2)ccc1-c1ccc(Cl)cc1] | 559.3 |
| 96 | (3R)-1-(4-((4,4,4-trifluoro-1-(2-methyl-4-(1H-pyrazol-1-yl)phenyl)butyl)amino)-benzoyl)piperidine-3-carboxylic acid | 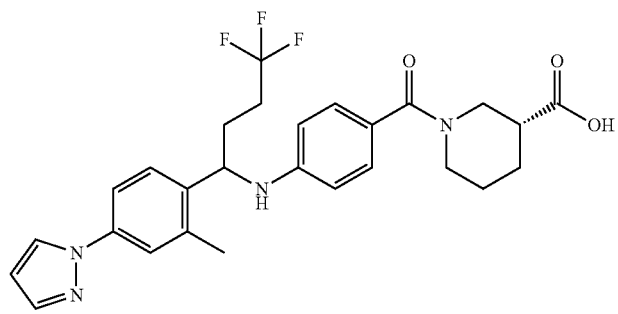 [SMILES: Cc1cc(-n2cccn2)ccc1C(CCC(F)(F)F)Nc1ccc(C(=O)N2CCC[C@@H](C(=O)O)C2)cc1] | 515.2 |

TABLE 10-continued

| 97 | (3R)-1-(4-((4,4,4-trifluoro-1-(2-methyl-4-(3-methyl-1H-pyrazol-1-yl)phenyl)butyl)-amino)benzoyl)-piperidine-3-carboxylic acid | 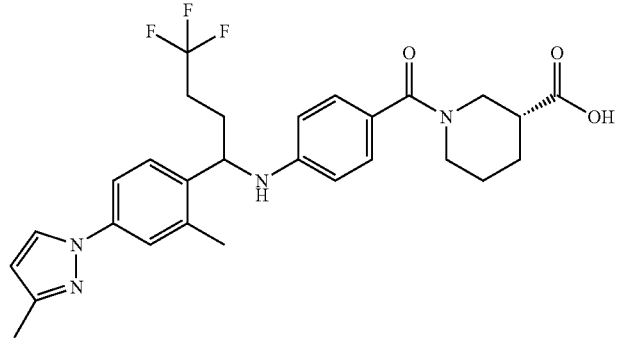 [SMILES: Cc1ccn(-c2ccc(C(CCC(F)(F)F)Nc3ccc(C(=O)N4CCC[C@@H](C(=O)O)C4)cc3)c(C)c2)n1] | 529.2 |
| 98 | (3R)-1-(4-((4,4,4-trifluoro-1-(4-(5-isopropyl-1H-pyrazol-1-yl)-2-methylphenyl)-butyl)amino)benzoyl)-piperidine-3-carboxylic acid | 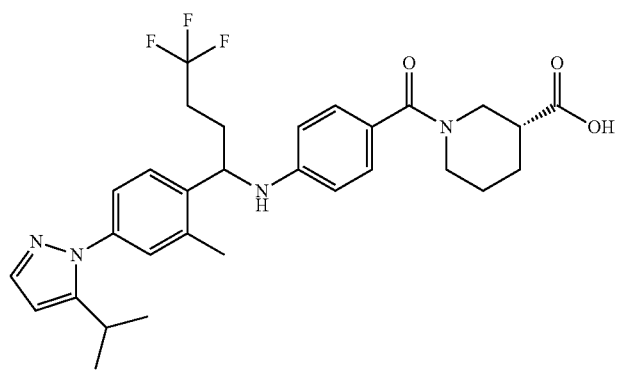 [SMILES: Cc1cc(-n2nccc2C(C)C)ccc1C(CCC(F)(F)F)Nc1ccc(C(=O)N2CCC[C@@H](C(=O)O)C2)cc1] | 557.3 |
| 99 | (3R)-1-(4-((1-(4-(3-tert-butyl-1H-pyrazol-1-yl)-2-methylphenyl)-4,4,4-trifluorobutyl)-amino)benzoyl)-piperidine-3-carboxylic acid | 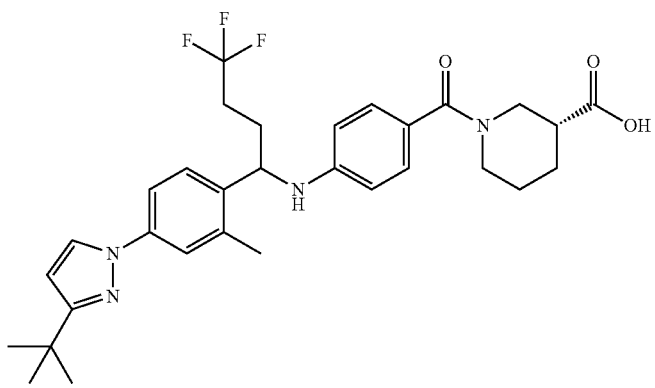 [SMILES: Cc1cc(-n2ccc(C(C)(C)C)n2)ccc1C(CCC(F)(F)F)Nc1ccc(C(=O)N2CCC[C@@H](C(=O)O)C2)cc1] | 571.3 |
| 100 | (3R)-1-(4-((1-(4-(4-tert-butyl-1H-1,2,3-triazol-1-yl)-2-methylphenyl)-4,4,4-trifluorobutyl)amino)-benzoyl)piperidine-3-carboxylic acid | 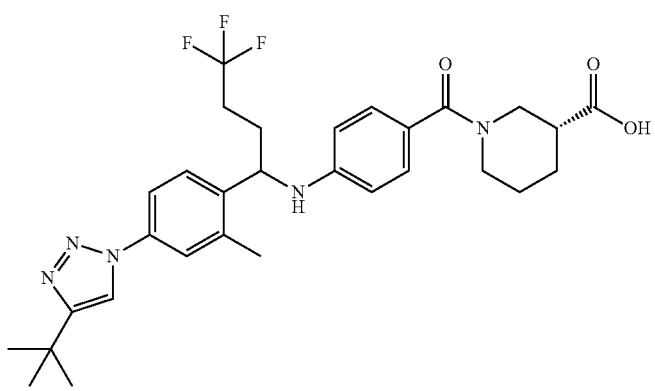 [SMILES: Cc1cc(-n2cc(C(C)(C)C)nn2)ccc1C(CCC(F)(F)F)Nc1ccc(C(=O)N2CCC[C@@H](C(=O)O)C2)cc1] | 572.3 |

TABLE 11

| | | | |
|---|---|---|---|
| 101 | (3R)-1-(4-((1-(4-(4-tert-butyl-2H-1,2,3-triazol-2-yl)-2-methylphenyl)-4,4,4-trifluorobutyl)amino)benzoyl)piperidine-3-carboxylic acid | 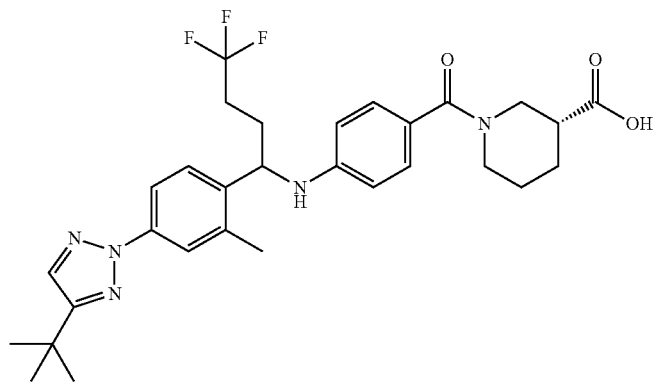 [SMILES: Cc1cc(-n2ncc(C(C)(C)C)n2)ccc1C(CCC(F)(F)F)Nc1ccc(C(=O)N2CCC[C@@H](C(=O)O)C2)cc1] | 572.3 |
| 102 | (3R)-1-(4-((4,4,4-trifluoro-1-(2-methyl-4-(3-(trifluoromethyl)-1H-pyrazol-1-yl)-phenyl)butyl)amino)-benzoyl)piperidine-3-carboxylic acid | 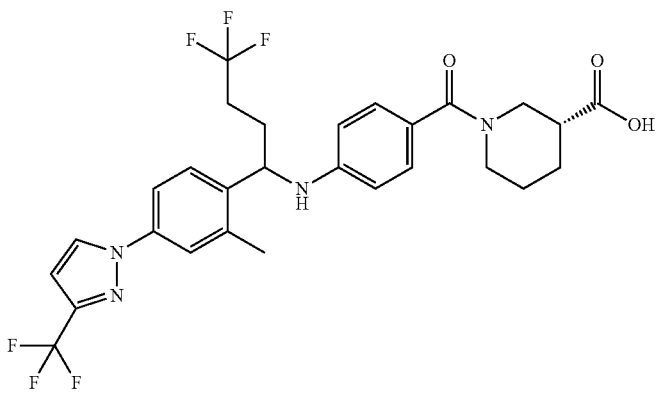 [SMILES: Cc1cc(-n2ccc(C(F)(F)F)n2)ccc1C(CCC(F)(F)F)Nc1ccc(C(=O)N2CCC[C@@H](C(=O)O)C2)cc1] | 583.3 |
| 103 | (3R)-1-(4-((4,4,4-trifluoro-1-(2-methyl-4-(4-(trifluoromethyl)-1H-pyrazol-1-yl)-phenyl)butyl)amino)-benzoyl)piperidine-3-carboxylic acid | 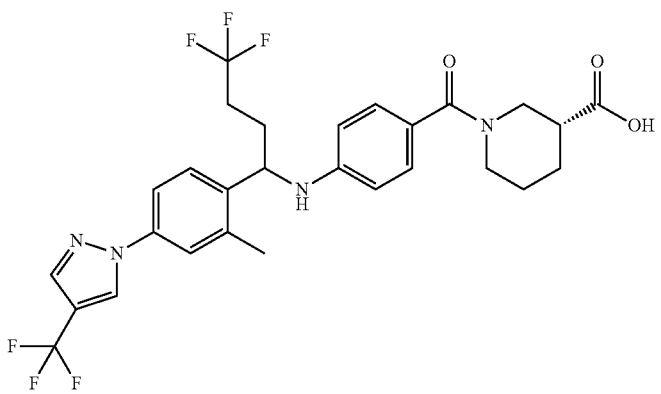 [SMILES: Cc1cc(-n2cc(C(F)(F)F)cn2)ccc1C(CCC(F)(F)F)Nc1ccc(C(=O)N2CCC[C@@H](C(=O)O)C2)cc1] | 583.2 |
| 104 | (3R)-1-(4-((1-(4-(3-cyclopropyl-1H-pyrazol-1-yl)-2-methylphenyl)-4,4,4-trifluorobutyl)-amino)benzoyl)-piperidine-3-carboxylic acid | 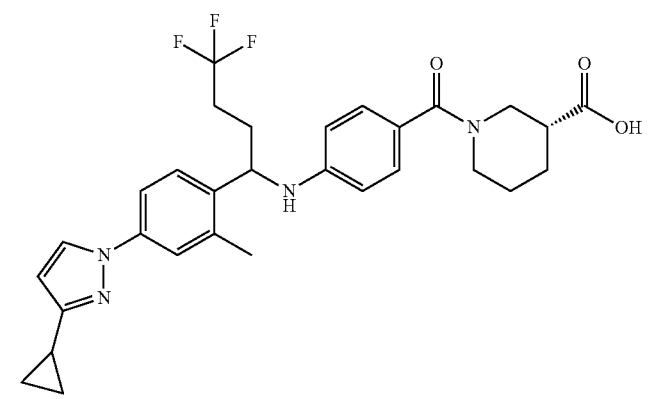 [SMILES: Cc1cc(-n2ccc(C3CC3)n2)ccc1C(CCC(F)(F)F)Nc1ccc(C(=O)N2CCC[C@@H](C(=O)O)C2)cc1] | 555.3 |

| | | | |
|---|---|---|---|
| 105 | (3R)-1-(4-((1-(4-(5,5-difluoro-4,5,6,7-tetrahydro-2H-indazol-2-yl)-2-methylphenyl)-4,4,4-trifluorobutyl)-amino)benzoyl)-piperidine-3-carboxylic acid | 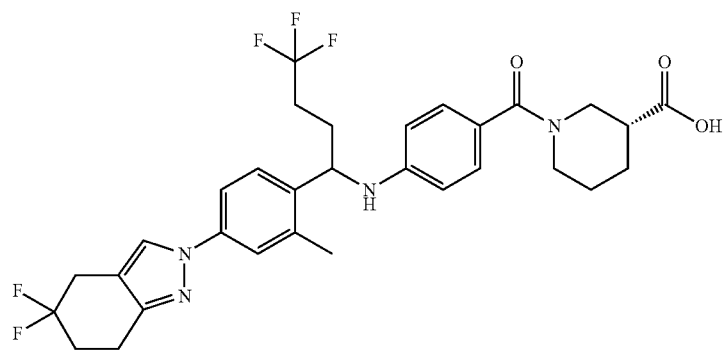 [SMILES: Cc1cc(-n2cc3c(n2)CCC(F)(F)C3)ccc1C(CCC(F)(F)F)Nc1ccc(C(=O)N2CCC[C@@H](C(=O)O)C2)cc1] | 605.3 |
| 106 | (3R)-1-(4-((1-(4-(3-ethyl-4-methyl-1H-pyrazol-1-yl)-2-methylphenyl)-4,4,4-trifluorobutyl)amino)-benzoyl)piperidine-3-carboxylic acid | 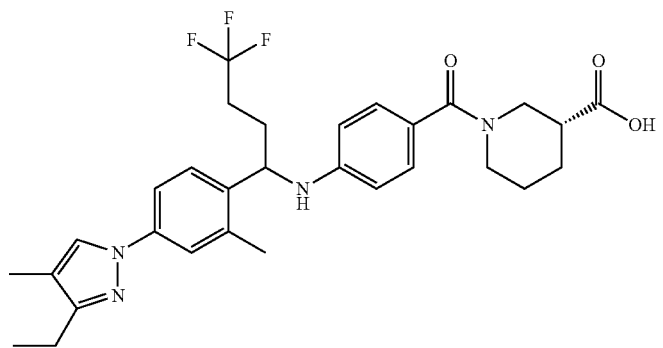 [SMILES: CCc1nn(-c2ccc(C(CCC(F)(F)F)Nc3ccc(C(=O)N4CCC[C@@H](C(=O)O)C4)cc3)c(C)c2)cc1C] | 557.3 |
| 107 | (3R)-1-(4-((4,4,4-trifluoro-1-(4-(5-fluoro-1H-indazol-1-yl)-2-methylphenyl)-butyl)amino)benzoyl)-piperidine-3-carboxylic acid | 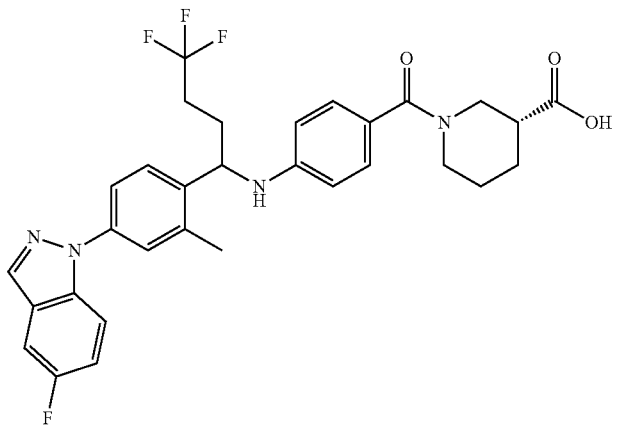 [SMILES: Cc1cc(-n2ncc3cc(F)ccc32)ccc1C(CCC(F)(F)F)Nc1ccc(C(=O)N2CCC[C@@H](C(=O)O)C2)cc1] | 583.3 |
| 108 | (3R)-1-(4-((4,4,4-trifluoro-1-(4-(5-fluoro-2H-indazol-2-yl)-2-methylphenyl)-butyl)amino)benzoyl)-piperidine-3-carboxylic acid | 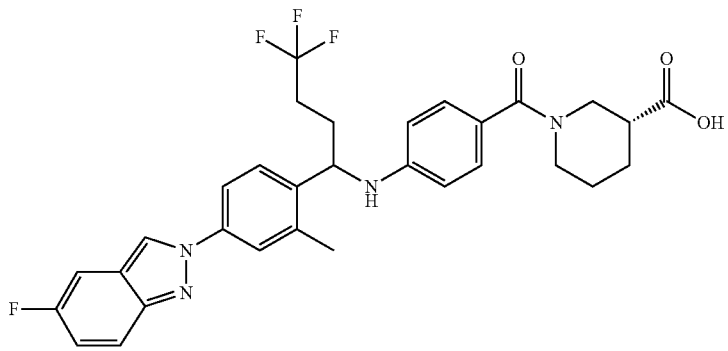 [SMILES: Cc1cc(-n2cc3cc(F)ccc3n2)ccc1C(CCC(F)(F)F)Nc1ccc(C(=O)N2CCC[C@@H](C(=O)O)C2)cc1] | 583.3 |

TABLE 11-continued

| | | | |
|---|---|---|---|
| 109 | (3R)-1-(4-((4,4,4-trifluoro-1-(2-methyl-4-(4,5,6,7-tetrahydro-1,3-benzooxazol-2-yl)phenyl)butyl)amino)-benzoyl)piperidine-3-carboxylic acid | 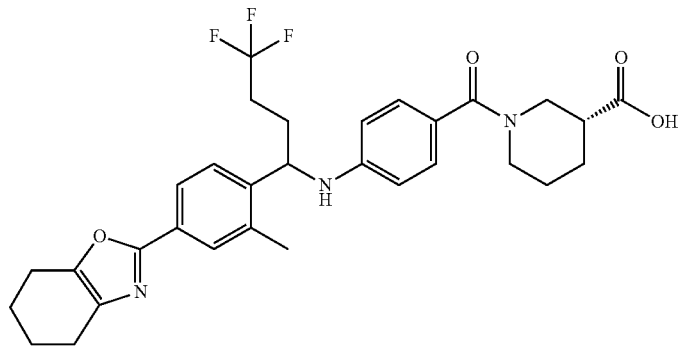 [SMILES: Cc1cc(-c2nc3c(o2)CCCC3)ccc1C(CCC(F)(F)F)Nc1ccc(C(=O)N2CCC[C@@H](C(=O)O)C2)cc1] | 570.3 |
| 110 | (3R)-1-(4-((4,4,4-trifluoro-1-(4-(5-isopropyl-1,3-oxazol-2-yl)-2-methylphenyl)-butyl)amino)benzoyl)-piperidine-3-carboxylic acid | 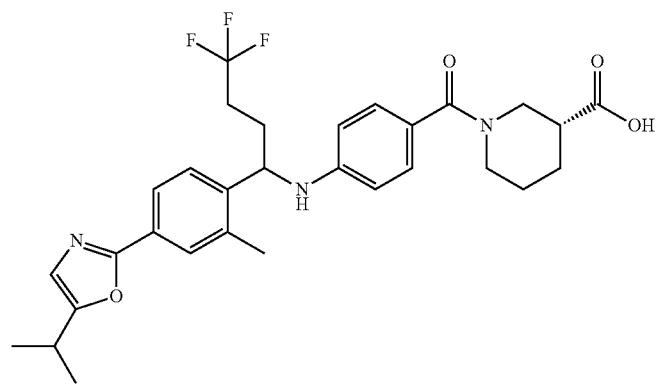 [SMILES: Cc1cc(-c2ncc(C(C)C)o2)ccc1C(CCC(F)(F)F)Nc1ccc(C(=O)N2CCC[C@@H](C(=O)O)C2)cc1] | 558.3 |

TABLE 12

| | | | |
|---|---|---|---|
| 111 | (3R)-1-(4-((1-(6-(4-chlorophenyl)pyridin-3-yl)-4,4,4-trifluorobutyl)-amino)benzoyl)-piperidine-3-carboxylic acid | 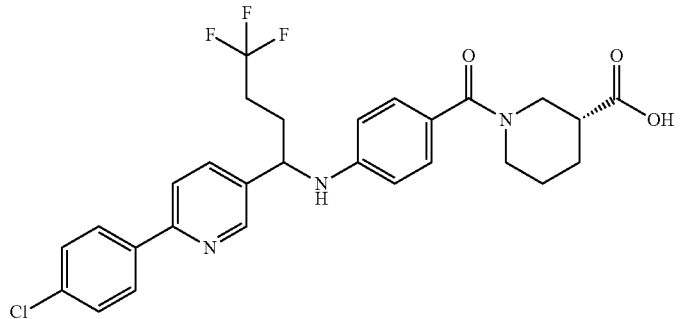 | 546.3 |
| 112 | (3R)-1-(4-((1-(4-(5-ethylpyrimidin-2-yl)-2-methylphenyl)-2-methylpropyl)amino)-benzoyl)piperidine-3-carboxylic acid | 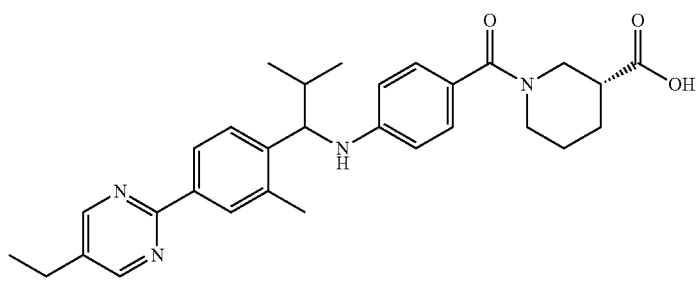 [SMILES: CCc1cnc(-c2ccc(C(Nc3ccc(C(=O)N4CCC[C@@H](C(=O)O)C4)cc3)C(C)C)c(C)c2)nc1] | 501.6 |

TABLE 12-continued

| | | | |
|---|---|---|---|
| 113 | (3R)-1-(4-((4,4,4-trifluoro-1-(4'-methylbiphenyl-4-yl)-butyl)amino)benzoyl)-piperidine-3-carboxylic acid | 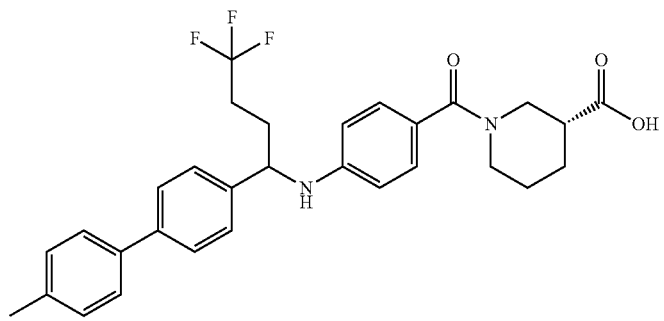 [SMILES: Cc1ccc(-c2ccc(C(CCC(F)(F)F)Nc3ccc(C(=O)N4CCC[C@@H](C(=O)O)C4)cc3)cc2)cc1] | 525.3 |
| 114 | (3R)-1-(4-((4,4,4-trifluoro-1-(4'-(trifluoromethyl)biphenyl-4-yl)butyl)amino)-benzoyl)piperidine-3-carboxylic acid | 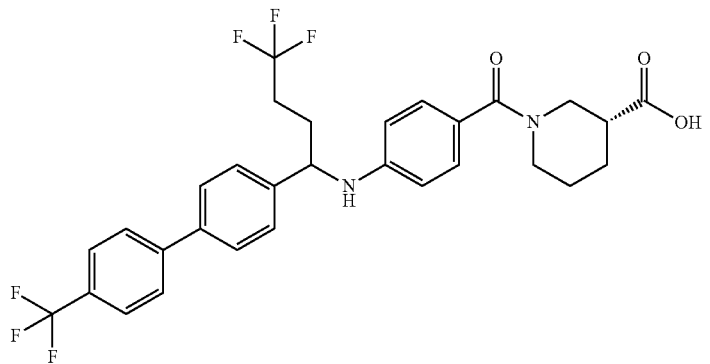 [SMILES: O=C(O)[C@@H]1CCCN(C(=O)c2ccc(NC(CCC(F)(F)F)c3ccc(-c4ccc(C(F)(F)F)cc4)cc3)cc2)C1] | 579.2 |
| 115 | (3R)-1-((6-((4,4,4-trifluoro-1-(4'-methylbiphenyl-4-yl)butyl)amino)pyridin-3-yl)carbonyl)-piperidine-3-carboxylic acid | 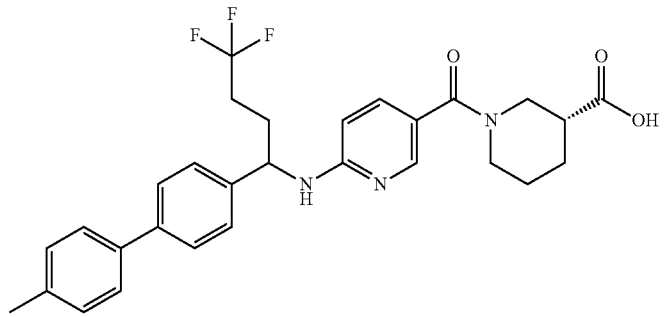 [SMILES: Cc1ccc(-c2ccc(C(CCC(F)(F)F)Nc3ccc(C(=O)N4CCC[C@@H](C(=O)O)C4)cn3)cc2)cc1] | 526.3 |
| 116 | (3R)-1-(4-((2-methyl-1-(2-methyl-4-(4,5,6,7-tetrahydro-2H-indazol-2-yl)phenyl)propyl)-amino)benzoyl)-piperidine-3-carboxylic acid | 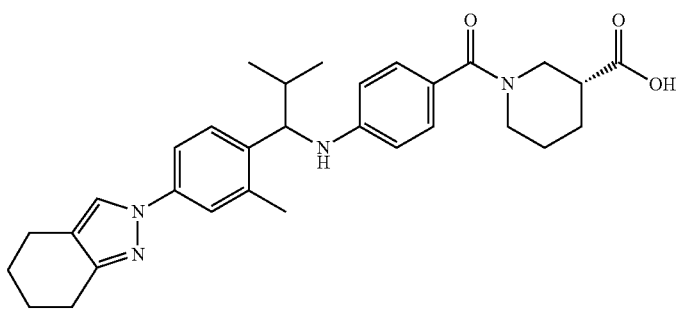 [SMILES: Cc1cc(-n2cc3c(n2)CCCC3)ccc1C(Nc1ccc(C(=O)N2CCC[C@@H](C(=O)O)C2)cc1)C(C)C] | 515.6 |
| 117 | (3R)-1-(4-((2-methyl-1-(2-methyl-4-(4,5,6,7-tetrahydro-2H-indazol-2-yl)phenyl)propyl)-amino)benzoyl)-piperidine-3-carboxylic acid | 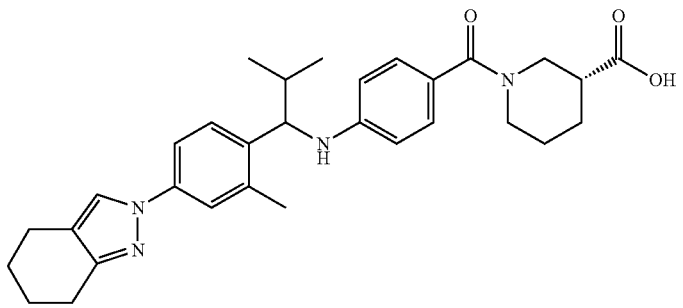 [SMILES: Cc1cc(-n2cc3c(n2)CCCC3)ccc1C(Nc1ccc(C(=O)N2CCC[C@@H](C(=O)O)C2)cc1)C(C)C] | 515.4 |

Experimental Example 1

The glucagon binding inhibitory action of the compound of the present invention was evaluated by the following method.
(1) Cloning of Human Glucagon Receptor Gene Human glucagon receptor gene was cloned by PCR reaction using human pancreas Marathon-ready cDNA (Clontech Laboratories, Inc.) as a template and the following primer set.
GGR-U:
5'-AATAGAATTCATGCCCCCCTGCCAGCCACAG-3' (SEQ ID NO: 1)
GGR-L:
5'-CTAAGCGGCCGCTCAGAAGGGGCTCT-CAGCCAATCT-3' (SEQ ID NO: 2)

The PCR reaction was performed using Advantage 2 polymerase (Clontech Laboratories, Inc.) and according to the attached protocol. The obtained PCR product was subjected to agarose gel (1%) electrophoresis, an about 1.4 kb DNA fragment containing glucagon receptor gene was recovered from the gel, and digested with restriction enzymes EcoRI and NotI. The restriction enzyme-treated DNA was subjected to agarose gel (1%) electrophoresis, an about 1.4 kb DNA fragment was recovered and ligated with plasmid pMSRaneo digested with restriction enzymes EcoRI and NotI to give human type glucagon receptor expression plasmid DNA "pMSRaneo/hGCGR". The base sequence of the inserted fragment was confirmed to be identical with the object sequence.

(2) Preparation of Glucagon Receptor Membrane Protein

Human type glucagon receptor was expressed using FreeStyle CHO Expression System (Invitrogen™). According to the manual attached to the FreeStyle CHO Expression System, and using the human type glucagon receptor expression plasmid DNA "pMSRaneo/hGCGR" produced in the abovementioned (1), transient expression was performed by FreeStyle CHO cells. The above-mentioned DNA was transfected, and shaking culture was performed at 37° C., 8% $CO_2$, 125 rpm for 2 days. The culture medium was centrifuged at 2,000 rpm for 10 min and the cells were recovered. The recovered cells were washed with PBS, suspended in homogenate buffer [10 mM $NaHCO_3$ (pH 7.4), 1 mM EDTA, complete EDTA-free (Roche, Ltd., 1 tablet/50 ml)], and the cells were disrupted by a Polytron cell disruption apparatus (Kinematica AG). The disruption solution was centrifuged at 2,000 rpm for 10 min, and the supernatant was recovered. The supernatant was centrifuged at 35,000 rpm for 60 min, and the precipitate was suspended in a buffer [20 mM Tris-HCl (pH 7.4), 5 mM EDTA, complete EDTA-free (Roche, Ltd., 1 tablet/50 ml)] to give a glucagon receptor membrane protein.

(3) Measurement of Glucagon Binding Inhibitory Activity

The reaction was started by adding 50 µl of a glucagon receptor membrane protein solution diluted with a reaction buffer [50 mM HEPES (pH 7.4), 5 mM EGTA, 5 mM magnesium chloride, 0.1% BSA, 0.005% Tween20] to 100 µg/ml, 25 µl of a test compound solution containing 0.4% DMSO, which solution was prepared with the reaction buffer to a compound concentration of 40 µM, and 25 µl of radiolabeled glucagon ([$^{125}$I]-Receptor Grade Glucagon; Perkin Elmer Inc.) diluted with the reaction buffer to 200 pM to each well of a 96 well plate (Corning Incorporated). The plate was stood at room temperature for 90 min, then the reaction solution was transferred from the reaction plate onto a 96 well unifilter GF/C plate (Perkin Elmer Inc.) by a cell harvester (Perkin Elmer Inc.), and suctioned to collect a membrane fraction on the filter. The filter was immersed in a 0.3% polyethyleneimine solution in advance to prevent non-specific adsorption of the labeled ligand. The filter was washed 4 times with the reaction buffer, and dried at 42° C. for 2 hr. To each well was added 25 µl of scintillator (MicroScint0; Perkin Elmer Inc.), and the amount of fluorescence was measured by a microplate scintillation counter (TopCount NXT™; Perkin Elmer Inc.).

The inhibitory rate (%) of the well added with the test compound (10 µM; containing 0.4% DMSO solution) was calculated wherein the reaction rate of the well added with 0.4% DMSO alone was 0% inhibitory rate and that of the well added with unlabeled glucagon (final concentration 1 µM) was 100% inhibitory rate. The results are shown in Table 13.

TABLE 13

| test compound (Ex. No.) | inhibitory rate (%) at 10 µM |
|---|---|
| 1 | 84 |
| 2 | 92 |
| 3 | 91 |
| 4 | 95 |
| 5 | 86 |
| 6 | 85 |
| 7 | 91 |
| 8 | 91 |
| 9 | 90 |
| 10 | 88 |
| 11 | 93 |
| 12 | 96 |
| 13 | 84 |
| 14 | 88 |
| 15 | 92 |
| 16 | 93 |
| 17 | 92 |
| 18 | 86 |
| 19 | 87 |
| 20 | 93 |
| 21 | 90 |
| 22 | 89 |
| 23 | 90 |
| 24 | 84 |
| 25 | 71 |
| 26 | 88 |
| 27 | 86 |
| 28 | 98 |
| 112 | 90 |
| 116 | 90 |
| 117 | 90 |

As mentioned above, the compound of the present invention was shown to have a superior glucagon binding inhibitory action, i.e., glucagon receptor antagonistic action.

Experimental Example 2

Hypoglycemic Action in Wistar Fatty Rat (Single Administration)

Wistar fatty rats (male, 25- to 26-week-old) were orally administered with a 0.5% methylcellulose suspension containing a test compound (10 mg/kg body weight) (test compound administration group, 4-6 per group) or 0.5% methylcellulose solution (test compound non-administration group, 4-6 per group), blood samples were collected from the rat tail vein 4 hr after the administration, and the hypoglycemic action was evaluated using the blood. The blood glucose was measured using Model 7180 HITACHI automatic analyzer (Hitachi, Ltd.).

In each animal of the test compound administration group and the test compound non-administration group, changes in the blood glucose level from that before administration was calculated, the difference between the "average change of test compound non-administration group" and the "change in each animal of test compound administration group" was calculated as the "change in blood glucose due to test compound", and the average of each group was taken as the "blood glucose change value (mg/dL)". The results are shown in Table 14.

TABLE 14

| test compound | compound dose (mg/kg) | blood glucose change value (mg/dL) |
|---|---|---|
| Example 1 | 10 | −162.9 |
| Example 2 | 10 | −149.8 |
| Example 3 | 10 | −142.5 |
| Example 4 | 10 | −130.4 |
| Example 21 | 10 | −136.0 |

As mentioned above, the compound of the present invention was shown to have a superior hypoglycemic action in vivo.

Experimental Example 3

Suppressive Action on Hyperglycemia after Eating in Streptozotocin (STZ)-Induced Type 1 Diabetes Model Rat Bred with Time-Limited Feeding Type 1 diabetes model STZ rat was generated by intravenously administering streptozotocin (STZ: Wako Pure Chemical Industries, Ltd., 65 mg/kg) after overnight fasting. From 1 week after the STZ treatment, time-limited feeding (feeding twice per day for 2 hours each time at 9:00-11:00 am and 16:00-18:00 pm) was started. On day 6 of breeding with time-limited feeding, blood samples were collected immediately before feeding in the morning and after 2 hours of feeding (immediately before end of feeding), and the rats were divided into two groups of detemir (long-acting insulin preparation) treatment group and detemir non-treatment group, with an increase in the plasma glucose concentration associated with the feed intake as an index. In the detemir treatment group, repeated subcutaneous administration of detemir (10 U/kg body weight, Novo Nordisk Pharma Ltd., once per day) was started after the end of feeding in the afternoon, and continued for 7 days until one day before evaluation of the influence of compound administration. Similarly, the detemir non-treatment group was subcutaneously administered repeatedly with saline for 7 days.

The day after repeated administration of detemir for 3 days, blood samples were collected in the same manner as above, and the animals in the detemir treatment group were divided into 3 groups based on an increase in the plasma glucose concentration associated with the feed intake. Each group was orally administered repeatedly with a 0.5% methylcellulose (MC) suspension containing the compound of Example 3 or 21 (10 mg/kg, q.d.) (8 per each group), or 0.5% methylcellulose solution (compound non-administration group, 8) for 4 days before feeding in the morning, starting from the next day of repeated administration of detemir for 4 days.

The next day of repeated administration of detemir for 7 days (the next day of repeated administration of compound for 3 days), blood samples were collected immediately before the start of feeding (and each compound administration) in the morning to obtain values before administration. Also, blood samples were collected after 1 and 2 hours of the administration (immediately before end of feeding), and an influence of compound administration on the profile of plasma glucose concentration after feed intake was evaluated. The results are shown in Table 15.

Throughout the test, blood samples were collected from the tail vein, and the plasma glucose concentration was measured using Model 7180 HITACHI automatic analyzer.

TABLE 15

| compound (p.o.) | detemir (s.c.) | n | average plasma glucose concentration (mg/dL) | | |
|---|---|---|---|---|---|
| | | | value before administration | 1 hr | 2 hr |
| 0.5% MC | 10 U/kg | 8 | 372.6 | 635.8 | 680.3 |
| Example 3 10 mg/kg | 10 U/kg | 8 | 397.0 | 463.6 | 555.2 |
| Example 21 10 mg/kg | 10 U/kg | 8 | 435.6 | 471.1 | 552.0 |
| 0.5% MC | saline | 8 | 537.9 | 697.1 | 731.0 |

As mentioned above, the compound of the present invention showed a superior suppressive action on hyperglycemia after eating in type 1 diabetes animal model.

| Formulation Example 1 (production of capsule) | | |
|---|---|---|
| 1) | compound of Example 1 | 30 mg |
| 2) | finely divided powder cellulose | 10 mg |
| 3) | lactose | 19 mg |
| 4) | magnesium stearate | 1 mg |
| | total | 60 mg |

1), 2), 3) and 4) are mixed and filled in a gelatin capsule.

| Formulation Example 2 (production of tablets) | | |
|---|---|---|
| 1) | compound of Example 1 | 30 g |
| 2) | lactose | 50 g |
| 3) | cornstarch | 15 g |
| 4) | calcium carboxymethylcellulose | 44 g |
| 5) | magnesium stearate | 1 g |
| 1000 tablets | total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention or a salt thereof has a superior glucagon receptor antagonistic action, and is useful as a glucagon receptor antagonist, a glucose production inhibitor, or an agent for the prophylaxis or treatment of diabetes and the like.

This application is based on patent application No. 2012-078133 filed in Japan, the contents of which are encompassed in full herein.

The invention claimed is:

1. A compound represented by the formula (I):

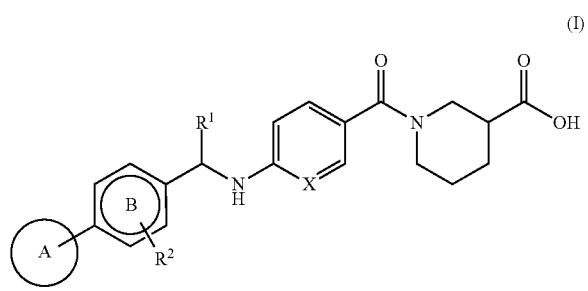

wherein ring A is an optionally further substituted 5- or 6-membered aromatic ring, and the 5- or 6-membered aromatic ring is optionally fused with an optionally substituted 5- to 7-membered ring;
ring B is an optionally further substituted 6-membered aromatic ring;
$R^1$ is $C_{1-6}$ alkyl optionally substituted by a halogen atom, or $C_{3-10}$ cycloalkyl optionally substituted by a halogen atom;
$R^2$ is a hydrogen atom, a halogen atom, or $C_{1-6}$ alkyl optionally substituted by a halogen atom; and
X is CH or N,
or a salt thereof.

2. The compound according to claim 1, wherein ring A is a benzene ring, a pyrrole ring, a pyrazole ring, an oxazole ring, an isoxazole ring, a triazole ring, a pyridine ring, a pyridazine ring, a pyrimidine ring or a pyrazine ring, each of which is optionally further substituted, or a salt thereof.

3. The compound according to claim 1, wherein ring B is a benzene ring or a pyridine ring, each of which is optionally further substituted by 1 to 3 $C_{1-6}$ alkyls, or a salt thereof.

4. The compound according to claim 1, wherein $R^1$ is $C_{1-6}$ alkyl or $C_{3-10}$ cycloalkyl, each of which is optionally substituted by 1 to 5 halogen atoms, or a salt thereof.

5. The compound according to claim 1, wherein $R^2$ is a hydrogen atom or $C_{1-6}$ alkyl optionally substituted by a halogen atom, or a salt thereof.

6. The compound according to claim 1, wherein X is CH, or a salt thereof.

7. (3R)-1-(4-((1-(4-(5-chloropyrimidin-2-yl)-2-methylphenyl)-4,4,4-trifluorobutyl)amino)benzoyl)piperidine-3-carboxylic acid or a salt thereof.

8. (3R)-1-(4-((4,4,4-trifluoro-1-(2-methyl-4-(5-(trifluoromethyl)pyrimidin-2-yl)phenyl)butyl)amino)benzoyl)piperidine-3-carboxylic acid or a salt thereof.

9. (3R)-1-(4-((4,4,4-trifluoro-1-(2-methyl-4-(4,5,6,7-tetrahydro-2H-indazol-2-yl)phenyl)butyl)amino)benzoyl)piperidine-3-carboxylic acid or a salt thereof.

10. A medicament comprising the compound according to claim 1 or a salt thereof.

11. The medicament according to claim 10, which is a glucagon receptor antagonist.

12. The medicament according to claim 10, which is a glucose production inhibitor.

13. The medicament according to claim 10, which is a therapeutic agent for diabetes.

14. A method for the treatment of diabetes in a mammal, comprising administering an effective amount of the compound according to claim 1 or a salt thereof to the mammal.

15. A method of antagonizing a glucagon receptor in a mammal, comprising administering an effective amount of the compound according to claim 1 or a salt thereof to the mammal.

16. A method of suppressing glucose production in a mammal, comprising administering an effective amount of the compound according to claim 1 or a salt thereof to the mammal.

* * * * *

SEQUENCE LISTING

<160> NUMBER OF SEQ ID NOS: 2

<210> SEQ ID NO 1
<211> LENGTH: 31
<212> TYPE: DNA
<213> ORGANISM: Artificial Sequence

```
<220> FEATURE:
<223> OTHER INFORMATION: PCR primer

<400> SEQUENCE: 1
aatagaattc atgccccct gccagccaca g                              31

<210> SEQ ID NO 2
<211> LENGTH: 36
<212> TYPE: DNA
<213> ORGANISM: Artificial Sequence
<220> FEATURE:
<223> OTHER INFORMATION: PCR primer

<400> SEQUENCE: 2
ctaagcggcc gctcagaagg ggctctcagc caatct                        36
```